(12) United States Patent
Feng et al.

(10) Patent No.: US 10,494,661 B2
(45) Date of Patent: Dec. 3, 2019

(54) STABILIZER FOR PRESERVING BIOLOGICAL SAMPLES

(71) Applicant: BGI SHENZHEN, Shenzhen (CN)

(72) Inventors: Qiang Feng, Shenzhen (CN); Mo Han, Shenzhen (CN); Liang Xiao, Shenzhen (CN); Jun Wang, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 137 days.

(21) Appl. No.: 15/546,264

(22) PCT Filed: Jan. 27, 2015

(86) PCT No.: PCT/CN2015/071608
§ 371 (c)(1),
(2) Date: Jul. 25, 2017

(87) PCT Pub. No.: WO2016/011798
PCT Pub. Date: Jan. 28, 2016

(65) Prior Publication Data
US 2018/0334703 A1   Nov. 22, 2018

(51) Int. Cl.
| C12Q 1/68 | (2018.01) |
| C12Q 1/6806 | (2018.01) |
| C07D 213/16 | (2006.01) |
| C12N 9/96 | (2006.01) |
| C07D 213/20 | (2006.01) |
| A01N 1/02 | (2006.01) |

(52) U.S. Cl.
CPC ......... *C12Q 1/6806* (2013.01); *A01N 1/0205* (2013.01); *C07D 213/16* (2013.01); *C07D 213/20* (2013.01); *C12N 9/96* (2013.01)

(58) Field of Classification Search
USPC ......................................................... 435/6.1
See application file for complete search history.

(56) References Cited

U.S. PATENT DOCUMENTS

| 5,110,929 A | 5/1992 | Paradies |
| 2005/0032183 A1 | 2/2005 | Osslund et al. |

FOREIGN PATENT DOCUMENTS

| CN | 1829739 | 9/2006 |
| CN | 101484576 | 7/2009 |
| CN | 102333788 | 1/2012 |
| CN | 103540575 | 1/2014 |
| EP | 1736542 A1 | 12/2006 |
| WO | WO 2007/022483 A2 | 2/2007 |
| WO | WO 2009/137078 | 11/2009 |
| WO | WO 2010/025859 A2 | 3/2010 |
| WO | WO 2010/011888 | 10/2010 |
| WO | WO 2012/018638 | 2/2012 |
| WO | WO 2012/018638 A2 | 2/2012 |
| WO | WO 2012/018639 A2 | 2/2012 |

OTHER PUBLICATIONS

Zhao et al., "On preparation of N-Octyl Pyridium Bromide and conductivity in Ethanol solution", Journal of Shenyang Normal University (Natural Science), 2012, vol. 30 No. 2, 262-264.

*Primary Examiner* — Jezia Riley
(74) *Attorney, Agent, or Firm* — James S. Keddie; Bozicevic, Field & Francis LLP

(57) ABSTRACT

Disclosed are a stabilizer for storage of a biological sample, a composition for storage of a nucleic acid and/or a polypeptide in a biological sample under non-freezing conditions, a kit comprising the composition, a mixture comprising the composition and a biological sample, and a method for storage of a nucleic acid and/or a polypeptide in a biological sample under non-freezing conditions. The integrity and stability of the nucleic acid and/or polypeptide in a biological sample can be stored for a long time under non-freezing conditions by using the stabilizer according to the invention, and therefore the stabilizer has a good application prospect.

12 Claims, 18 Drawing Sheets

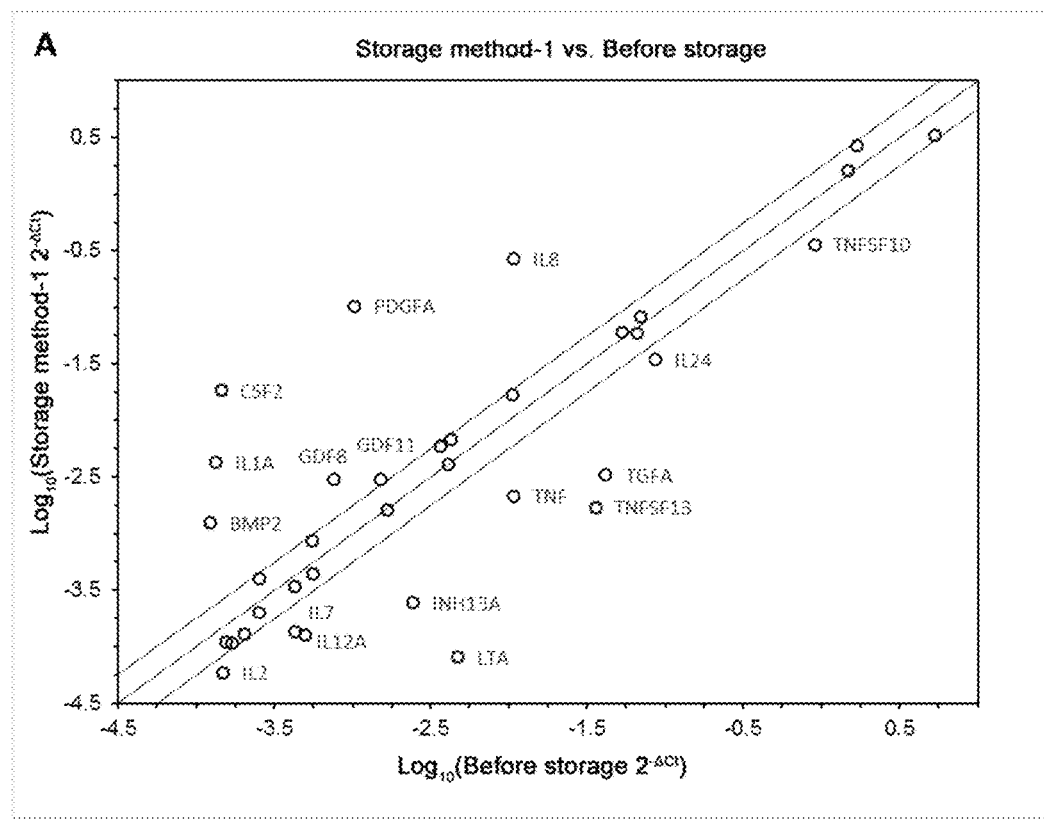
Fig. 21-A

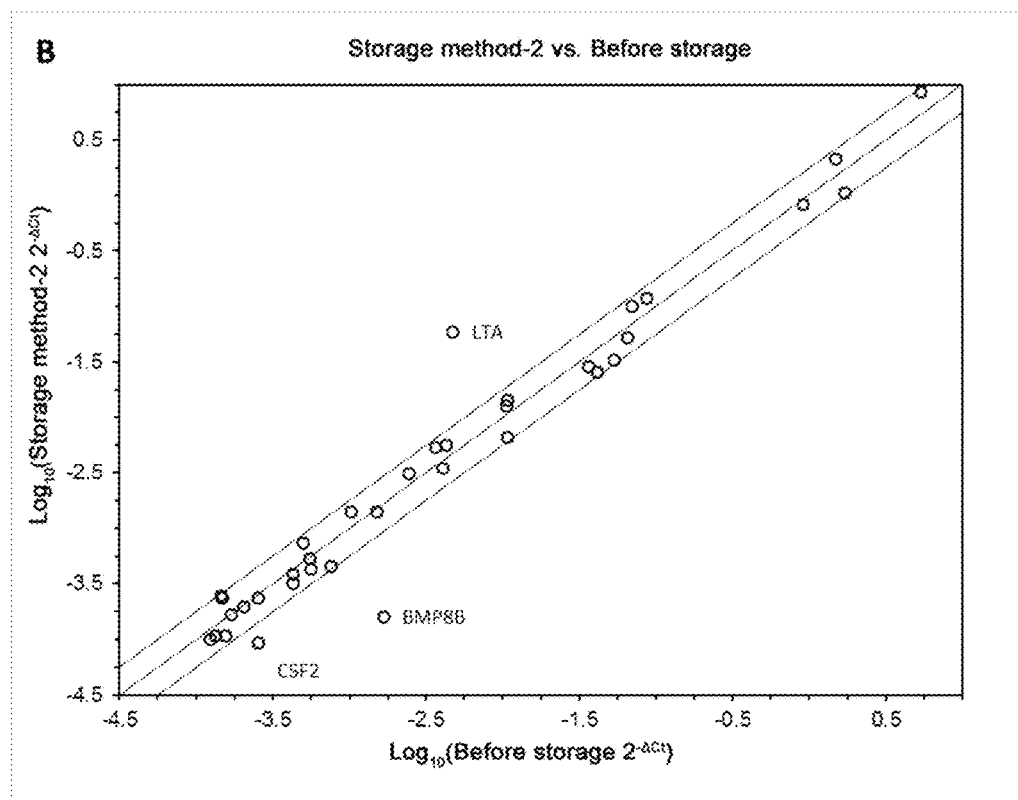
Fig. 21-B

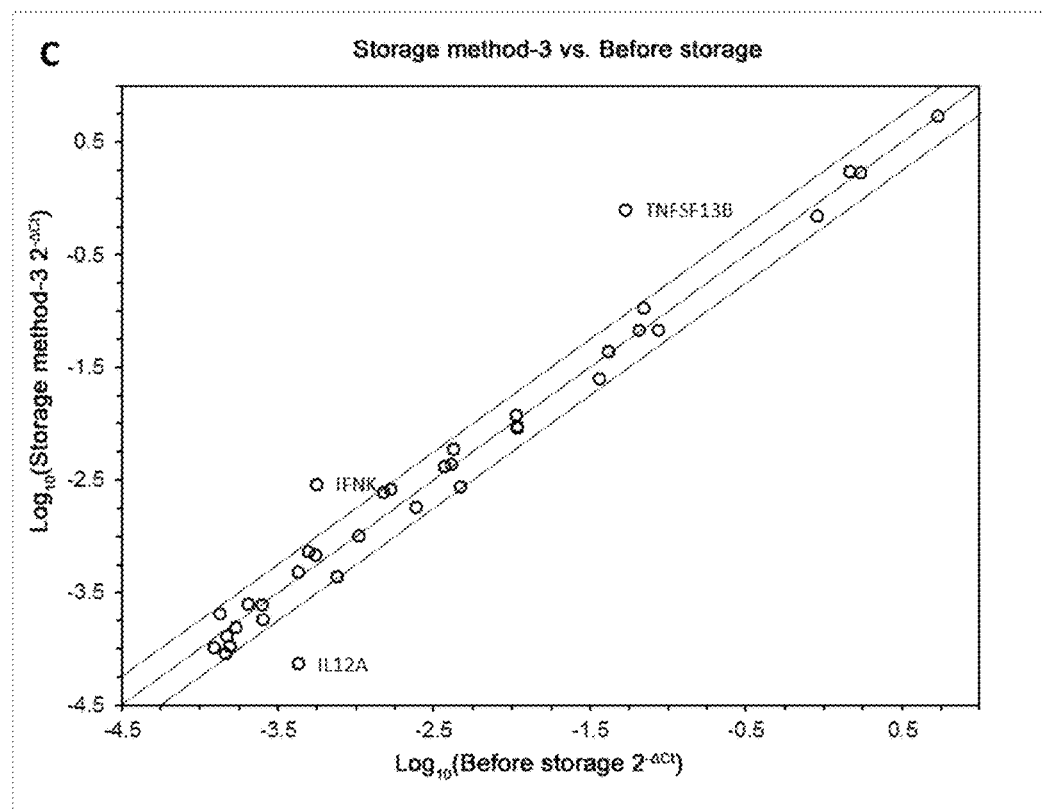
Fig. 21-C

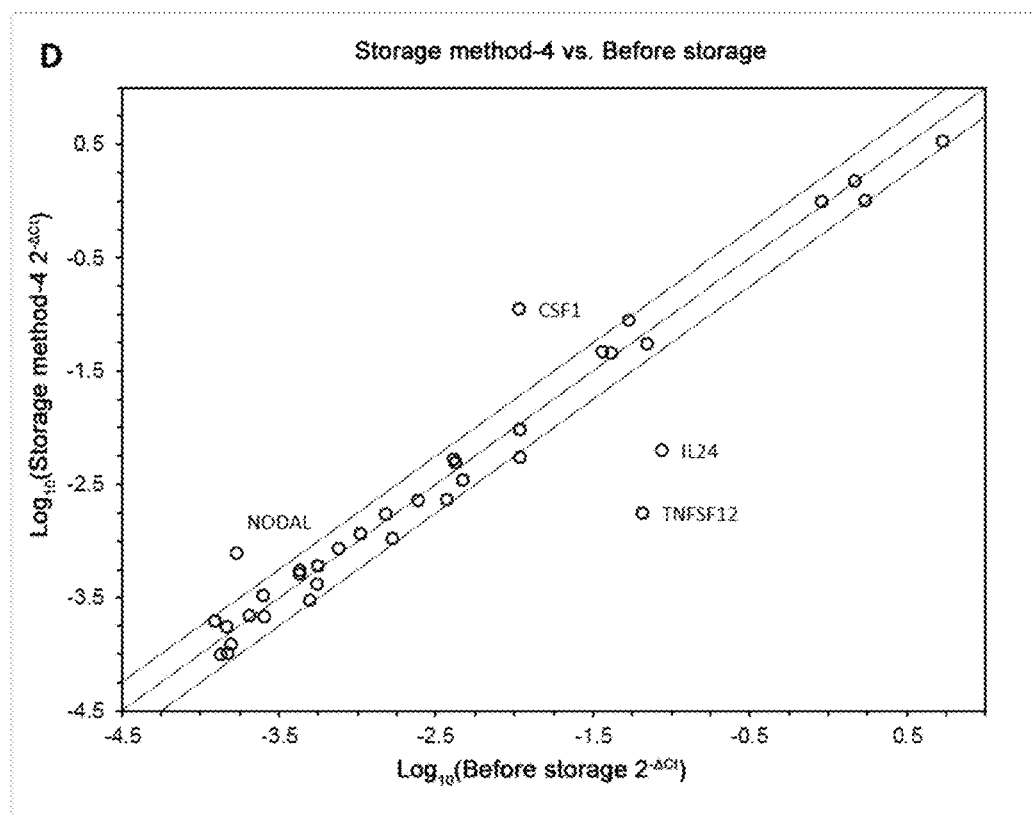
Fig. 21-D

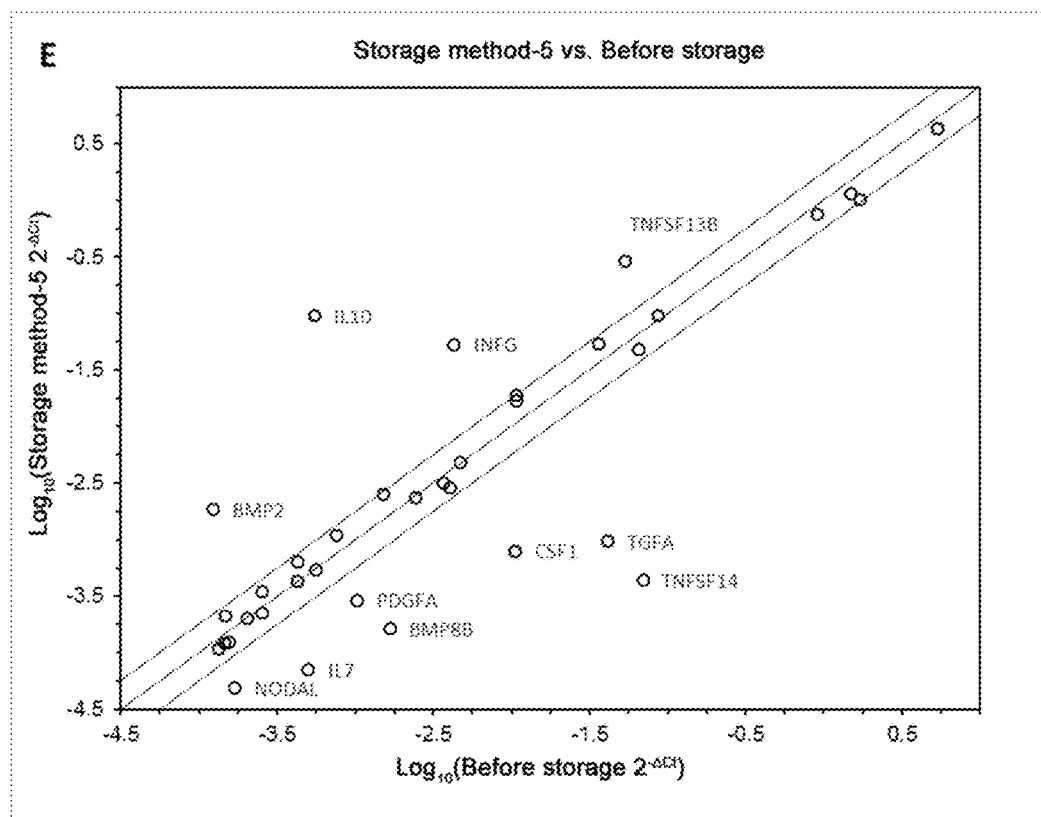
Fig. 21-E

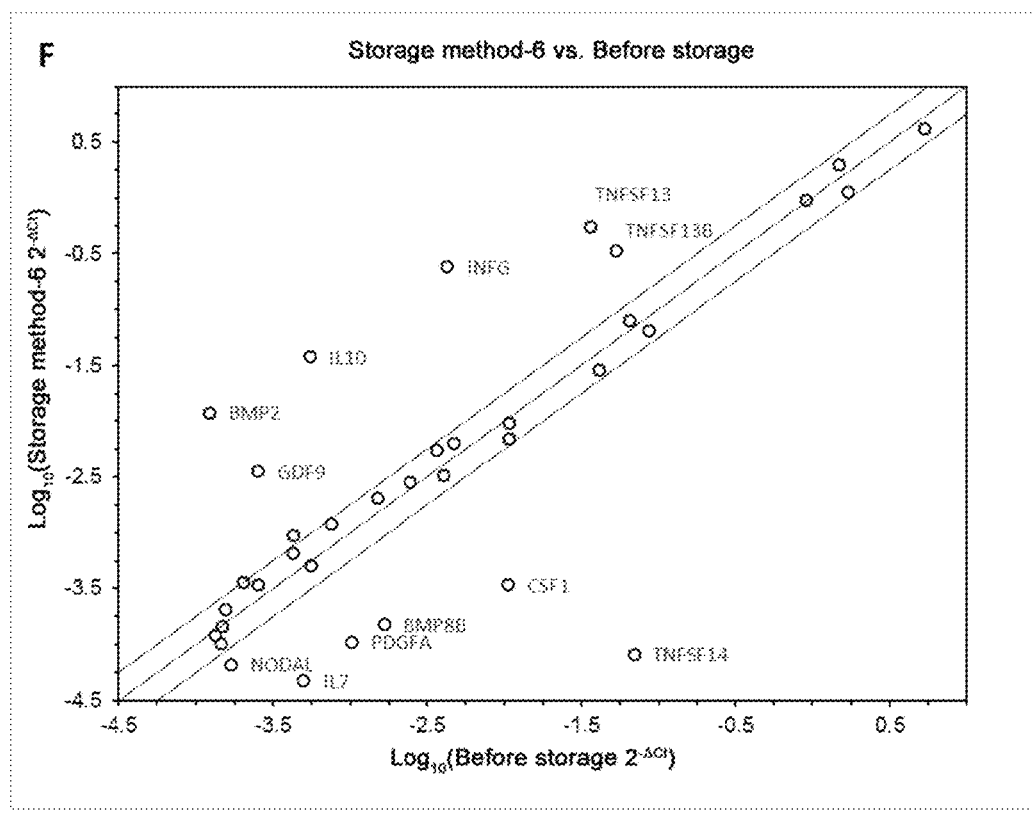
Fig. 21-F

STABILIZER FOR PRESERVING BIOLOGICAL SAMPLES

CROSS-REFERENCE TO RELATED APPLICATIONS

This application is a national phase filed under 35 U.S.C. § 371 of International Application No. PCT/CN2015/071608, filed on Jan. 27, 2015, which application is incorporated by reference herein.

TECHNICAL FIELD

The invention relates to a stabilizer for storage of a biological sample, particularly a composition for storage of a nucleic acid and/or a polypeptide in a biological sample under non-freezing conditions, a kit comprising the composition, a mixture comprising the composition and a biological sample, and a method for storage of a nucleic acid and/or a polypeptide in a biological sample under non-freezing conditions.

BACKGROUND ART

Researches in the field of life sciences are based on the analysis of biological materials or samples, mineral substances or chemical substances. Among them, biological materials or samples include samples from animal body surface or body fluid, such as oral scraps, saliva, sputum, blood and urine; nucleic acid samples, such as genomic DNA, PCR products, cloned DNA and RNA; protein samples, such as enzymes and polypeptides; microorganisms, including prokaryotes, such as bacteria, archaebacteria, viruses (e.g., bacteriophage, prion); eukaryotes, such as protozoan, and fungi (e.g., yeasts); lower plants, such as algae; advanced plants and animal samples, including various cells, such as somatic cells, stem cells, germ cells (sperm cells and egg cells), and various tissue samples, etc.

Biological samples are most frequently placed and stored in devices contained with liquid medium or a buffer solution, and they require storage at such subzero temperature (e.g., −20° C. or −70° C.~−80° C.). In some cases, samples have to be dried first, and then are stored at room temperature (WO 2005/113147, US 2005/0276728, US 2006/0099567), or 4° C., or −20° C., or −70~−80° C. However, the highly labile nature of biological samples makes it extremely difficult to preserve their biological activity over extended time periods. Although lyophilization of nucleic acid and protein samples can extend the storage life, the subsequent loss of activity upon reconstitution in a liquid makes lyophilization a less than ideal storage technique.

In addition to storage, biological samples generally need to be transported. In transportation of biological samples, ice, dry ice or other refrigerating equipment can be used to provide a freezing environment. However, when the time for transportation is too long, for example, international transportation or even intercontinental transportation, and especially when the refrigerating equipment and energy are deficient, it is not that easy to obtain a low-temperature or even freezing environment.

Therefore, when collecting biological samples, particularly collecting samples from a large population over vast territory, if a room-temperature storage method without expansive refrigerating equipment can be used, while integrity and stability of samples can be retained to the largest extent for a long time, thereby reducing the effects on the subsequent analysis, it will hold an enormous advantage.

CONTENTS OF INVENTION

The inventors surprisingly obtain a composition for stable storage of biological sample under non-freezing conditions and a method for storage of a biological sample, through repeated experiments by paying a lot of creative work, and thus accomplishes the invention.

In the first aspect, the invention relates to a composition for storage of nucleic acid and/or a polypeptide in a biological sample, comprising:

1) at least one compound of Formula I:

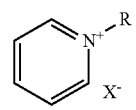

wherein R is selected from the group consisting of alkyl, alkenyl, cycloalkyl, cycloalkenyl, arylformylalkyl, and

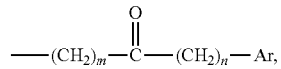

each of which is optionally substituted with a substituent selected from the group consisting of alkyl, hydroxyl, amino, nitro, and halogen;

m and n are each independently 0, 1, 2 or 3;

X⁻ represents an anion;

2) one, two or three of the following three agents:
 (1) at least one precipitant;
 (2) at least one lower alcohol; and
 (3) at least one chaotrope.

In some embodiments of the invention, the composition further comprises one or more agents selected from:
 (a) a reducing agent;
 (b) a polymerase inhibitor;
 (c) a pH buffer;
 (d) a chelating agent; and
 (e) water.

In some embodiments of the invention, the composition comprises one of the following formulations:
 (i) the compound of Formula I, a precipitant, a lower alcohol, a polymerase inhibitor, and a pH buffer;
 (ii) the compound of Formula I, a chaotrope, a lower alcohol, a polymerase inhibitor, and a pH buffer;
 (iii) the compound of Formula I, a precipitant, a lower alcohol, a reducing agent, and a pH buffer; and
 (iv) the compound of Formula I, a chaotrope, a lower alcohol, a reducing agent, and a pH buffer.

In some embodiments of the invention, the compound of Formula I is comprised in an amount of 1-10% (w/v or v/v), the chaotrope is comprised in an amount of 2.5-5M (mol/L), the pH buffer is comprised in an amount of 50-400 mM (mmol/L), the lower alcohol is comprised in an amount of 20-50% (v/v), the reducing agent is comprised in an amount of 5-50 mM, the precipitant is comprised in an amount of 2.5-5M, and the polymerase inhibitor is comprised in an amount of 0.1-0.5 mM.

In some particular embodiments of the invention, the compound of Formula I is comprised in an amount of, for example, 2-8% (w/v or v/v), such as 4% (w/v or v/v).

In some particular embodiments of the invention, the chaotrope is comprised in an amount of, for example, 3-4M, such as 3.5-4M.

In some particular embodiments of the invention, the pH buffer is comprised in an amount of, for example, 100-400 mM, such as 200-300 mM.

In some particular embodiments of the invention, the lower alcohol is comprised in an amount of, for example, 20-40% (v/v), such as 25%-35% (v/v), 30% (v/v).

In some particular embodiments of the invention, the reducing agent is comprised in an amount of, for example, 10-50 mM, such as 15-40 mM, e.g., 20-25 mM.

In some particular embodiments of the invention, the precipitant is comprised in an amount of, for example, 3-4.5 M, such as 3.5-4.2M.

In some particular embodiments of the invention, the polymerase inhibitor is comprised in an amount of, for example, 0.2-0.3 mM.

In some embodiments of the invention, wherein R is selected from the group consisting of $C_{1-10}$alkyl, $C_{2-10}$alkenyl, $C_{3-10}$cycloalkyl, $C_{3-10}$cycloalkenyl, arylformyl$C_{1-10}$alkyl, and

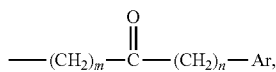

each of which is optionally substituted with a substituent selected from the group consisting of $C_{1-10}$alkyl, hydroxyl, amino, nitro, and halogen;

m and n are each independently 0, 1, 2 or 3.

In some embodiments of the invention, wherein the anion is selected from the group consisting of bromine ion, chlorine ion, iodine ion, $C_{1-10}$alkylsulfonate, hexafluorophosphate, methylsulfate, ethylsulfate, tetrafluoroborate, trifluoromethanesulfonate and bis(trifluoromethylsulfonyl)imide.

In some embodiments of the invention, wherein R is selected from the group consisting of $C_{1-10}$alkyl, and benzoyl$C_{1-10}$alkyl.

In some embodiments of the invention, wherein the compound of Formula I is selected from the group consisting of:

N-octylpyridinium bromide, N-butylpyridinium bromide, and N-phenacylpyridinium bromide.

In some embodiments of the invention, wherein the precipitant is selected from lithium chloride, lithium hydroxide, sulfosalicylic acid, and 5-((4-(dimethylamino)phenyl)methylene)-2-thioxo-4-thiazolidinone.

In some embodiments of the invention, wherein the lower alcohol is selected from methanol, ethanol, propanol, isopropanol, n-butanol and isobutanol.

In some embodiments of the invention, wherein the chaotrope is selected from guanidine hydrochloride, guanidine thiocyanate, potassium thiocyanate, sodium thiocyanate and urea.

In some embodiments of the invention, wherein the chelating agent is selected from diethylenetriaminepentaacetic acid (DTPA), ethylenediaminetetraacetic acid (EDTA), ethylene glycol-bis-(2-aminoethylether)-N,N,N',N'-tetraacetic acid (EGTA), 1,2-cyclohexanediaminetetraaceticacid (CDTA), 1,2-bis(2-aminophenoxy)-ethane-N,N,N',N'-tetraacetic acid (BAPTA), 1,4,7,10-tetraazacyclododecane-1,4,7,10-tetraacetic acid (DOTA), N-(2-hydroxyethyl)ethylenediamine-N,N',N'-triacetic acid (HEDTA), nitrilotriacetic acid (NTA).

In some embodiments of the invention, wherein the reducing agent is selected from 2-mercaptoethanol, thiosulfate, tris(2-carboxyethyl)phosphine hydrochloride (TCEP), dithiothreitol, and dithioerythritol.

In some embodiments of the invention, wherein the pH buffer is selected from citric acid, tartaric acid, malic acid, sulfosalicylic acid, 5-sulfobenzene-1,3-dicarboxylic acid, oxalic acid, boric acid, N-(2-hydroxyethyl)piperazine, 3-(cyclohexylamino)-1-propanesulfonic acid (CAPS), 3-(cyclohexylamino)-2-hydroxyl-1-propanesulfonic acid (CAPSO), 4-(2-hydroxyethyl)-1-piperazinepropanesulfonic acid (HEPPS), N-2-hydroxyethylpiperazine-N-2-ethanesulfonic acid (HEPES), 2-morpholinoethanesulfonic Acid (MES), 3-morpholinopropanesulfonic acid (MOPS), 3-(N-morpholino)-2-hydroxylpropanesulfonic acid (MOPSO), piperazine-1,4-bis(ethanesulfonic acid) (PIPES), N-[Tris(hydroxymethyl)methyl]-3-aminopropanesulfonic acid (TAPS), N-[Tris(hydroxymethyl)methyl]-3-amino-2-hydroxypropanesulfonic acid (TAPSO), N-[tris(hydroxymethyl)methyl]-2-aminoethanesulfonic acid (TES), diglycine, N-[tris(hydroxymethyl)methyl]glycine, tri(hydroxymethyl)aminomethane (tris) and 2-[bis(2-hydroxyethyl)amino]-2-(hydroxymethyl)-1,3-propanediol.

In some embodiments of the invention, wherein the polymerase inhibitor is selected from one or more of rifamycin-S, rifamycin-SV, antimycin, and erythromycin.

In some embodiments of the invention, the composition further comprises a surfactant or a detergent.

In some embodiments of the invention, wherein the surfactant or detergent is selected from TritonX-100, Nonidet P40 and non-ionic detergent Brij.

In some embodiments of the invention, wherein the nucleic acid comprises one or more DNA and/or RNA molecules.

In some embodiments of the invention, wherein the biological sample comprises one or more selected from: DNA, RNA, whole blood, buffy coat of whole blood, urine, feces, serum, serosal fluid, plasma, lymph, cerebrospinal fluid, saliva, mucosal secretion, vaginal discharge, ascites, pleural fluid, pericardial fluid, peritoneal fluid, abdominal fluid, cell culture medium, tissue culture medium, buccal cells, bacterium, viruses, yeast cells, plasmid DNA, mRNA, tRNA, rRNA, siRNA, miRNA, hnRNA, cDNA, protein, polypeptide, lipid, glycolipid, glycoprotein, oligosaccharide, polysaccharide, vaccine, cell, tissue, cell lysate, homogenate or extract, tissue lysate, biopsy specimen, blood sample, tissue explant, organ culture and biology liquid.

In the second aspect, the invention relates to a mixture obtained by mixing the composition according to the first aspect of the invention with a biological sample.

In some embodiments of the invention, wherein the biological sample comprises one or more selected from: DNA, RNA, whole blood, buffy coat of whole blood, urine, feces, serum, serosal fluid, plasma, lymph, cerebrospinal fluid, saliva, mucosal secretion, vaginal discharge, ascites, pleural fluid, pericardial fluid, peritoneal fluid, abdominal fluid, cell culture medium, tissue culture medium, buccal cells, bacterium, viruses, yeast cells, plasmid DNA, mRNA, tRNA, rRNA, siRNA, miRNA, hnRNA, cDNA, protein, polypeptide, lipid, glycolipid, glycoprotein, oligosaccharide, polysaccharide, vaccine, cell, tissue, cell lysate, homogenate or extract, tissue lysate, biopsy specimen, blood sample, tissue explant, organ culture and biology liquid.

In some embodiments of the invention, the mixture according to the second aspect of the invention is stored under non-freezing conditions for at least 1 day, 3 days, 7 days, 10 days, 20 days, 30 days, 40 days, 50 days, 60 days, 70 days, 90 days or 180 days.

The invention further relates to a kit, comprising the composition according to the first aspect of the invention, for storage of a nucleic acid and/or a polypeptide in a biological sample under non-freezing conditions.

In some embodiments of the invention, wherein the biological sample comprises one or more selected from: DNA, RNA, whole blood, buffy coat of whole blood, urine, feces, serum, serosal fluid, plasma, lymph, cerebrospinal fluid, saliva, mucosal secretion, vaginal discharge, ascites, pleural fluid, pericardial fluid, peritoneal fluid, abdominal fluid, cell culture medium, tissue culture medium, buccal cells, bacterium, viruses, yeast cells, plasmid DNA, mRNA, tRNA, rRNA, siRNA, miRNA, hnRNA, cDNA, protein, polypeptide, lipid, glycolipid, glycoprotein, oligosaccharide, polysaccharide, vaccine, cell, tissue, cell lysate, homogenate or extract, tissue lysate, biopsy specimen, blood sample, tissue explant, organ culture and biology liquid.

The invention further relates to a method for storage of a nucleic acid and/or a polypeptide in a biological sample under non-freezing conditions, comprising:

1) mixing the biological sample with the composition according to the first aspect of the invention; and 2) storage of the mixture obtained in step 1) under non-freezing conditions for at least 1 day, 3 days, 7 days, 10 days, 20 days, 30 days, 40 days, 50 days, 60 days, 70 days, 90 days or 180 days.

In some embodiments of the invention, wherein the biological sample comprises one or more selected from: DNA, RNA, whole blood, buffy coat of whole blood, urine, feces, serum, serosal fluid, plasma, lymph, cerebrospinal fluid, saliva, mucosal secretion, vaginal discharge, ascites, pleural fluid, pericardial fluid, peritoneal fluid, abdominal fluid, cell culture medium, tissue culture medium, buccal cells, bacterium, viruses, yeast cells, plasmid DNA, mRNA, tRNA, rRNA, siRNA, miRNA, hnRNA, cDNA, protein, polypeptide, lipid, glycolipid, glycoprotein, oligosaccharide, polysaccharide, vaccine, cell, tissue, cell lysate, homogenate or extract, tissue lysate, biopsy specimen, blood sample, tissue explant, organ culture and biology liquid.

The invention further relates to use of the composition according to the first aspect of the invention for storage of a nucleic acid and/or a polypeptide in a biological sample under non-freezing conditions.

In some embodiments of the invention, wherein the biological sample comprises one or more selected from: DNA, RNA, whole blood, buffy coat of whole blood, urine, feces, serum, serosal fluid, plasma, lymph, cerebrospinal fluid, saliva, mucosal secretion, vaginal discharge, ascites, pleural fluid, pericardial fluid, peritoneal fluid, abdominal fluid, cell culture medium, tissue culture medium, buccal cells, bacterium, viruses, yeast cells, plasmid DNA, mRNA, tRNA, rRNA, siRNA, miRNA, hnRNA, cDNA, protein, polypeptide, lipid, glycolipid, glycoprotein, oligosaccharide, polysaccharide, vaccine, cell, tissue, cell lysate, homogenate or extract, tissue lysate, biopsy specimen, blood sample, tissue explant, organ culture and biology liquid.

The invention provides a stabilizer composition for storage of a biological sample and a method for storage of a biological sample, which have the following advantages over the prior art: 1. with storage at room temperature, without dehydration treatment, and independent of expansive freezing and drying equipment; 2. being able to retain the integrity and stability of a sample for a long time to the maximum extent, and reduce the influences on the subsequent analysis; 3. the storage method being convenient for use and transportation, and particularly suitable for sampling from a large population over vast territory; and 4. having a better effect than the existing stabilizers.

The invention and the terms used in the invention are further illustrated as follows.

The term "alkyl" used in the invention refers to a saturated straight or branched monovalent hydrocarbon, for example, $C_{1-10}$ alkyl, $C_{1-6}$ alkyl, $C_{1-3}$ alkyl. The "$C_{1-10}$ alkyl" refers to a straight or branched alkyl having 1-10 carbon atoms, e.g., methyl, ethyl, propyl, isopropyl, n-butyl, sec-butyl, tert-butyl, isobutyl, pentyl, 2-pentyl, isopentyl, neopentyl, hexyl, 2-hexyl, 3-hexyl, 3-methylpentyl, heptyl, octyl, etc. The term "$C_{1-6}$ alkyl" refers to a straight or branched alkyl having 1-6 carbon atoms, i.e., 1, 2, 3, 4, 5 or 6 carbon atoms, typically, methyl, ethyl, n-propyl, isopropyl, n-butyl, isobutyl, tert-butyl, pentyl, hexyl, etc. Similarly, the term "$C_{1-3}$ alkyl" refers to a straight or branched alkyl having 1, 2 or 3 carbon atoms, i.e., methyl, ethyl, n-propyl, and isopropyl.

The term "alkenyl" used in the invention refers to a straight or branched unsaturated hydrocarbon containing at least one carbon-carbon double bond. $C_2$-$C_{10}$alkenyl refers to an alkenyl having 2-10 carbon atoms and at least one double bond, including vinyl, propenyl, 1-but-3-enyl, 1-pent-3-enyl, 1-hex-5-enyl, etc., more preferably, lower alkenyl having 3-5 carbon atoms.

The term "halogen" used in the invention refers to F, Cl, Br and I atom.

The term "cycloalkyl" used in the invention refers to a saturated carbocyclic ring group having 3, 4, 5, 6, 7, 8, 9 or 10 carbon atoms. Examples of the group include cyclopropyl, cyclobutyl, cyclopentyl, cyclohexyl, etc.

The term "aryl" used in the invention refers to an optionally substituted monocyclic or bicyclic unsaturated aromatic system comprising at least one unsaturated aromatic ring, preferably having 6~10 carbon atoms, i.e., 6, 7, 8, 9 or 10 carbon atoms. Examples of aryl in the invention include phenyl, naphthyl, 1,2,3,4-tetrahydronaphthyl, indenyl, and the like.

In the invention, the arylformylalkyl refers to aryl

alkyl, e.g., aryl

$C_{1-10}$alkyl, e.g., phenyl

$C_{1-10}$alkyl, wherein the definition of alkyl or $C_{1-10}$alkyl is as described above.

In the invention, the

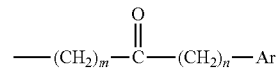

is, for example,

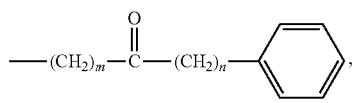

wherein m and n are each independently 0, 1, 2, or 3.

In some embodiments of the invention, the biological sample is selected from a whole blood sample, an embryonic kidney cell sample, a brain tissue sample, a tumor tissue sample (e.g., a tumor tissue sample of breast cancer), a urine sample, and a saliva sample.

In some embodiments of the invention, the biological sample is derived from vertebrate, for example, mammal, such as human, murine, cattle, sheep, horse, pig, monkey, and the like.

In the invention, the nucleic acid include DNA and/or RNA; the DNA includes, but is not limited to, genomic DNA, cDNA, plasmid DNA, etc.; the RNA includes, but is not limited to mRNA, tRNA, rRNA, siRNA, miRNA, hnRNA, etc.

In the invention, the polypeptide generally refers to a compound formed by dehydration-condensation of more than 10 amino acid molecules, and is also called protein when the number of amino acids is greater than 50 or 100.

In the invention, the precipitant refers to a compound that affects the solubility of nucleic acid and/or polypeptide molecules. In some embodiments of the invention, the precipitant refers to a substance that can promote precipitation of nucleic acid and/or polypeptide molecules from a biological sample, including, but not limited to lithium chloride, lithium hydroxide, sulfosalicylic acid, and 5-((4-(dimethylamino)phenyl)methylene)-2-thioxo-4-thiazolidinone; its concentration is, for example, 0.05-5M, such as 0.1, 0.5, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, and 5.0M.

In the invention, the lower alcohol has a relatively short straight or branched carbon chain, for example, the length of the carbon chain is not more than 8, 7, 6, 5, 4, or 3 carbon atoms; concentration of the lower alcohol is, for example, 5-50% (v/v), such as 5%, 10%, 15%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, and 50% (v/v).

In the invention, kinds of the chaotrope are well known in the art, which refer to substances that can interfere biological macromolecules, e.g., interfere formation of the secondary, tertiary or quaternary structure of polypeptide, protein, nucleic acid (including DNA and/or RNA) and the like, or, denaturate the biological macromolecules; a person skilled in the art can select a specific chaotrope depending on a specific biological sample; concentration of the chaotrope is, for example, 0.05-5M, such as 0.1, 0.5, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0M.

In the invention, the compound of Formula I is comprised in an amount of, for example, 0.1%-10% (w/v or v/v), such as 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0% (w/v or v/v).

In the invention, the compound of Formula I may be in a liquid, solid or viscous liquid state, and therefore the unit for its amount or concentration is w/v or v/v.

In some embodiments of the invention, the ratio of the composition for storage of a biological sample and the biological sample by volume is, for example, 10:1~1:10, such as 6:1, 5:1, 4:1, 3:1, 2:1, 1:1, 1:2, 1:3, 1:4, 1:5, 1:6.

In some embodiments of the invention, the pH value of the composition for storage of a biological sample can be adjusted depending on the biological sample, and the adjustment method is well known by a person skilled in the art, for example, the pH is 3-10; when storage of RNA, the pH may be 3.0-8.0, for example, 3.0-6.5, e.g., 3.2, 3.5, 3.7, 4.0, 4.2, 4.5, 4.7, 5.0, 5.3, 5.5, 5.8, 6.0, 6.3, 6.5; when storage of DNA, the pH may be 5.0-10.0, for example, 6.0-9.0, e.g., 6.3, 6.5, 6.8, 7.0, 7.4, 7.8, 8.0, 8.2, 8.4, 8.6, 8.8, 9.0.

In the embodiments of the invention, when the composition according to the invention is used to store a biological sample, it can stably store the biological sample under non-freezing conditions for a long time for example, and the storage period is, for example, longer than 1 day, 3 days, 7 days, 10 days, 20 days, 30 days, 40 days, 50 days, 60 days, 70 days, 90 days or 180 days, or, for example, is at least 1, 3, 4, 5, 6, 7, 8, 9, 10, 11, 12, 13, 14, 15, 16, 17, 18, 19, 20, 21, 22, 23, 24 months, or for example, at least 1, 2, 3, 4, 5 years.

In some embodiments of the invention, when a biological sample has been stored with the composition according to the invention for said period, the DNA molecules in the biological sample have an integrity of at least above 70%, e.g., 80%, 85%, 90%, 95%, 100%, as compared to those in the sample that has been stored at −20° C. or −80° C.; the RNA molecules in the biological sample have an integrity of at least above 70%, e.g., 80%, 85%, 90%, 95%, 100%, as compared to those in the sample that has been stored at −80° C.; the polypeptide molecules in the biological sample have an integrity of at least above 70%, e.g., 80%, 85%, 90%, 95%, 100%, as compared to those in the sample that has been stored at −20° C. or −80° C.

In the invention, the freezing condition refers to a condition below 0° C., i.e., the temperature condition for storage of a biological sample as generally used by a person skilled in the art, such as −10° C., −20° C., −30° C., −40° C., −50° C., −60° C., −70° C., and −80° C.

In the embodiments of the invention, the non-freezing condition refers to room temperature, e.g., 20-27° C., which, however, may be varied depending on geographic locations, seasons and surrounding environments, for example, from 15-19° C. or 18-23° C. to 22-29° C. or 28-32° C.

DESCRIPTION OF DRAWINGS

FIG. 21 shows the changes in transcription levels of 36 genes in the human whole blood samples stored under different conditions for different periods compared with the samples before storage. The human whole blood sample was stored at room temperature with the addition of the stabilizer with Formulation 2.4 for 3 days or 7 days (FIG. 21-C, FIG. 21-D); or stored by utilizing PAXgene™ Blood RNA Tube at room temperature for 3 days or 7 days (FIG. 21-E, FIG. 21-F); or directly stored at room temperature without stabilizer for 3 days (FIG. 21-A); or stored at −80° C. without stabilizer for 7 days (FIG. 21-B). House-keeping genes PRL13A and GAPDH, were used as internal reference, and the changes in expression levels of the 36 genes relative to the levels at the time of sample collection were determined by ΔΔCq method.

SPECIFIC MODES FOR CARRYING OUT THE INVENTION

Figure 1:
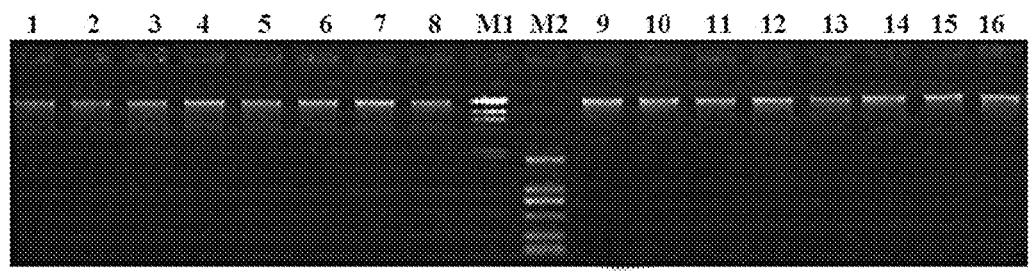
FIG. 1 and FIG. 2 show the agarose gel electrophoretograms.

The embodiments of the invention are described by combining the following examples. However, a person skilled in the art understands that the following examples are only intended to describe the invention, and shall not be regarded as defining the scope of the invention. In the case where the concrete conditions are not indicated in the examples, the examples are carried out according to conventional conditions or the conditions recommended by the manufacturer. The reagents or apparatuses, the manufacturers of which are not indicated, are the conventional products that are commercially available.

In the following examples, standard cellular and molecular biological technologies are used, which are substantively based on the known methods (for example: Sambrook, J., Fritsch, E. F. and Maniatis, 1. (1989) Molecular Cloning: A Laboratory Manual, Cold Spring Harbor Laboratory Press, New York; Current Protocols, Nucleic Acid Chemistry, Molecular Biology, Wiley and Sons, 2003; Current Protocols, Protein Sciences, Cell Biology, Wiley and Sons, 2003). Unless otherwise specified, all the reagents used in the following examples were purchased from Sigma Aldrich Company (St. Louis, Mo.).

Formulations of a stabilizer for storage of nucleic acid and polypeptide molecules in a biological sample are exemplified in the following Table 1 and Table 2, wherein the Formulation Number corresponds to the Formulation number of the stabilizer used in Examples.

TABLE 1

Examples of formulations of a stabilizer for storage of nucleic acid and polypeptide molecules in a biological sample

| Formulation No. | Chaotrope or precipitant | Buffer | Lower alcohol | Polymerase inhibitor | Compound added (v/v %) | pH value |
|---|---|---|---|---|---|---|
| 1.1 | 3M guanidine hydrochloride | 400 mM tri(hydroxymethyl)aminomethane | 40% (v/v %)ethanol | 0.4 mM rifamycin-S | 8% N-butylpyridinium bromide | 7 |
| 1.2 | 3M lithium chloride | 300 mM 3-morpholinopropanesulfonic acid | 30% (v/v %)ethanol | 0.1 mM rifamycin-SV, 0.2 mM antimycin | 6% N-butylpyridinium bromide | 7.1 |
| 1.3 | 5M lithium chloride | 400 mM 3-morpholinopropanesulfonic acid | 20% (v/v %)ethanol | 0.2 mM erythromycin | 5% N-octylpyridinium bromide | 7.2 |
| 1.4 | 5M guanidine hydrochloride | 400 mM tri(hydroxymethyl)aminomethane | 30% (v/v %)ethanol | 0.4 mM rifamycin-S | 8% N-butylpyridinium bromide | 7.2 |
| 1.5 | 2.5M guanidine hydrochloride | 300 mM 3-morpholinopropanesulfonic acid | 30% (v/v %)ethanol | 0.2 mM rifamycin-S | 2% N-octylpyridinium bromide | 7.4 |
| 1.6 | 3M lithium chloride | 200 mM 3-morpholinopropanesulfonic acid | 20% (v/v %)ethanol | 0.3 mM rifamycin-SV, 0.2 mM antimycin | 6% N-butylpyridinium bromide | 7.4 |
| 1.7 | 4M lithium chloride | 100 mM 3-morpholinopropanesulfonic acid | 30% (v/v %)ethanol | 0.2 mM erythromycin | 5% N-octylpyridinium bromide | 7.4 |
| 1.8 | 5M lithium chloride | 200 mM tri(hydroxymethyl)aminomethane | 50% (v/v %)ethanol | 0.2 mM rifamycin-SV, 0.3 mM antimycin | 6% N-butylpyridinium bromide | 7.4 |
| 1.9 | 5M guanidine hydrochloride | 300 mM tri(hydroxymethyl)aminomethane | 30% (v/v %)ethanol | 0.2 mM rifamycin-S | 3% N-butylpyridinium bromide | 7.4 |
| 1.10 | 2.5M guanidine hydrochloride | 400 mM 3-morpholinopropanesulfonic acid | 30% (v/v %)ethanol | 0.2 mM rifamycin-S | 2% N-octylpyridinium bromide | 7.5 |
| 1.11 | 3M guanidine hydrochloride | 300 mM 3-morpholinopropanesulfonic acid | 30% (v/v %)ethanol | 0.2 mM antimycin | 4% N-butylpyridinium bromide | 7.5 |
| 1.12 | 3M guanidine hydrochloride | 100 mM 3-morpholinopropanesulfonic acid | 30% (v/v %)ethanol | 0.2 mM antimycin | 4% N-butylpyridinium bromide | 7.5 |
| 1.13 | 3M guanidine hydrochloride | 200 mM 3-morpholinopropanesulfonic acid | 40% (v/v %)ethanol | 0.1 mM rifamycin-S | 3% N-octylpyridinium bromide | 7.6 |
| 1.14 | 4.5M lithium chloride | 100 mM 3-morpholinopropanesulfonic acid | 40% (v/v %)ethanol | 0.1 mM rifamycin-SV, 0.3 mM antimycin | 5% N-octylpyridinium bromide | 7.6 |
| 1.15 | 4M lithium chloride | 200 mM 3-morpholinopropanesulfonic acid | 30% (v/v %)ethanol | 0.2 mM erythromycin | 3% N-octylpyridinium bromide | 7.6 |
| 1.16 | 4M guanidine hydrochloride | 300 mM tri(hydroxymethyl)aminomethane | 40% (v/v %)ethanol | 0.2 mM rifamycin-S | 3% N-butylpyridinium bromide | 7.6 |
| 1.17 | 5M lithium chloride | 100 mM tri(hydroxymethyl)aminomethane | 50% (v/v %)ethanol | 0.2 mM rifamycin-SV, 0.2 mM antimycin | 8% N-butylpyridinium bromide | 7.6 |
| 1.18 | 3.5M lithium chloride | 200 mM 3-morpholinopropanesulfonic acid | 30% (v/v %)ethanol | 0.3 mM rifamycin-SV, 0.1 mM antimycin | 5% N-butylpyridinium bromide | 7.7 |
| 1.19 | 3M lithium chloride | 200 mM tri(hydroxymethyl)aminomethane | 30% (v/v %)ethanol | 0.2 mM erythromycin | 2% N-butylpyridinium bromide | 7.7 |
| 1.20 | 3M guanidine hydrochloride | 300 mM 3-morpholinopropanesulfonic acid | 40% (v/v %)ethanol | 0.3 mM rifamycin-S | 3% N-octylpyridinium bromide | 7.7 |

TABLE 1-continued

Examples of formulations of a stabilizer for storage of nucleic acid and polypeptide molecules in a biological sample

| Formulation No. | Chaotrope or precipitant | Buffer | Lower alcohol | Polymerase inhibitor | Compound added (v/v %) | pH value |
|---|---|---|---|---|---|---|
| 1.21 | 4M lithium chloride | 100 mM 3-morpholinopropanesulfonic acid | 40% (v/v %)ethanol | 0.2 mM rifamycin-SV, 0.3 mM antimycin | 5% N-octylpyridinium bromide | 7.7 |
| 1.22 | 4M guanidine hydrochloride | 200 mM 3-morpholinopropanesulfonic acid | 30% (v/v %)ethanol | 0.3 mM antimycin | 4% N-butylpyridinium bromide | 7.7 |
| 1.23 | 4M guanidine hydrochloride | 400 mM 3-morpholinopropanesulfonic acid | 50% (v/v %)ethanol | 0.3 mM antimycin | 6% N-butylpyridinium bromide | 7.7 |
| 1.24 | 4M guanidine hydrochloride | 400 mM 3-morpholinopropanesulfonic acid | 50% (v/v %)ethanol | 0.2 mM antimycin | 6% N-butylpyridinium bromide | 7.7 |
| 1.25 | 2.5M guanidine hydrochloride | 100 mM tri(hydroxymethyl)aminomethane | 20% (v/v %)ethanol | 0.2 mM antimycin | 5% N-butylpyridinium bromide | 7.8 |
| 1.26 | 3.5M lithium chloride | 200 mM 3-morpholinopropanesulfonic acid | 30% (v/v %)ethanol | 0.3 mM erythromycin | 3% N-octylpyridinium bromide | 7.8 |
| 1.27 | 3M lithium chloride | 400 mM tri(hydroxymethyl)aminomethane | 30% (v/v %)ethanol | 0.2 mM erythromycin | 2% N-butylpyridinium bromide | 7.8 |
| 1.28 | 4M lithium chloride | 200 mM 3-morpholinopropanesulfonic acid | 30% (v/v %)ethanol | 0.2 mM rifamycin-SV, 0.2 mM antimycin | 8% N-butylpyridinium bromide | 7.8 |
| 1.29 | 4M lithium chloride | 100 mM tri(hydroxymethyl)aminomethane | 30% (v/v %)ethanol | 0.2 mM rifamycin-SV, 0.2 mM antimycin | 8% N-butylpyridinium bromide | 7.8 |
| 1.30 | 4M guanidine hydrochloride | 100 mM tri(hydroxymethyl)aminomethane | 40% (v/v %)ethanol | 0.2 mM antimycin | 4% N-butylpyridinium bromide | 7.8 |
| 1.31 | 4M guanidine hydrochloride | 200 mM tri(hydroxymethyl)aminomethane | 40% (v/v %)ethanol | 0.2 mM rifamycin-S | 4% N-butylpyridinium bromide | 7.8 |
| 1.32 | 4M guanidine hydrochloride | 300 mM 3-morpholinopropanesulfonic acid | 40% (v/v %)ethanol | 0.2 mM rifamycin-S | 4% N-octylpyridinium bromide | 7.8 |
| 1.33 | 4M guanidine hydrochloride | 200 mM tri(hydroxymethyl)aminomethane | 50% (v/v %)ethanol | 0.2 mM antimycin | 4% N-octylpyridinium bromide | 7.8 |
| 1.34 | 2.5M guanidine hydrochloride | 300 mM tri(hydroxymethyl)aminomethane | 20% (v/v %)ethanol | 0.3 mM antimycin | 5% N-butylpyridinium bromide | 7.9 |
| 1.35 | 3.5M lithium chloride | 200 mM 3-morpholinopropanesulfonic acid | 30% (v/v %)ethanol | 0.1 mM rifamycin-SV, 0.2 mM antimycin | 8% N-butylpyridinium bromide | 7.9 |
| 1.36 | 3M guanidine hydrochloride | 300 mM tri(hydroxymethyl)aminomethane | 30% (v/v %)ethanol | 0.3 mM antimycin | 3% N-butylpyridinium bromide | 7.9 |
| 1.37 | 4.5M lithium chloride | 400 mM tri(hydroxymethyl)aminomethane | 40% (v/v %)ethanol | 0.2 mM erythromycin | 5% N-butylpyridinium bromide | 7.9 |
| 1.38 | 4M guanidine hydrochloride | 100 mM tri(hydroxymethyl)aminomethane | 50% (v/v %)ethanol | 0.2 mM antimycin | 5% N-octylpyridinium bromide | 7.9 |
| 1.39 | 3.5M lithium chloride | 300 mM 3-morpholinopropanesulfonic acid | 20% (v/v %)ethanol | 0.1 mM rifamycin-SV, 0.1 mM antimycin | 4% N-butylpyridinium bromide | 8 |
| 1.40 | 3.5M lithium chloride | 100 mM tri(hydroxymethyl)aminomethane | 30% (v/v %)ethanol | 0.1 mM rifamycin-SV, 0.2 mM antimycin | 4% N-butylpyridinium bromide | 8 |
| 1.41 | 3.5M lithium chloride | 300 mM 3-morpholinopropanesulfonic acid | 20% (v/v %)ethanol | 0.3 mM erythromycin | 4% N-octylpyridinium bromide | 8 |
| 1.42 | 3.5M lithium chloride | 300 mM 3-morpholinopropanesulfonic acid | 20% (v/v %)ethanol | 0.1 mM rifamycin-SV, 0.1 mM antimycin | 8% N-butylpyridinium bromide | 8 |
| 1.43 | 4.5M lithium chloride | 300 mM tri(hydroxymethyl)aminomethane | 40% (v/v %)ethanol | 0.3 mM erythromycin | 5% N-butylpyridinium bromide | 8 |
| 1.44 | 5M guanidine hydrochloride | 300 mM tri(hydroxymethyl)aminomethane | 50% (v/v %)ethanol | 0.3 mM antimycin | 5% N-octylpyridinium bromide | 8 |
| 1.45 | 3.5M lithium chloride | 300 mM tri(hydroxymethyl)aminomethane | 30% (v/v %)ethanol | 0.3 mM erythromycin | 4% N-butylpyridinium bromide | 8.1 |
| 1.46 | 3M guanidine hydrochloride | 300 mM tri(hydroxymethyl)aminomethane | 30% (v/v %)ethanol | 0.4 mM antimycin | 3% N-butylpyridinium bromide | 8.1 |
| 1.47 | 5M guanidine hydrochloride | 300 mM tri(hydroxymethyl)aminomethane | 30% (v/v %)ethanol | 0.3 mM antimycin | 6% N-octylpyridinium bromide | 8.1 |
| 1.48 | 3.5M lithium chloride | 200 mM tri(hydroxymethyl)aminomethane | 30% (v/v %)ethanol | 0.3 mM erythromycin | 4% N-butylpyridinium bromide | 8.2 |
| 1.49 | 3.5M lithium chloride | 200 mM tri(hydroxymethyl)aminomethane | 30% (v/v %)ethanol | 0.1 mM rifamycin-SV, 0.1 mM antimycin | 4% N-butylpyridinium bromide | 8.2 |
| 1.50 | 5M guanidine hydrochloride | 300 mM tri(hydroxymethyl)aminomethane | 30% (v/v %)ethanol | 0.4 mM antimycin | 6% N-octylpyridinium bromide | 8.2 |

TABLE 2

Examples of formulations of a stabilizer for storage of nucleic acid and polypeptide molecules in a biological sample

| Formulation No. | Chaotrope or precipitant | Buffer | Lower alcohol | Reducing agent | Additive (v/v %) | pH value |
|---|---|---|---|---|---|---|
| 2.1 | 4M guanidine hydrochloride | 300 mM 3-morpholinopropanesulfonic acid | 30% (v/v %)ethanol | 25 mM tris(2-carboxyethyl)phosphine hydrochloride | 2% N-phenacylpyridinium bromide | 7.6 |
| 2.2 | 4M guanidine hydrochloride | 300 mM 3-morpholinopropanesulfonic acid | 30% (v/v %)ethanol | 25 mM tris(2-carboxyethyl)phosphine hydrochloride | 8% N-butylpyridinium bromide | 7.6 |
| 2.3 | 4M guanidine hydrochloride | 300 mM 3-morpholinopropanesulfonic acid | 30% (v/v %)ethanol | 25 mM tris(2-carboxyethyl)phosphine hydrochloride | 4% N-octylpyridinium bromide | 7.6 |
| 2.4 | 4M guanidine hydrochloride | 200 mM tri(hydroxymethyl)aminomethane | 30% (v/v %)ethanol | 10 mM tris(2-carboxyethyl)phosphine hydrochloride | 4% N-octylpyridinium bromide | 7.6 |
| 2.5 | 4M guanidine hydrochloride | 200 mM tri(hydroxymethyl)aminomethane | 40% (v/v %)ethanol | 10 mM tris(2-carboxyethyl)phosphine hydrochloride | 4% N-octylpyridinium bromide | 7.8 |
| 2.6 | 4M guanidine hydrochloride | 250 mM N-(hydroxyethyl)piperazine | 40% (v/v %)ethanol | 10 mM tris(2-carboxyethyl)phosphine hydrochloride | 8% N-butylpyridinium bromide | 7.8 |
| 2.7 | 3.5M guanidine hydrochloride | 300 mM 3-morpholinopropanesulfonic acid | 40% (v/v %)ethanol | 50 mM tris(2-carboxyethyl)phosphine hydrochloride | 8% N-butylpyridinium bromide | 7.8 |
| 2.8 | 3.5M guanidine hydrochloride | 300 mM 3-morpholinopropanesulfonic acid | 40% (v/v %)ethanol | 50 mM tris(2-carboxyethyl)phosphine hydrochloride | 2% N-phenacylpyridinium bromide | 7.8 |
| 2.9 | 3.5M guanidine hydrochloride | 300 mM 3-morpholinopropanesulfonic acid | 30% (v/v %)ethanol | 50 mM tris(2-carboxyethyl)phosphine hydrochloride | 8% N-butylpyridinium bromide | 7.8 |
| 2.10 | 3.5M guanidine hydrochloride | 200 mM tri(hydroxymethyl)aminomethane | 30% (v/v %)ethanol | 15 mM dithiothreitol | 8% N-butylpyridinium bromide | 7.8 |
| 2.11 | 3.5M guanidine hydrochloride | 250 mM N-(hydroxyethyl)piperazine | 30% (v/v %)ethanol | 15 mM dithiothreitol | 4% N-octylpyridinium bromide | 8.1 |
| 2.12 | 3.5M lithium chloride | 200 mM tri(hydroxymethyl)aminomethane | 30% (v/v %)ethanol | 20 mM tris(2-carboxyethyl)phosphine hydrochloride | 4% N-octylpyridinium bromide | 7.8 |
| 2.13 | 3.5M lithium chloride | 300 mM 3-morpholinopropanesulfonic acid | 30% (v/v %)ethanol | 25 mM dithiothreitol | 4% N-octylpyridinium bromide | 8.1 |
| 2.14 | 3.5M lithium chloride | 300 mM 3-morpholinopropanesulfonic acid | 30% (v/v %)ethanol | 25 mM dithiothreitol | 8% N-butylpyridinium bromide | 7.8 |
| 2.15 | 3.5M lithium chloride | 300 mM 3-morpholinopropanesulfonic acid | 30% (v/v %)ethanol | 15 mM dithiothreitol | 4% N-octylpyridinium bromide | 8.1 |
| 2.16 | 3.5M lithium chloride | 250 mM N-(hydroxyethyl)piperazine | 30% (v/v %)ethanol | 20 mM tris(2-carboxyethyl)phosphine hydrochloride | 4% N-octylpyridinium bromide | 7.8 |
| 2.17 | 3.5M lithium chloride | 250 mM N-(hydroxyethyl)piperazine | 20% (v/v %)ethanol | 20 mM tris(2-carboxyethyl)phosphine hydrochloride | 4% N-octylpyridinium bromide | 8.2 |
| 2.18 | 4.2M lithium chloride | 300 mM 3-morpholinopropanesulfonic acid | 20% (v/v %)ethanol | 20 mM tris(2-carboxyethyl)phosphine hydrochloride | 2% N-phenacylpyridinium bromide | 8.2 |
| 2.19 | 4.2M lithium chloride | 200 mM tri(hydroxymethyl)aminomethane | 40% (v/v %)ethanol | 5 mM tris(2-carboxyethyl)phosphine hydrochloride | 2% N-phenacylpyridinium bromide | 8.2 |
| 2.20 | 4.5M guanidine hydrochloride | 100 mM tri(hydroxymethyl)aminomethane | 30% (v/v %)ethanol | 15 mM dithiothreitol | 5% N-butylpyridinium bromide | 7 |
| 2.21 | 2.5M guanidine hydrochloride | 200 mM tri(hydroxymethyl)aminomethane | 20% (v/v %)ethanol | 15 mM dithiothreitol | 8% N-butylpyridinium bromide | 7.1 |
| 2.22 | 4.2M lithium chloride | 250 mM N-(hydroxyethyl)piperazine | 40% (v/v %)ethanol | 5 mM tris(2-carboxyethyl)phosphine hydrochloride | 8% N-butylpyridinium bromide | 7.1 |
| 2.23 | 4.5M guanidine hydrochloride | 100 mM 3-morpholinopropanesulfonic acid | 30% (v/v %)ethanol | 50 mM tris(2-carboxyethyl)phosphine hydrochloride | 5% N-butylpyridinium bromide | 7.1 |
| 2.24 | 2.5M guanidine hydrochloride | 250 mM N-(hydroxyethyl)piperazine | 20% (v/v %)ethanol | 15 mM dithiothreitol | 6% N-octylpyridinium bromide | 7.2 |

TABLE 2-continued

Examples of formulations of a stabilizer for storage of nucleic acid and polypeptide molecules in a biological sample

| Formulation No. | Chaotrope or precipitant | Buffer | Lower alcohol | Reducing agent | Additive (v/v %) | pH value |
|---|---|---|---|---|---|---|
| 2.25 | 3M guanidine hydrochloride | 100 mM 3-morpholinopropanesulfonic acid | 30% (v/v %)ethanol | 25 mM tris(2-carboxyethyl)phosphine hydrochloride | 2% N-phenacylpyridinium bromide | 7.2 |
| 2.26 | 4.5M guanidine hydrochloride | 300 mM 3-morpholinopropanesulfonic acid | 40% (v/v %)ethanol | 50 mM tris(2-carboxyethyl)phosphine hydrochloride | 2% N-phenacylpyridinium bromide | 7.2 |
| 2.27 | 3M lithium chloride | 300 mM 3-morpholinopropanesulfonic acid | 20% (v/v %)ethanol | 15 mM dithiothreitol | 6% N-octylpyridinium bromide | 7.3 |
| 2.28 | 3M guanidine hydrochloride | 100 mM 3-morpholinopropanesulfonic acid | 30% (v/v %)ethanol | 25 mM tris(2-carboxyethyl)phosphine hydrochloride | 8% N-butylpyridinium bromide | 7.3 |
| 2.29 | 4.5M guanidine hydrochloride | 300 mM 3-morpholinopropanesulfonic acid | 40% (v/v %)ethanol | 50 mM tris(2-carboxyethyl)phosphine hydrochloride | 8% N-butylpyridinium bromide | 7.3 |
| 2.30 | 3.7M guanidine hydrochloride | 250 mM N-(hydroxyethyl)piperazine | 40% (v/v %)ethanol | 30 mM tris(2-carboxyethyl)phosphine hydrochloride | 8% N-butylpyridinium bromide | 7.4 |
| 2.31 | 3M lithium chloride | 300 mM 3-morpholinopropanesulfonic acid | 20% (v/v %)ethanol | 25 mM dithiothreitol | 6% N-octylpyridinium bromide | 7.4 |
| 2.32 | 3M guanidine hydrochloride | 100 mM 3-morpholinopropanesulfonic acid | 30% (v/v %)ethanol | 25 mM tris(2-carboxyethyl)phosphine hydrochloride | 4% N-octylpyridinium bromide | 7.4 |
| 2.33 | 3.7M guanidine hydrochloride | 200 mM tri(hydroxymethyl)aminomethane | 40% (v/v %)ethanol | 30 mM tris(2-carboxyethyl)phosphine hydrochloride | 5% N-octylpyridinium bromide | 7.5 |
| 2.34 | 3M lithium chloride | 300 mM 3-morpholinopropanesulfonic acid | 40% (v/v %)ethanol | 25 mM dithiothreitol | 8% N-butylpyridinium bromide | 7.5 |
| 2.35 | 3M guanidine hydrochloride | 200 mM tri(hydroxymethyl)aminomethane | 30% (v/v %)ethanol | 10 mM tris(2-carboxyethyl)phosphine hydrochloride | 4% N-octylpyridinium bromide | 7.5 |
| 2.36 | 3.7M guanidine hydrochloride | 200 mM tri(hydroxymethyl)aminomethane | 50% (v/v %)ethanol | 10 mM tris(2-carboxyethyl)phosphine hydrochloride | 5% N-octylpyridinium bromide | 7.6 |
| 2.37 | 3M lithium chloride | 200 mM tri(hydroxymethyl)aminomethane | 40% (v/v %)ethanol | 15 mM tris(2-carboxyethyl)phosphine hydrochloride | 4% N-octylpyridinium bromide | 7.6 |
| 2.38 | 3M guanidine hydrochloride | 200 mM tri(hydroxymethyl)aminomethane | 40% (v/v %)ethanol | 10 mM tris(2-carboxyethyl)phosphine hydrochloride | 4% N-octylpyridinium bromide | 7.6 |
| 2.39 | 3.7M guanidine hydrochloride | 100 mM 3-morpholinopropanesulfonic acid | 50% (v/v %)ethanol | 25 mM tris(2-carboxyethyl)phosphine hydrochloride | 4% N-octylpyridinium bromide | 7.7 |
| 2.40 | 3M lithium chloride | 150 mM N-(hydroxyethyl)piperazine | 40% (v/v %)ethanol | 5 mM tris(2-carboxyethyl)phosphine hydrochloride | 4% N-octylpyridinium bromide | 7.7 |
| 2.41 | 3M guanidine hydrochloride | 250 mM N-(hydroxyethyl)piperazine | 40% (v/v %)ethanol | 10 mM tris(2-carboxyethyl)phosphine hydrochloride | 8% N-butylpyridinium bromide | 7.7 |
| 2.42 | 2.5M guanidine hydrochloride | 300 mM 3-morpholinopropanesulfonic acid | 40% (v/v %)ethanol | 50 mM tris(2-carboxyethyl)phosphine hydrochloride | 8% N-butylpyridinium bromide | 7.8 |
| 2.43 | 3M lithium chloride | 150 mM N-(hydroxyethyl)piperazine | 20% (v/v %)ethanol | 5 mM tris(2-carboxyethyl)phosphine hydrochloride | 4% N-octylpyridinium bromide | 7.8 |
| 2.44 | 3M guanidine hydrochloride | 100 mM 3-morpholinopropanesulfonic acid | 30% (v/v %)ethanol | 25 mM tris(2-carboxyethyl)phosphine hydrochloride | 8% N-butylpyridinium bromide | 7.8 |
| 2.45 | 2.5M guanidine hydrochloride | 300 mM 3-morpholinopropanesulfonic acid | 40% (v/v %)ethanol | 50 mM tris(2-carboxyethyl)phosphine hydrochloride | 2% N-phenacylpyridinium bromide | 7.9 |
| 2.46 | 3M guanidine hydrochloride | 100 mM 3-morpholinopropanesulfonic acid | 30% (v/v %)ethanol | 25 mM tris(2-carboxyethyl)phosphine hydrochloride | 2% N-phenacylpyridinium bromide | 7.9 |
| 2.47 | 4.5M lithium chloride | 300 mM 3-morpholinopropanesulfonic acid | 20% (v/v %)ethanol | 5 mM tris(2-carboxyethyl)phosphine hydrochloride | 2% N-phenacylpyridinium bromide | 7.9 |
| 2.48 | 2.5M guanidine hydrochloride | 300 mM 3-morpholinopropanesulfonic acid | 20% (v/v %)ethanol | 50 mM tris(2-carboxyethyl)phosphine hydrochloride | 8% N-butylpyridinium bromide | 8 |

TABLE 2-continued

Examples of formulations of a stabilizer for storage of nucleic acid and polypeptide molecules in a biological sample

| Formulation No. | Chaotrope or precipitant | Buffer | Lower alcohol | Reducing agent | Additive (v/v %) | pH value |
|---|---|---|---|---|---|---|
| 2.49 | 4.5M lithium chloride | 200 mM tri(hydroxymethyl)aminomethane | 40% (v/v %)ethanol | 5 mM tris(2-carboxyethyl)phosphine hydrochloride | 2% N-phenacylpyridinium bromide | 8 |
| 2.50 | 4.5M lithium chloride | 250 mM N-(hydroxyethyl)piperazine | 40% (v/v %)ethanol | 5 mM tris(2-carboxyethyl)phosphine hydrochloride | 8% N-butylpyridinium bromide | 8.1 |

Example 1

1. Feces sample: fresh feces sample was provided by a healthy volunteer, and the same piece of feces sample was divided into 30 aliquots, each aliquot had a wet weight of about 0.2 g.

2. Storage method: 3 aliquots were directly stored in a refrigerator at −80° C. (control group); 9 aliquots were stored with the addition of 500 μL Stool DNA Stabilizer (a commercially available stabilizer) for each aliquot (purchased from B-Bridge International Company) (Group 1); 9 aliquots were stored with the addition of 500 μL stabilizer with Formulation 2.37 (Table 2) for each aliquot ((group 2), and 9 aliquots were stored without stabilizer (Group 3).

The samples of Groups 1, 2 and 3 were stored at three temperatures (room temperature/25° C., 4° C., −20° C.) for 1 days, 3 days, and 7 days, respectively, and then placed in a refrigerator at −80° C.;

The samples are designated in this manner A-B-C, wherein A refers to the formulation number of a stabilizer (N: no stabilizer, 4: Stool DNA Stabilizer (a commercially available stabilizer), 6: Formulation 2.37), B refers to the storage temperature (N: room temperature, 4:4° C., 20: −20° C.) and C refers to the storage period (unit: day). Control group is stored at −80° C.

3. Extraction of total genomic DNA from feces: after the storage of all the samples, extraction of total genomic DNA from feces was carried out at the same time, wherein the DNA extraction method was the same as described above (Manichanh, C. et al. Reduced diversity of fecal microbiota in Crohn's disease revealed by a metagenomic approach. Gut 55, 205-211, doi: gut. 2005.073817 [pii]10.1136/gut.2005.073817 (2006), which is incorporated herein by reference).

4. Determination of DNA concentration: DNA concentration was determined by using a fluorescent quantitation instrument (Qubit Fluorometer) and a test kit (Qubit® dsDNA BR); detailed steps were performed according to manufacturer's instructions, and the results are shown in Table 3.

TABLE 3

Results of determination of DNA concentration

| Sample name | Loading amount (μL) | Determined concentration (ng/μL) |
|---|---|---|
| 4-N-1 | 1 | 264 |
| 4-N-3 | 1 | 252 |
| 4-N-7 | 1 | 198 |
| 4-4-1 | 1 | 175 |
| 4-4-3 | 1 | 226 |

TABLE 3-continued

Results of determination of DNA concentration

| Sample name | Loading amount (μL) | Determined concentration (ng/μL) |
|---|---|---|
| 4-4-7 | 1 | 186 |
| 4-20-1 | 1 | 254 |
| 4-20-3 | 1 | 228 |
| 4-20-7 | 1 | 130 |
| 6-N-1 | 1 | 161 |
| 6-N-3 | 1 | 180 |
| 6-N-7 | 1 | 190 |
| 6-4-1 | 1 | 80.2 |
| 6-4-3 | 1 | 240 |
| 6-4-7 | 1 | 192 |
| 6-20-1 | 1 | 178 |
| 6-20-3 | 1 | 135 |
| 6-20-7 | 1 | 212 |
| N-N-1 | 1 | 140 |
| N-N-3 | 1 | 110 |
| N-N-7 | 1 | 136 |
| N-4-1 | 1 | 240 |
| N-4-3 | 1 | 129 |
| N-4-7 | 1 | 145 |
| N-20-1 | 1 | 230 |
| N-20-3 | 1 | 244 |
| N-20-7 | 1 | 252 |
| Control 1 | 1 | 314 |
| Control 2 | 1 | 276 |
| Control 3 | 1 | 380 |

Figure 2:
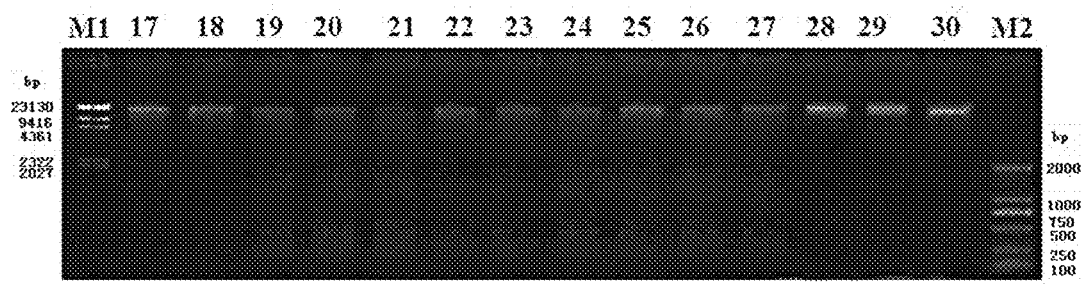

5. Determination of sample integrity: sample integrity was determined by agarose gel electrophoresis, the sample was loaded (determined concentration×loading amount=100±1.5 ng, see Table 4) onto 1% agarose gel for separation, and after gel electrophoresis at a constant voltage of 150 V for 40 min, photographs were taken by ultraviolet ray (UVI) imaging system. The electrophoretograms are shown in FIG. 1 and FIG. 2.

It can be found that there is significant difference in electrophoretograms between the DNA extracted from the groups with the addition of stabilizer (Group 1, Group 2) and the DNA extracted from the group without stabilizer (Group 3): the electrophoresis bands of the DNA extracted from the samples without stabilizer (Sample well Nos. 19-27) were relatively smeared, and with tails backwards towards small fragments, indicating relatively severe degradation of the DNA in the samples without stabilizer; in view of the signal intensity of the main electrophoresis bands, the main bands of the DNA extracted from the samples in the groups with stabilizer (Sample well Nos. 1-18) had strong intensity, while the main bands in the groups without stabilizer had weak intensity, particularly, the intensity tended to disappear in Sample N—N-7 (Sample well No. 21), which also demonstrated that the stabilizers enabled more DNA in the samples to maintain in a long-chain state that was undegraded. Said results show that the stabilizers of the invention can significantly retain the sample integrity.

TABLE 4

Loading data and results of electrophoresis

| Sample well No. | Sample name | Dilution factor (X) | Loading amount (μL) | Sample integrity |
|---|---|---|---|---|
| M1 | λ-Hind III digest(Takara) | 1 | 3 | |
| 1 | 4-N-1 | 1 | 0.38 | Slight degradation |
| 2 | 4-N-3 | 1 | 0.4 | Slight degradation |
| 3 | 4-N-7 | 1 | 0.51 | Slight degradation |
| 4 | 4-4-1 | 1 | 0.57 | Slight degradation |
| 5 | 4-4-3 | 1 | 0.44 | Slight degradation |
| 6 | 4-4-7 | 1 | 0.54 | Slight degradation |
| 7 | 4-20-1 | 1 | 0.39 | Slight degradation |
| 8 | 4-20-3 | 1 | 0.44 | Slight degradation |
| 9 | 4-20-7 | 1 | 0.77 | Slight degradation |
| 10 | 6-N-1 | 1 | 0.62 | Slight degradation |
| 11 | 6-N-3 | 1 | 0.56 | Slight degradation |
| 12 | 6-N-7 | 1 | 0.53 | Slight degradation |
| 13 | 6-4-1 | 1 | 1.25 | Slight degradation |
| 14 | 6-4-3 | 1 | 0.42 | Slight degradation |
| 15 | 6-4-7 | 1 | 0.52 | Slight degradation |
| 16 | 6-20-1 | 1 | 0.56 | Slight degradation |
| 17 | 6-20-3 | 1 | 0.74 | Slight degradation |
| 18 | 6-20-7 | 1 | 0.47 | Slight degradation |
| 19 | N-N-1 | 1 | 0.71 | Moderate degradation |
| 20 | N-N-3 | 1 | 0.91 | Moderate degradation |
| 21 | N-N-7 | 1 | 0.74 | Severe degradation |
| 22 | N-4-1 | 1 | 0.42 | Moderate degradation |
| 23 | N-4-3 | 1 | 0.78 | Moderate degradation |
| 24 | N-4-7 | 1 | 0.69 | Moderate degradation |
| 25 | N-20-1 | 1 | 0.43 | Moderate degradation |
| 26 | N-20-3 | 1 | 0.41 | Moderate degradation |
| 27 | N-20-7 | 1 | 0.4 | Moderate degradation |
| 28 | Control 1 | 1 | 0.32 | Slight degradation |
| 29 | Control 2 | 1 | 0.36 | Slight degradation |
| 30 | Control 3 | 1 | 0.26 | Slight degradation |
| M2 | D2000 (Tiangen) | 1 | 6 | |

Example 2

A library was constructed for the DNA extracted from each sample obtained in Example 1 (insert size≤800 bp), and then metagenomics sequencing of the V4 and V5 regions of 16S rDNA gene was carried out, using Ion PGM and 318-v2 chip, with a sequencing data of 8 Mb per sample, and detailed steps were performed according to manufacturer's instructions.

Based on the sequencing results, each of the samples was analyzed for the microorganism constitution (percentage), and the correlation between samples was calculated at the genus level (using Excel CORREL function).

16S rDNA analysis method:

1. Sequencer:

Ion Torrent PGM (Personal Genome Machine)

2. Sequencing Strategy:

Directed sequencing of V4-V5 regions of 16S rDNA gene (reverse direction: V5→V4)

3. Software:

mothur v.1.33.3 (http://www.mothur.org)

4. 16S rDNA Database:

RDP (Ribosomal Database Project, http://rdp.cme.ms-u.edu/)

Silva (http://www.arb-silva.de/)

Figure 3:
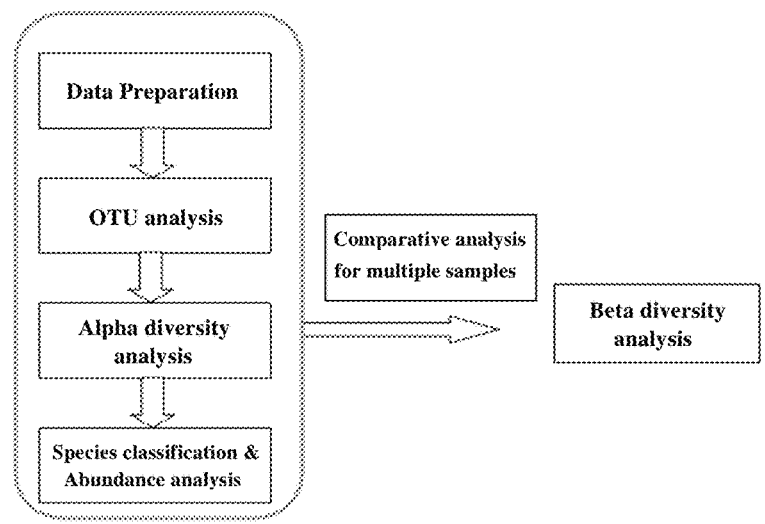
FIG. 3 shows the flow diagram of 16S rDNA analysis method.
Figures 4, 5:
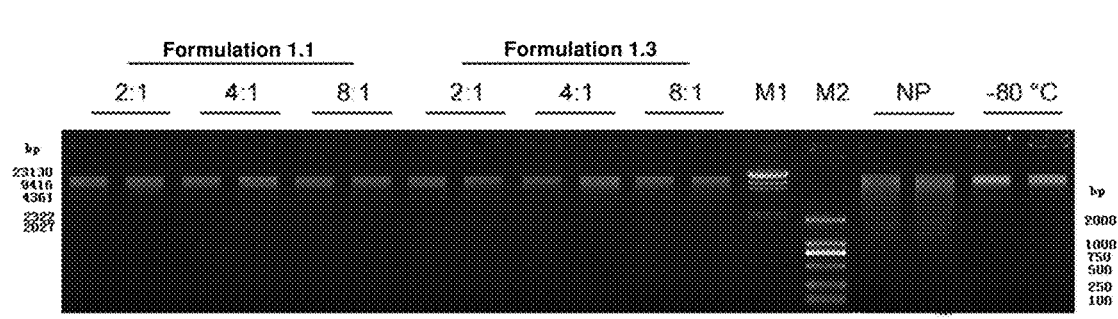
FIG. 4 shows the correlation between each two samples at genus level (employing Excel CORREL function). According to the relative abundance of each species at genus level (Tables 5-1, 5-2, 5-3), the correlation coefficient between each two samples is calculated; by comparison to the calculated correlation coefficients in Tables 6-1, 6-2, 6-3, the higher the grayscale is, the higher the correlation coefficient is; in contrast, the lower the grayscale is, the lower the correlation coefficient is. Due to the limited cell size, the value is shown as "1" or "0", wherein when the correlation coefficient≥0.5, it is represented by "1"; when the correlation coefficient<0.5, it is represented by "0".
FIG. 5 shows the agarose gel electrophoretogram of the DNA extracted from the human whole blood samples stored under different conditions. The human whole blood sample was first mixed with the stabilizer with Formulation 1.1 or Formulation 1.3 at three different ratios, and then stored at room temperature; or directly stored at room temperature without stabilizer (NP); or stored at −80° C. without stabilizer. 10 days later, DNA was extracted from the sample by using Qia Amp Purification mini Kit (Qiagen, Valencia, Calif.), and was subjected to electrophoresis on 0.8% agarose gel.

5. Analysis Process:

By using the sequencing technology for hypervariable regions of 16S rDNA gene, the PCR products of the V4-V5 regions of 16S rDNA were sequenced. The filtered reads obtained by sequencing were aligned to the 16S rDNA database Silva; the aligned reads were then subjected to OTU clustering, and information on species classification was obtained in accordance with RDP database annotation, followed by other analysis such as diversity analysis. The analysis process is shown in FIG. 3. FIG. 4 shows the correlation between each two samples at the genus level (see Tables 6-1, 6-2, 6-3): according to the relative abundance of each species at the genus level (see Tables 5-1, 5-2, 5-3), the correlation coefficient between each two samples was calculated.

6. Result Analysis:

In view of correlation between each two samples at the genus level, compared with the group stored with Stool DNA Stabilizer (a commercially available stabilizer), the group stored with the stabilizer with Formulation 2.37, were more similar to the control group (0.9829 vs. 0.9676 on average), and the correlation between the results at genus level and storage temperature or period is higher within this group (0.9937 vs. 0.9862 on average). The negative control group without stabilizer (Group 3) can keep the correlation with the control group only at the storage condition of −20° C. (0.9966 on average). Therefore, said results show that the stabilizers of the invention can retain the integrity and stability of DNA molecules in the biological samples (feces) for a long time, and have a better effect in storage than the products of prior art.

TABLE 5-1

Relative abundance of each species at the genus level (%)

| Genus | Control 1 | Control 2 | Control 3 | 4-20-1 | 4-20-3 |
|---|---|---|---|---|---|
| *Actinomyces* | 0.013196094 | 0 | 0 | 0 | 0 |
| *Corynebacterium* | 0 | 0 | 0 | 0 | 0 |
| *Nesterenkonia* | 0.013196094 | 0 | 0 | 0 | 0 |
| *Bifidobacterium* | 0 | 0 | 0.013453518 | 0 | 0 |
| *Asaccharobacter* | 0 | 0 | 0 | 0 | 0 |
| *Atopobium* | 0 | 0 | 0 | 0 | 0 |
| *Collinsella* | 0.039588282 | 0.096142291 | 0.053814072 | 0.015264845 | 0.030674847 |
| *Eggerthella* | 0 | 0 | 0 | 0 | 0 |
| *Olsenella* | 0.026392188 | 0 | 0 | 0 | 0 |
| *Bacteroides* | 8.313539192 | 6.693906982 | 6.417328131 | 10.53274309 | 10.75153374 |
| *Barnesiella* | 0.620216416 | 0.432640308 | 0.645768869 | 0.641123493 | 0.659509202 |
| *Butyricimonas* | 0.514647664 | 0.384569162 | 0.363244989 | 1.190657915 | 1.257668712 |
| *Odoribacter* | 0.329902349 | 0.45667588 | 0.403605543 | 0.686918028 | 0.720858896 |
| *Parabacteroides* | 1.636315651 | 1.454152145 | 1.654782726 | 1.816516562 | 1.641104294 |
| *Paraprevotella* | 0.409078913 | 0.252373513 | 0.28252388 | 0.351091436 | 0.27607362 |
| *Prevotella* | 25.81155978 | 19.02415575 | 16.97833984 | 23.12624027 | 25.59815951 |
| *Alistipes* | 8.775402481 | 8.003845692 | 7.708865868 | 8.990993741 | 8.634969325 |
| *Hymenobacter* | 0.197941409 | 0.240355726 | 0.269070362 | 0.564799267 | 0.36809816 |
| *Bacillus* | 0 | 0 | 0 | 0 | 0 |
| *Gemella* | 0.013196094 | 0 | 0 | 0 | 0 |
| *Listeria* | 0.013196094 | 0.024035573 | 0.013453518 | 0.015264845 | 0.015337423 |
| *Staphylococcus* | 0.013196094 | 0 | 0.013453518 | 0 | 0 |
| *Enterococcus* | 0.105568752 | 0.072106718 | 0.147988699 | 0.137383606 | 0.04601227 |
| *Lactobacillus* | 0.06598047 | 0.13219565 | 0.040360554 | 0.045794535 | 0.030674847 |
| *Weissella* | 0.013196094 | 0.012017786 | 0 | 0 | 0 |
| *Lactococcus* | 0.118764846 | 0.144213436 | 0.161442217 | 0.12211876 | 0.153374233 |
| *Streptococcus* | 1.029295329 | 1.285903137 | 1.264630701 | 0.885361014 | 0.690184049 |
| *Clostridium_sensu_stricto* | 0.026392188 | 0 | 0 | 0 | 0.015337423 |
| *Mogibacterium* | 0 | 0 | 0 | 0.015264845 | 0 |
| *Anaerofustis* | 0 | 0 | 0 | 0 | 0 |
| *Eubacterium* | 1.346001584 | 1.297920923 | 1.574061617 | 0.915890704 | 0.950920245 |
| *Anaerostipes* | 0.554235946 | 0.745102752 | 0.645768869 | 0.259502366 | 0.567484663 |
| *Blautia* | 0.092372658 | 0.252373513 | 0.322884434 | 0.228972676 | 0.153374233 |
| *Clostridium_XIVa* | 1.082079704 | 1.958899171 | 1.681689762 | 1.679132957 | 1.472392638 |
| *Coprococcus* | 0.013196094 | 0.024035573 | 0.026907036 | 0.015264845 | 0.061349693 |
| *Dorea* | 2.757983637 | 3.617353683 | 4.103323019 | 2.488169745 | 2.45398773 |
| *Hespellia* | 1.121667986 | 1.213796419 | 0.968653303 | 0.778507098 | 0.858895706 |
| *Lachnospiracea_incertae_sedis* | 5.872261811 | 8.809037375 | 8.690972689 | 7.998778812 | 6.947852761 |
| *Lactonifactor* | 0 | 0 | 0 | 0 | 0 |
| *Moryella* | 0 | 0.024035573 | 0.040360554 | 0 | 0 |
| *Oribacterium* | 0.013196094 | 0 | 0 | 0 | 0 |
| *Roseburia* | 0.105568752 | 0.144213436 | 0.201802771 | 0.290032056 | 0.27607362 |
| *Syntrophococcus* | 0.026392188 | 0.024035573 | 0.040360554 | 0.03052969 | 0.030674847 |
| *Clostridium_XI* | 0.039588282 | 0.060088932 | 0.040360554 | 0.076324225 | 0.061349693 |
| *Acetanaerobacterium* | 0.013196094 | 0.024035573 | 0.013453518 | 0 | 0.015337423 |
| *Anaerofilum* | 0 | 0.012017786 | 0.013453518 | 0.015264845 | 0 |
| *Clostridium_IV* | 0.804961731 | 1.466169931 | 0.91483923 | 1.511219661 | 1.840490798 |
| *Ethanoligenens* | 0.026392188 | 0.276409085 | 0.107628145 | 0.320561746 | 0.076687117 |
| *Flavonifractor* | 0 | 0.024035573 | 0 | 0.076324225 | 0 |
| *Hydrogenoanaerobacterium* | 0 | 0 | 0 | 0 | 0 |
| *Oscillibacter* | 2.96912114 | 3.533229179 | 3.645903404 | 2.869790872 | 2.54601227 |
| *Ruminococcus* | 3.312219583 | 4.338420863 | 4.789452442 | 2.640818196 | 2.59202454 |
| *Saccharofermentans* | 0 | 0 | 0 | 0 | 0.015337423 |
| *Sporobacter* | 0.395882819 | 0.420622521 | 0.403605543 | 0.167913296 | 0.245398773 |
| *Clostridium_XVIII* | 1.148060174 | 1.850739094 | 1.331898291 | 1.251717295 | 1.319018405 |
| *Coprobacillus* | 0 | 0.048071145 | 0.107628145 | 0.076324225 | 0 |
| *Erysipelotrichaceae_incertae_sedis* | 0.052784376 | 0.060088932 | 0.053814072 | 0.06105938 | 0.09202454 |
| *Phascolarctobacterium* | 0.303510161 | 0.288426872 | 0.363244989 | 0.274767211 | 0.061349693 |
| *Dialister* | 0.013196094 | 0 | 0.053814072 | 0 | 0.015337423 |
| *Veillonella* | 0.013196094 | 0.024035573 | 0 | 0.03052969 | 0.030674847 |
| *Gemmiger* | 2.441277382 | 2.655930778 | 2.852145836 | 1.892840788 | 1.625766871 |
| *Burkholderia* | 0 | 0 | 0 | 0 | 0 |
| *Limnohabitans* | 0.50145157 | 0.564835957 | 0.605408314 | 0.610593802 | 0.398773006 |
| *Parasutterella* | 0.356294537 | 0.204302368 | 0.403605543 | 1.373836056 | 1.242331288 |
| *Bilophila* | 0.052784376 | 0 | 0.013453518 | 0.015264845 | 0.015337423 |
| *Desulfovibrio* | 0 | 0.012017786 | 0.013453518 | 0.03052969 | 0 |
| *Klebsiella* | 0.052784376 | 0 | 0.013453518 | 0.03052969 | 0.015337423 |
| *Morganella* | 0 | 0.024035573 | 0 | 0.03052969 | 0 |
| *Acinetobacter* | 0 | 0 | 0 | 0 | 0 |
| *Acholeplasma* | 0.369490631 | 0.444658094 | 0.56504776 | 0.259502366 | 0.32208589 |

TABLE 5-1-continued

Relative abundance of each species at the genus level (%)

| Genus | Sample Relative abundance of each species at the genus level (%) | | | | |
|---|---|---|---|---|---|
| | 4-20-7 | 4-4-1 | 4-4-3 | 4-4-7 | 4-N-1 |
| *Actinomyces* | 0 | 0 | 0 | 0 | 0 |
| *Corynebacterium* | 0 | 0 | 0 | 0 | 0 |
| *Nesterenkonia* | 0 | 0 | 0 | 0 | 0 |
| *Bifidobacterium* | 0 | 0 | 0 | 0 | 0 |
| *Asaccharobacter* | 0 | 0 | 0 | 0 | 0 |
| *Atopobium* | 0 | 0 | 0 | 0 | 0 |
| *Collinsella* | 0.027839644 | 0.034578147 | 0.028344671 | 0.015513497 | 0.028328612 |
| *Eggerthella* | 0 | 0 | 0 | 0 | 0 |
| *Olsenella* | 0 | 0 | 0 | 0 | 0 |
| *Bacteroides* | 10.76002227 | 12.65560166 | 12.54251701 | 10.54917778 | 9.688385269 |
| *Barnesiella* | 0.876948775 | 0.812586445 | 0.977891156 | 1.194539249 | 0.934844193 |
| *Butyricimonas* | 0.974387528 | 1.262102351 | 1.06292517 | 1.28762023 | 1.104815864 |
| *Odoribacter* | 0.7655902 | 0.778008299 | 0.722789116 | 0.822215327 | 0.793201133 |
| *Parabacteroides* | 2.004454343 | 2.472337483 | 2.182539683 | 2.187403041 | 1.558073654 |
| *Paraprevotella* | 0.417594655 | 0.276625173 | 0.311791383 | 0.403350915 | 0.467422096 |
| *Prevotella* | 23.32962138 | 20.79875519 | 20.01133787 | 18.63170959 | 29.64589235 |
| *Alistipes* | 8.421492205 | 10.47717842 | 10.10487528 | 10.22339435 | 9.33427762 |
| *Hymenobacter* | 0.45935412 | 0.466804979 | 0.453514739 | 0.589512876 | 0.467422096 |
| *Bacillus* | 0.013919822 | 0 | 0 | 0 | 0 |
| *Gemella* | 0.013919822 | 0.017289073 | 0 | 0 | 0.014164306 |
| *Listeria* | 0 | 0 | 0 | 0 | 0.014164306 |
| *Staphylococcus* | 0 | 0 | 0 | 0 | 0 |
| *Enterococcus* | 0.083518931 | 0.069156293 | 0.042517007 | 0.015513497 | 0.056657224 |
| *Lactobacillus* | 0.041759465 | 0.034578147 | 0.042517007 | 0.077567484 | 0.084985836 |
| *Weissella* | 0.013919822 | 0 | 0 | 0 | 0 |
| *Lactococcus* | 0.083518931 | 0.138312586 | 0.198412698 | 0.09308098 | 0.127478754 |
| *Streptococcus* | 0.890868597 | 0.881742739 | 0.864512472 | 0.744647844 | 0.509915014 |
| *Clostridium_sensu_stricto* | 0 | 0 | 0.028344671 | 0 | 0 |
| *Mogibacterium* | 0.013919822 | 0 | 0 | 0 | 0 |
| *Anaerofustis* | 0.027839644 | 0 | 0 | 0 | 0 |
| *Eubacterium* | 1.030066815 | 0.950899032 | 0.963718821 | 1.085944772 | 1.062322946 |
| *Anaerostipes* | 0.431514477 | 0.397648686 | 0.566893424 | 0.465404902 | 0.184135977 |
| *Blautia* | 0.15311804 | 0.138312586 | 0.12755102 | 0.170648464 | 0.169971671 |
| *Clostridium_XIVa* | 1.29454343 | 1.400414938 | 1.162131519 | 1.054917778 | 1.090651558 |
| *Coprococcus* | 0.208797327 | 0.05186722 | 0.028344671 | 0 | 0 |
| *Dorea* | 2.547327394 | 2.731673582 | 2.551020408 | 2.171889544 | 1.756373938 |
| *Hespellia* | 0.918708241 | 0.31120332 | 0.623582766 | 0.62053987 | 0.481586402 |
| *Lachnospiracea_incertae_sedis* | 8.00389755 | 6.915629322 | 7.79478458 | 8.547936705 | 6.175637394 |
| *Lactonifactor* | 0 | 0 | 0 | 0 | 0 |
| *Moryella* | 0.013919822 | 0.034578147 | 0 | 0.015513497 | 0.028328612 |
| *Oribacterium* | 0 | 0 | 0 | 0 | 0 |
| *Roseburia* | 0.473273942 | 0.224757953 | 0.311791383 | 0.279242941 | 0.325779037 |
| *Syntrophococcus* | 0.013919822 | 0.05186722 | 0.028344671 | 0.04654049 | 0.028328612 |
| *Clostridium_XI* | 0.111358575 | 0.05186722 | 0.028344671 | 0.031026993 | 0.028328612 |
| *Acetanaerobacterium* | 0 | 0 | 0 | 0 | 0 |
| *Anaerofilum* | 0 | 0.017289073 | 0 | 0.031026993 | 0 |
| *Clostridium_IV* | 1.962694878 | 1.192946058 | 2.168367347 | 1.318647223 | 3.28611898 |
| *Ethanoligenens* | 0.083518931 | 0.345781466 | 0.085034014 | 0.248215948 | 0.198300283 |
| *Flavonifractor* | 0 | 0.017289073 | 0.028344671 | 0 | 0.028328612 |
| *Hydrogenoanaerobacterium* | 0.013919822 | 0 | 0 | 0.015513497 | 0 |
| *Oscillibacter* | 2.561247216 | 3.267634855 | 3.458049887 | 3.583617747 | 4.050991501 |
| *Ruminococcus* | 2.519487751 | 2.264868603 | 2.48015873 | 3.118212845 | 1.57223796 |
| *Saccharofermentans* | 0.013919822 | 0 | 0 | 0 | 0 |
| *Sporobacter* | 0.167037862 | 0.328492393 | 0.340136054 | 0.232702451 | 0.339943343 |
| *Clostridium_XVIII* | 1.002227171 | 1.642461964 | 1.218820862 | 1.349674217 | 0.637393768 |
| *Coprobacillus* | 0.013919822 | 0.172890733 | 0 | 0.108594477 | 0.028328612 |
| *Erysipelotrichaceae_incertae_sedis* | 0.083518931 | 0.121023513 | 0.042517007 | 0.077567484 | 0.056657224 |
| *Phascolarctobacterium* | 0.083518931 | 0.397648686 | 0.382653061 | 0.372323922 | 0.339943343 |
| *Dialister* | 0.013919822 | 0.017289073 | 0 | 0 | 0 |
| *Veillonella* | 0 | 0 | 0.028344671 | 0 | 0.042492918 |
| *Gemmiger* | 1.948775056 | 1.83264177 | 1.828231293 | 1.737511635 | 1.161473088 |
| *Burkholderia* | 0 | 0.017289073 | 0 | 0 | 0 |
| *Limnohabitans* | 0.361915367 | 0.916320885 | 0.283446712 | 1.085944772 | 0.439093484 |
| *Parasutterella* | 1.14142539 | 1.141078838 | 1.587301587 | 1.535836177 | 1.444759207 |
| *Bilophila* | 0.041759465 | 0.017289073 | 0.042517007 | 0 | 0 |
| *Desulfovibrio* | 0.055679287 | 0 | 0.014172336 | 0 | 0 |
| *Klebsiella* | 0.013919822 | 0 | 0 | 0 | 0 |
| *Morganella* | 0.139198218 | 0.15560166 | 0.014172336 | 0.015513497 | 0.113314448 |
| *Acinetobacter* | 0 | 0 | 0 | 0 | 0 |
| *Acholeplasma* | 0.431514477 | 0.363070539 | 0.325963719 | 0.651566863 | 0.45325779 |

TABLE 5-2

Relative abundance of each species at the genus level (%)

| Genus | Sample Relative abundance of each species at the genus level (%) | | | | |
|---|---|---|---|---|---|
| | 4-N-3 | 4-N-7 | 6-20-1 | 6-20-3 | 6-20-7 |
| *Actinomyces* | 0 | 0 | 0 | 0.014136274 | 0 |
| *Corynebacterium* | 0 | 0 | 0 | 0 | 0 |
| *Nesterenkonia* | 0 | 0.014104372 | 0 | 0 | 0 |
| *Bifidobacterium* | 0 | 0 | 0 | 0 | 0 |
| *Asaccharobacter* | 0 | 0 | 0 | 0 | 0 |
| *Atopobium* | 0 | 0.014104372 | 0 | 0 | 0 |
| *Collinsella* | 0 | 0 | 0.014577259 | 0.014136274 | 0.038441825 |
| *Eggerthella* | 0.014357502 | 0 | 0 | 0 | 0 |
| *Olsenella* | 0 | 0 | 0 | 0 | 0 |
| *Bacteroides* | 12.72074659 | 10.9167842 | 9.052478134 | 8.580718123 | 9.507944644 |
| *Barnesiella* | 1.033740129 | 0.620592384 | 0.743440233 | 0.565450947 | 0.89697591 |
| *Butyricimonas* | 0.861450108 | 0.818053597 | 0.816326531 | 0.932994063 | 1.076371092 |
| *Odoribacter* | 0.746590093 | 0.747531735 | 0.655976676 | 0.480633305 | 0.65351102 |
| *Parabacteroides* | 2.368987796 | 2.383638928 | 1.588921283 | 1.894260673 | 1.973347002 |
| *Paraprevotella* | 0.502512563 | 0.47954866 | 0.393586006 | 0.381679389 | 0.435674013 |
| *Prevotella* | 26.48959081 | 30.11283498 | 21.51603499 | 26.83064744 | 20.79702717 |
| *Alistipes* | 9.791816224 | 8.56135402 | 7.172011662 | 7.251908397 | 7.970271656 |
| *Hymenobacter* | 0.674802584 | 0.394922426 | 0.495626822 | 0.310998021 | 0.48692978 |
| *Bacillus* | 0 | 0.028208745 | 0 | 0 | 0 |
| *Gemella* | 0.014357502 | 0 | 0 | 0 | 0.012813942 |
| *Listeria* | 0 | 0 | 0.014577259 | 0 | 0.012813942 |
| *Staphylococcus* | 0 | 0 | 0 | 0.028272547 | 0 |
| *Enterococcus* | 0 | 0.028208745 | 0 | 0.056545095 | 0.089697591 |
| *Lactobacillus* | 0.043072505 | 0.042313117 | 0.218658892 | 0 | 0.192209124 |
| *Weissella* | 0 | 0 | 0.043731778 | 0.014136274 | 0 |
| *Lactococcus* | 0.071787509 | 0.098730606 | 0.043731778 | 0.127226463 | 0.140953357 |
| *Streptococcus* | 0.875807609 | 1.325811001 | 0.728862974 | 1.003675431 | 0.781650436 |
| *Clostridium_sensu_stricto* | 0 | 0.014104372 | 0 | 0.028272547 | 0.012813942 |
| *Mogibacterium* | 0 | 0 | 0 | 0 | 0 |
| *Anaerofustis* | 0 | 0.042313117 | 0 | 0 | 0 |
| *Eubacterium* | 0.847092606 | 0.874471086 | 1.180758017 | 0.749222505 | 1.230138391 |
| *Anaerostipes* | 0.15793252 | 0.451339915 | 0.655976676 | 0.353406842 | 0.333162481 |
| *Blautia* | 0.143575018 | 0.141043724 | 0.29154519 | 0.212044105 | 0.102511533 |
| *Clostridium_XIVa* | 1.076812635 | 1.466854725 | 1.457725948 | 1.38535482 | 0.922603793 |
| *Coprococcus* | 0.143575018 | 0.070521862 | 0 | 0 | 0.197907831 |
| *Dorea* | 1.852117732 | 2.327221439 | 3.032069971 | 3.039298841 | 2.242439774 |
| *Hespellia* | 0.344580043 | 0.451339915 | 0.991253644 | 0.720949958 | 0.627883137 |
| *Lachnospiracea*_incertae_sedis | 5.857860732 | 6.318758815 | 9.081632653 | 7.364998586 | 7.239876986 |
| *Lactonifactor* | 0 | 0 | 0.029154519 | 0 | 0 |
| *Moryella* | 0 | 0 | 0 | 0 | 0 |
| *Oribacterium* | 0 | 0 | 0 | 0 | 0 |
| *Roseburia* | 0.330222541 | 0.394922426 | 0.218658892 | 0.254452926 | 0.230650948 |
| *Syntrophococcus* | 0.028715004 | 0.028208745 | 0.043731778 | 0.042408821 | 0.038441825 |
| *Clostridium_XI* | 0.043072505 | 0.084626234 | 0.087463557 | 0.070681368 | 0.051255766 |
| *Acetanaerobacterium* | 0.043072505 | 0 | 0 | 0 | 0 |
| *Anaerofilum* | 0.028715004 | 0.042313117 | 0.029154519 | 0.014136274 | 0.025627883 |
| *Clostridium_IV* | 1.378320172 | 0.902679831 | 2.128279883 | 1.964942041 | 2.844695028 |
| *Ethanoligenens* | 0.201005025 | 0.253878702 | 0 | 0.197907831 | 0.16658124 |
| *Flavonifractor* | 0 | 0 | 0.014577259 | 0 | 0 |
| *Hydrogenoanaerobacterium* | 0 | 0 | 0 | 0 | 0 |
| *Oscillibacter* | 3.718592965 | 3.427362482 | 2.49271137 | 2.403166525 | 2.960020502 |
| *Ruminococcus* | 2.469490309 | 2.468265162 | 3.06122449 | 3.604749788 | 2.690927729 |
| *Saccharofermentans* | 0 | 0 | 0 | 0 | 0 |
| *Sporobacter* | 0.387652548 | 0.409026798 | 0.451895044 | 0.183771558 | 0.256278831 |
| *Clostridium_XVIII* | 1.033740129 | 1.523272214 | 1.807580175 | 1.554990105 | 1.358277806 |
| *Coprobacillus* | 0.014357502 | 0.155148096 | 0.043731778 | 0.042408821 | 0.012813942 |
| *Erysipelotrichaceae*_incertae_sedis | 0.071787509 | 0.112834979 | 0.058309038 | 0.070681368 | 0.115325474 |
| *Phascolarctobacterium* | 0.373295047 | 0.253878702 | 0.233236152 | 0.296861747 | 0.333162481 |
| *Dialister* | 0.014357502 | 0.028208745 | 0.014577259 | 0.028272547 | 0 |
| *Veillonella* | 0.014357502 | 0.028208745 | 0.014577259 | 0 | 0.012813942 |
| *Gemmiger* | 1.335247667 | 1.664315938 | 2.157434402 | 2.120441052 | 1.806765761 |
| *Burkholderia* | 0 | 0 | 0 | 0 | 0 |
| *Limnohabitans* | 0.488155061 | 1.057827927 | 0.583090379 | 0.947130336 | 0.550999487 |
| *Parasutterella* | 1.751615219 | 1.466854725 | 0.903790087 | 1.342945999 | 0.884161968 |
| *Bilophila* | 0.014357502 | 0 | 0.014577259 | 0 | 0 |
| *Desulfovibrio* | 0.014357502 | 0 | 0.014577259 | 0.028272547 | 0 |
| *Klebsiella* | 0 | 0 | 0.014577259 | 0 | 0 |
| *Morganella* | 0 | 0.112834979 | 0 | 0.098953916 | 0.064069708 |
| *Acinetobacter* | 0 | 0 | 0 | 0.014136274 | 0 |
| *Acholeplasma* | 0.315865039 | 0.296191819 | 0.56851312 | 0.395815663 | 1.050743209 |

TABLE 5-2-continued

Relative abundance of each species at the genus level (%)

| Genus | Sample Relative abundance of each species at the genus level (%) | | | | |
|---|---|---|---|---|---|
| | 6-4-1 | 6-4-3 | 6-4-7 | 6-N-1 | 6-N-3 |
| *Actinomyces* | 0 | 0.014098407 | 0.013540961 | 0 | 0 |
| *Corynebacterium* | 0 | 0 | 0 | 0 | 0 |
| *Nesterenkonia* | 0 | 0 | 0 | 0 | 0 |
| *Bifidobacterium* | 0 | 0 | 0 | 0 | 0 |
| *Asaccharobacter* | 0 | 0 | 0 | 0 | 0 |
| *Atopobium* | 0 | 0 | 0 | 0 | 0 |
| *Collinsella* | 0.026514649 | 0.042295221 | 0.013540961 | 0.030590395 | 0.045969966 |
| *Eggerthella* | 0.013257325 | 0 | 0 | 0 | 0 |
| *Olsenella* | 0 | 0 | 0 | 0 | 0 |
| *Bacteroides* | 9.969508153 | 8.148879177 | 8.246445498 | 9.207708779 | 9.393196445 |
| *Barnesiella* | 0.59657961 | 0.761313972 | 0.636425186 | 0.718874273 | 0.781489427 |
| *Butyricimonas* | 0.981042026 | 0.690821937 | 0.812457684 | 1.070663812 | 1.02666258 |
| *Odoribacter* | 0.530292987 | 0.592133089 | 0.419769804 | 0.489446314 | 0.827459393 |
| *Parabacteroides* | 1.630650935 | 1.325250247 | 1.408259986 | 1.59070052 | 1.930738584 |
| *Paraprevotella* | 0.304918467 | 0.296066544 | 0.243737305 | 0.367084735 | 0.337113086 |
| *Prevotella* | 21.72875514 | 21.41548005 | 21.58429248 | 23.03456715 | 24.05761569 |
| *Alistipes* | 8.763091608 | 8.092485549 | 7.474610697 | 9.008871214 | 8.25927061 |
| *Hymenobacter* | 0.318175792 | 0.338361765 | 0.311442112 | 0.367084735 | 0.36775973 |
| *Bacillus* | 0 | 0 | 0 | 0 | 0 |
| *Gemella* | 0.013257325 | 0 | 0 | 0.030590395 | 0 |
| *Listeria* | 0.013257325 | 0.014098407 | 0 | 0 | 0.015323322 |
| *Staphylococcus* | 0 | 0 | 0 | 0 | 0.030646644 |
| *Enterococcus* | 0.106058597 | 0.056393628 | 0.121868653 | 0.061180789 | 0.091939933 |
| Lactobacillus | 0.145830571 | 0.098688848 | 0.09478673 | 0.045885592 | 0.07661661 |
| *Weissella* | 0.013257325 | 0 | 0 | 0 | 0.015323322 |
| *Lactococcus* | 0.251889169 | 0.155082476 | 0.081245768 | 0.030590395 | 0.183879865 |
| *Streptococcus* | 0.82195413 | 0.944593261 | 0.798916723 | 0.978892628 | 0.95004597 |
| *Clostridium_sensu_stricto* | 0.026514649 | 0 | 0.013540961 | 0 | 0 |
| *Mogibacterium* | 0 | 0 | 0 | 0 | 0 |
| *Anaerofustis* | 0.039771974 | 0 | 0 | 0 | 0 |
| *Eubacterium* | 1.007556675 | 0.944593261 | 1.002031144 | 1.040073417 | 1.195219124 |
| *Anaerostipes* | 0.464006364 | 0.67672353 | 0.67704807 | 0.412970327 | 0.490346307 |
| *Blautia* | 0.225374519 | 0.281968138 | 0.338524035 | 0.183542368 | 0.091939933 |
| *Clostridium_XIVa* | 1.352247117 | 1.522627943 | 1.530128639 | 1.98837565 | 1.087955869 |
| *Coprococcus* | 0.013257325 | 0.014098407 | 0.135409614 | 0.076475987 | 0.030646644 |
| *Dorea* | 2.651464934 | 3.482306499 | 3.344617468 | 2.906087489 | 3.018694453 |
| *Hespellia* | 1.073843298 | 1.043282109 | 1.069735951 | 0.856531049 | 0.95004597 |
| *Lachnospiracea_incertae_sedis* | 7.927880154 | 9.502326237 | 8.923493568 | 8.397063322 | 8.412503831 |
| *Lactonifactor* | 0 | 0 | 0.013540961 | 0 | 0.045969966 |
| *Moryella* | 0.013257325 | 0 | 0.027081923 | 0 | 0 |
| *Oribacterium* | 0 | 0 | 0 | 0 | 0 |
| *Roseburia* | 0.265146493 | 0.22557451 | 0.487474611 | 0.260018354 | 0.260496476 |
| *Syntrophococcus* | 0.066286623 | 0.084590441 | 0 | 0.061180789 | 0.045969966 |
| *Clostridium_XI* | 0.092801273 | 0.028196814 | 0.081245768 | 0.015295197 | 0.07661661 |
| *Acetanaerobacterium* | 0 | 0 | 0 | 0 | 0 |
| *Anaerofilum* | 0.013257325 | 0.014098407 | 0.013540961 | 0.030590395 | 0.030646644 |
| *Clostridium_IV* | 1.988598701 | 1.494431129 | 2.450914015 | 1.345977363 | 1.578302176 |
| *Ethanoligenens* | 0.079543948 | 0.140984069 | 0.148950575 | 0.183542368 | 0.199203187 |
| *Flavonifractor* | 0 | 0.014098407 | 0.027081923 | 0.030590395 | 0 |
| *Hydrogenoanaerobacterium* | 0 | 0 | 0 | 0 | 0 |
| *Oscillibacter* | 2.624950285 | 2.876075004 | 2.748815166 | 3.624961762 | 3.279190929 |
| *Ruminococcus* | 3.619249635 | 3.792471451 | 3.385240352 | 3.196696237 | 3.294514251 |
| *Saccharofermentans* | 0 | 0 | 0 | 0 | 0 |
| *Sporobacter* | 0.291661143 | 0.352460172 | 0.433310765 | 0.474151117 | 0.275819798 |
| *Clostridium_XVIII* | 1.166644571 | 1.522627943 | 1.624915369 | 1.621290795 | 1.654918786 |
| *Coprobacillus* | 0.026514649 | 0.014098407 | 0 | 0.030590395 | 0.061293288 |
| *Erysipelotrichaceae_incertae_sedis* | 0.092801273 | 0.098688848 | 0.081245768 | 0.045885592 | 0.07661661 |
| *Phascolarctobacterium* | 0.318175792 | 0.338361765 | 0.270819228 | 0.336494341 | 0.229849831 |
| *Dialister* | 0 | 0.014098407 | 0 | 0 | 0 |
| *Veillonella* | 0.066286623 | 0 | 0.013540961 | 0.045885592 | 0.030646644 |
| *Gemmiger* | 2.094657298 | 2.185253066 | 2.031144211 | 1.697766901 | 1.808152007 |
| *Burkholderia* | 0 | 0 | 0 | 0 | 0 |
| *Limnohabitans* | 0.265146493 | 0.535739461 | 0.487474611 | 0.520036708 | 0.444376341 |
| *Parasutterella* | 1.259445844 | 1.141970957 | 1.299932295 | 1.300091771 | 1.087955869 |
| *Bilophila* | 0 | 0.014098407 | 0.040622884 | 0 | 0 |
| *Desulfovibrio* | 0 | 0 | 0 | 0.015295197 | 0 |
| *Klebsiella* | 0.026514649 | 0 | 0 | 0 | 0 |
| *Morganella* | 0.119315922 | 0.042295221 | 0.067704807 | 0.107066381 | 0 |
| *Acinetobacter* | 0 | 0 | 0 | 0 | 0 |
| *Acholeplasma* | 0.517035662 | 0.521641055 | 0.379146919 | 0.39767513 | 0.505669629 |

TABLE 5-3

Relative abundance of each species at the genus level (%)

| Genus | Sample Relative abundance of each species at the genus level (%) | | | | |
|---|---|---|---|---|---|
| | 6-N-7 | N-20-1 | N-20-3 | N-20-7 | N-4-1 |
| *Actinomyces* | 0 | 0 | 0 | 0 | 0 |
| *Corynebacterium* | 0 | 0 | 0 | 0 | 0 |
| *Nesterenkonia* | 0 | 0 | 0 | 0 | 0 |
| *Bifidobacterium* | 0 | 0 | 0 | 0 | 0 |
| *Asaccharobacter* | 0 | 0 | 0 | 0.014146272 | 0 |
| *Atopobium* | 0 | 0 | 0.014467593 | 0 | 0 |
| *Collinsella* | 0.031720856 | 0.071103527 | 0.05787037 | 0.070731362 | 0.106382979 |
| *Eggerthella* | 0 | 0 | 0 | 0 | 0.015197568 |
| *Olsenella* | 0 | 0 | 0 | 0 | 0 |
| *Bacteroides* | 8.929421094 | 7.608077361 | 8.333333333 | 8.332154477 | 8.039513678 |
| *Barnesiella* | 0.697858842 | 0.938566553 | 0.636574074 | 0.579997171 | 0.790273556 |
| *Butyricimonas* | 1.07850912 | 0.42662116 | 0.506365741 | 0.452680719 | 0.592705167 |
| *Odoribacter* | 0.666137986 | 0.355517634 | 0.390625 | 0.240486632 | 0.288753799 |
| *Parabacteroides* | 1.538461538 | 1.8629124 | 1.331018519 | 1.428773518 | 1.778115502 |
| *Paraprevotella* | 0.380650278 | 0.383959044 | 0.245949074 | 0.424388174 | 0.349544073 |
| *Prevotella* | 18.85804917 | 15.23037543 | 14.55439815 | 14.54236809 | 24.89361702 |
| *Alistipes* | 8.548770817 | 8.063139932 | 8.087384259 | 7.582402037 | 8.024316109 |
| *Hymenobacter* | 0.44409199 | 0.327076223 | 0.274884259 | 0.381949356 | 0.395136778 |
| *Bacillus* | 0 | 0 | 0 | 0 | 0 |
| *Gemella* | 0 | 0.014220705 | 0.014467593 | 0 | 0.015197568 |
| *Listeria* | 0 | 0 | 0.014467593 | 0 | 0.030395137 |
| *Staphylococcus* | 0 | 0 | 0 | 0.014146272 | 0.015197568 |
| *Enterococcus* | 0.095162569 | 0.127986348 | 0.086805556 | 0.141462725 | 0.09118541 |
| *Lactobacillus* | 0.031720856 | 0.028441411 | 0.028935185 | 0.042438817 | 0.045592705 |
| *Weissella* | 0.015860428 | 0.014220705 | 0 | 0.014146272 | 0 |
| *Lactococcus* | 0.126883426 | 0.099544937 | 0.231481481 | 0.141462725 | 0.09118541 |
| *Streptococcus* | 0.729579699 | 1.237201365 | 1.171875 | 1.584382515 | 0.911854103 |
| *Clostridium_sensu_stricto* | 0.031720856 | 0 | 0 | 0 | 0.045592705 |
| *Mogibacterium* | 0.015860428 | 0 | 0 | 0 | 0.015197568 |
| *Anaerofustis* | 0 | 0 | 0.014467593 | 0.014146272 | 0 |
| *Eubacterium* | 1.157811261 | 1.22298066 | 1.721643519 | 1.72584524 | 1.079027356 |
| *Anaerostipes* | 0.396510706 | 0.782138794 | 0.651041667 | 0.707313623 | 0.288753799 |
| *Blautia* | 0.174464711 | 0.327076223 | 0.44849537 | 0.268779177 | 0.37993921 |
| *Clostridium_XIVa* | 1.157811261 | 2.033560865 | 1.591435185 | 1.386334701 | 1.03343465 |
| *Coprococcus* | 0.079302141 | 0.042662116 | 0.028935185 | 0.014146272 | 0.045592705 |
| *Dorea* | 3.092783505 | 4.209328783 | 4.35474537 | 3.635592022 | 3.799392097 |
| *Hespellia* | 0.951625694 | 1.350967008 | 1.302083333 | 1.386334701 | 0.927051672 |
| *Lachnospiracea_incertae_sedis* | 9.246629659 | 8.603526735 | 9.722222222 | 8.699957561 | 6.094224924 |
| *Lactonifactor* | 0 | 0 | 0 | 0 | 0.045592705 |
| *Moryella* | 0 | 0.028441411 | 0.014467593 | 0 | 0 |
| *Oribacterium* | 0 | 0 | 0.014467593 | 0 | 0 |
| *Roseburia* | 0.44409199 | 0.199089875 | 0.188078704 | 0.183901542 | 0.09118541 |
| *Syntrophococcus* | 0.031720856 | 0.014220705 | 0 | 0.014146272 | 0 |
| *Clostridium_XI* | 0.079302141 | 0.042662116 | 0.028935185 | 0.014146272 | 0 |
| *Acetanaerobacterium* | 0 | 0.014220705 | 0.014467593 | 0 | 0.030395137 |
| *Anaerofilum* | 0 | 0.028441411 | 0.05787037 | 0.042438817 | 0 |
| *Clostridium_IV* | 2.299762094 | 0.938566553 | 0.911458333 | 0.9760928 | 0.987841945 |
| *Ethanoligenens* | 0.047581285 | 0.085324232 | 0.086805556 | 0.339510539 | 0.258358663 |
| *Flavonifractor* | 0.031720856 | 0.028441411 | 0.043402778 | 0.05658509 | 0.015197568 |
| *Hydrogenoanaerobacterium* | 0 | 0 | 0 | 0 | 0 |
| *Oscillibacter* | 3.425852498 | 3.213879408 | 2.965856481 | 3.437544207 | 3.221884498 |
| *Ruminococcus* | 3.013481364 | 4.877701934 | 4.730902778 | 4.08827274 | 3.419452888 |
| *Saccharofermentans* | 0 | 0 | 0.014467593 | 0 | 0 |
| *Sporobacter* | 0.586835845 | 0.327076223 | 0.419560185 | 0.396095629 | 0.273556231 |
| *Clostridium_XVIII* | 1.268834259 | 1.891353811 | 1.866319444 | 1.966331872 | 2.006079027 |
| *Coprobacillus* | 0.015860428 | 0.085324232 | 0.014467593 | 0 | 0.060790274 |
| *Erysipelotrichaceae_incertae_sedis* | 0.111022998 | 0.085324232 | 0.086805556 | 0.070731362 | 0.121580547 |
| *Phascolarctobacterium* | 0.079302141 | 0.327076223 | 0.086805556 | 0.212194087 | 0.182370821 |
| *Dialister* | 0 | 0.014220705 | 0.028935185 | 0.070731362 | 0.030395137 |
| *Veillonella* | 0.031720856 | 0.014220705 | 0.028935185 | 0.042438817 | 0.030395137 |
| *Gemmiger* | 2.283901665 | 1.806029579 | 2.907986111 | 3.352666572 | 2.553191489 |
| *Burkholderia* | 0 | 0 | 0 | 0.014146272 | 0 |
| *Limnohabitans* | 0.935765266 | 0.597269625 | 0.231481481 | 0.155608997 | 1.003039514 |
| *Parasutterella* | 1.744647105 | 0.327076223 | 0.274884259 | 0.169755269 | 0.501519757 |
| *Bilophila* | 0.015860428 | 0 | 0.014467593 | 0.014146272 | 0 |
| *Desulfovibrio* | 0 | 0 | 0 | 0 | 0 |
| *Klebsiella* | 0.015860428 | 0 | 0 | 0.028292545 | 0.015197568 |
| *Morganella* | 0.015860428 | 0.042662116 | 0.072337963 | 0 | 0.151975684 |
| *Acinetobacter* | 0 | 0 | 0 | 0 | 0 |
| *Acholeplasma* | 0.301348136 | 0.625711035 | 0.419560185 | 0.594143443 | 0.425531915 |

TABLE 5-3-continued

Relative abundance of each species at the genus level (%)

| Genus | Sample Relative abundance of each species at the genus level (%) | | | | |
|---|---|---|---|---|---|
| | N-4-3 | N-4-7 | N-N-1 | N-N-3 | N-N-7 |
| *Actinomyces* | 0 | 0.014518002 | 0 | 0.013815971 | 0 |
| *Corynebacterium* | 0 | 0 | 0 | 0 | 0.172780436 |
| *Nesterenkonia* | 0 | 0 | 0 | 0 | 0 |
| *Bifidobacterium* | 0.015792798 | 0 | 0.015865461 | 0.013815971 | 0 |
| *Asaccharobacter* | 0 | 0 | 0 | 0 | 0.026581606 |
| *Atopobium* | 0 | 0 | 0 | 0 | 0 |
| *Collinsella* | 0.078963992 | 0.116144019 | 0.095192765 | 0.248687483 | 0.505050505 |
| *Eggerthella* | 0.015792798 | 0 | 0.015865461 | 0 | 0.026581606 |
| *Olsenella* | 0 | 0 | 0 | 0 | 0 |
| *Bacteroides* | 10.75489577 | 12.36933798 | 9.138505474 | 12.3100304 | 13.72939926 |
| *Barnesiella* | 0.568540745 | 0.842044135 | 0.793273045 | 0.44211108 | 0.744284955 |
| *Butyricimonas* | 0.663297536 | 0.711382114 | 0.396636522 | 0.635534678 | 1.382243488 |
| *Odoribacter* | 0.347441567 | 0.667828107 | 0.396636522 | 0.386847195 | 0.531632111 |
| *Parabacteroides* | 1.847757423 | 2.322880372 | 2.427415516 | 3.440176844 | 3.083466241 |
| *Paraprevotella* | 0.442198358 | 0.479094077 | 0.412501983 | 0.22105554 | 0.332270069 |
| Prevotella | 11.08654454 | 13.54529617 | 3.664921466 | 0.33158331 | 0.066454014 |
| *Alistipes* | 10.91282375 | 13.67595819 | 11.96255751 | 18.00221056 | 25.79744817 |
| *Hymenobacter* | 0.489576753 | 0.319396051 | 0.317309218 | 0.497374965 | 0.558213716 |
| *Bacillus* | 0 | 0 | 0 | 0.013815971 | 0 |
| *Gemella* | 0 | 0 | 0 | 0 | 0.013290803 |
| *Listeria* | 0 | 0.014518002 | 0 | 0 | 0.013290803 |
| *Staphylococcus* | 0 | 0 | 0 | 0 | 0.026581606 |
| *Enterococcus* | 0.126342388 | 0.232288037 | 0.206250992 | 0.262503454 | 0.757575758 |
| *Lactobacillus* | 0.047378395 | 0.043554007 | 0.015865461 | 0.027631943 | 0.053163211 |
| *Weissella* | 0.015792798 | 0.014518002 | 0 | 0.027631943 | 0.013290803 |
| *Lactococcus* | 0.157927985 | 0.203252033 | 0.237981913 | 0.359215253 | 0.372142477 |
| *Streptococcus* | 1.421351864 | 1.393728223 | 1.475487863 | 1.602652666 | 1.302498671 |
| *Clostridium_sensu_stricto* | 0.015792798 | 0.014518002 | 0.047596383 | 0.027631943 | 0.026581606 |
| *Mogibacterium* | 0 | 0 | 0 | 0.013815971 | 0 |
| *Anaerofustis* | 0.015792798 | 0.014518002 | 0.031730922 | 0.041447914 | 0.013290803 |
| *Eubacterium* | 1.500315856 | 1.292102207 | 1.697604315 | 1.160541586 | 0.345560872 |
| *Anaerostipes* | 0.773847126 | 0.464576074 | 1.126447723 | 1.257253385 | 1.315789474 |
| *Blautia* | 0.426405559 | 0.304878049 | 0.428367444 | 0.165791655 | 0.398724083 |
| *Clostridium_XIVa* | 1.531901453 | 1.175958188 | 1.586546089 | 1.616468638 | 0.637958533 |
| *Coprococcus* | 0 | 0 | 0 | 0 | 0.013290803 |
| *Dorea* | 4.737839545 | 1.959930314 | 5.727431382 | 4.614534402 | 0.531632111 |
| *Hespellia* | 1.500315856 | 1.350174216 | 1.792797081 | 0.939486046 | 0.571504519 |
| *Lachnospiracea*_incertae_sedis | 6.554011371 | 4.849012776 | 4.934158337 | 2.790826195 | 2.618288145 |
| *Lactonifactor* | 0.015792798 | 0.014518002 | 0 | 0.013815971 | 0.013290803 |
| *Moryella* | 0 | 0.014518002 | 0.015865461 | 0.027631943 | 0.013290803 |
| *Oribacterium* | 0 | 0 | 0 | 0 | 0 |
| *Roseburia* | 0.063171194 | 0.130662021 | 0.126923687 | 0.027631943 | 0.079744817 |
| *Syntrophococcus* | 0.031585597 | 0.043554007 | 0.047596383 | 0.041447914 | 0 |
| *Clostridium_XI* | 0.063171194 | 0.072590012 | 0.126923687 | 0.096711799 | 0.252525253 |
| *Acetanaerobacterium* | 0 | 0 | 0 | 0 | 0 |
| *Anaerofilum* | 0 | 0.101626016 | 0 | 0.013815971 | 0 |
| *Clostridium_IV* | 0.979153506 | 1.234030197 | 0.983658575 | 0.953302017 | 0.704412547 |
| *Ethanoligenens* | 0.110549589 | 0.43554007 | 0.333174679 | 0.44211108 | 0.438596491 |
| *Flavonifractor* | 0.015792798 | 0 | 0 | 0.027631943 | 0 |
| *Hydrogenoanaerobacterium* | 0 | 0 | 0 | 0 | 0 |
| *Oscillibacter* | 2.984838913 | 3.469802555 | 3.300015865 | 2.279635258 | 2.777777778 |
| *Ruminococcus* | 4.848389135 | 5.153890825 | 5.362525781 | 4.849405913 | 4.452418926 |
| *Saccharofermentans* | 0 | 0 | 0 | 0 | 0 |
| *Sporobacter* | 0.473783955 | 0.638792102 | 0.682214818 | 0.511190937 | 0.398724083 |
| *Clostridium_XVIII* | 2.368919773 | 2.308362369 | 3.093764874 | 4.089527494 | 2.684742158 |
| *Coprobacillus* | 0.078963992 | 0.043554007 | 0.111058226 | 0.165791655 | 0.132908028 |
| *Erysipelotrichaceae*_incertae_sedis | 0.063171194 | 0.101626016 | 0.079327304 | 0.055263885 | 0.039872408 |
| *Phascolarctobacterium* | 0.284270373 | 0.275842044 | 0.269712835 | 0.33158331 | 0.611376927 |
| *Dialister* | 0 | 0.014518002 | 0.031730922 | 0 | 0.053163211 |
| *Veillonella* | 0.015792798 | 0.029036005 | 0.031730922 | 0.027631943 | 0.053163211 |
| *Gemmiger* | 3.33228048 | 3.106852497 | 4.029827066 | 5.705996132 | 4.359383307 |
| *Burkholderia* | 0 | 0 | 0 | 0 | 0 |
| *Limnohabitans* | 0.347441567 | 0.682346109 | 0.269712835 | 0.262503454 | 0.225943647 |
| *Parasutterella* | 0.20530638 | 0.217770035 | 0.222116452 | 0.151975684 | 0.119617225 |
| *Bilophila* | 0.031585597 | 0 | 0 | 0 | 0 |
| *Desulfovibrio* | 0 | 0 | 0 | 0.013815971 | 0 |
| *Klebsiella* | 0.015792798 | 0 | 0.031730922 | 0.013815971 | 0.013290803 |
| *Morganella* | 0.126342388 | 0.116144019 | 0 | 0.234871511 | 0 |
| *Acinetobacter* | 0 | 0 | 0 | 0.013815971 | 0 |
| *Acholeplasma* | 0.568540745 | 0.638792102 | 0.761542123 | 0.898038132 | 0.744284955 |

TABLE 6-1

Correlation between each two samples at the genus level

| Sample | Correlation coefficient between each two samples | | | | | | | | | |
|---|---|---|---|---|---|---|---|---|---|---|
| | Control 1 | Control 2 | Control 3 | 4-20-1 | 4-20-3 | 4-20-7 | 4-4-1 | 4-4-3 | 4-4-7 | 4-N-1 |
| Control 1 | 1 | 0.973984941 | 0.960542972 | 0.987659812 | 0.993132183 | 0.987397022 | 0.967425431 | 0.961651558 | 0.960488587 | 0.990578339 |
| Control 2 | 0.973984941 | 1 | 0.996836026 | 0.980134895 | 0.971052433 | 0.977602414 | 0.961682985 | 0.964454069 | 0.974715549 | 0.954079304 |
| Control 3 | 0.960542972 | 0.996836026 | 1 | 0.969642449 | 0.956599998 | 0.966579556 | 0.954783384 | 0.95872449 | 0.972046958 | 0.934723123 |
| 4-20-1 | 0.987659812 | 0.980134895 | 0.969642449 | 1 | 0.996847161 | 0.99899208 | 0.990079838 | 0.989291635 | 0.987680756 | 0.983787671 |
| 4-20-3 | 0.993132183 | 0.971052433 | 0.956599998 | 0.996847161 | 1 | 0.997390163 | 0.982766031 | 0.980136739 | 0.974642589 | 0.992132322 |
| 4-20-7 | 0.987397022 | 0.977602414 | 0.966579556 | 0.99899208 | 0.997390163 | 1 | 0.987868678 | 0.98818658 | 0.9844335 | 0.9847508 |
| 4-4-1 | 0.967425431 | 0.961682985 | 0.954783384 | 0.990079838 | 0.982766031 | 0.987868678 | 1 | 0.99739913 | 0.992653329 | 0.962541572 |
| 4-4-3 | 0.961651558 | 0.964454069 | 0.95872449 | 0.989291635 | 0.980136739 | 0.98818658 | 0.99739913 | 1 | 0.995100096 | 0.959289538 |
| 4-4-7 | 0.960488587 | 0.974715549 | 0.972046958 | 0.987680756 | 0.974642589 | 0.9844335 | 0.992653329 | 0.995100096 | 1 | 0.953013603 |
| 4-N-1 | 0.990578339 | 0.954079304 | 0.934723123 | 0.983787671 | 0.992132322 | 0.9847508 | 0.962541572 | 0.959289538 | 0.953013603 | 1 |
| 4-N-3 | 0.986621323 | 0.955758443 | 0.942098573 | 0.992430538 | 0.995202219 | 0.992276052 | 0.987840923 | 0.983469785 | 0.975240002 | 0.988729385 |
| 4-N-7 | 0.994602 | 0.958766667 | 0.941874169 | 0.987714125 | 0.995146584 | 0.988119174 | 0.968906313 | 0.962037356 | 0.956365656 | 0.994183799 |
| 6-20-1 | 0.982108933 | 0.988820898 | 0.97975421 | 0.99418942 | 0.990178235 | 0.994958081 | 0.976377178 | 0.979218386 | 0.980547002 | 0.974744375 |
| 6-20-3 | 0.994620547 | 0.974177969 | 0.959587974 | 0.988146425 | 0.99367934 | 0.989160589 | 0.961539737 | 0.958485737 | 0.957015059 | 0.990066047 |
| 6-20-7 | 0.984778733 | 0.979797204 | 0.96929847 | 0.996723061 | 0.994380374 | 0.997541231 | 0.987083496 | 0.988699058 | 0.98640938 | 0.984075393 |
| 6-4-1 | 0.986166752 | 0.985458943 | 0.977081333 | 0.998164136 | 0.994239545 | 0.997750012 | 0.987808746 | 0.989407768 | 0.988742011 | 0.978876099 |
| 6-4-3 | 0.981509838 | 0.995220679 | 0.989109592 | 0.991377248 | 0.984984539 | 0.990291353 | 0.97227143 | 0.975218328 | 0.981452327 | 0.969141245 |
| 6-4-7 | 0.983428846 | 0.991488101 | 0.982621235 | 0.992741279 | 0.98903879 | 0.99291246 | 0.972208828 | 0.975694051 | 0.978158377 | 0.976267256 |
| 6-N-1 | 0.989343405 | 0.988962969 | 0.97969869 | 0.997578703 | 0.993798223 | 0.995618362 | 0.983371684 | 0.983083228 | 0.985552795 | 0.982433559 |
| 6-N-3 | 0.991904784 | 0.986384315 | 0.976123548 | 0.99695967 | 0.995825385 | 0.996921856 | 0.979859951 | 0.979605988 | 0.980479999 | 0.985596156 |
| 6-N-7 | 0.96766511 | 0.988362408 | 0.984622922 | 0.990025729 | 0.978897088 | 0.988472073 | 0.981503234 | 0.987294538 | 0.99231302 | 0.960561377 |
| N-20-1 | 0.94321115 | 0.988251806 | 0.993286206 | 0.964325407 | 0.94747523 | 0.960724729 | 0.960645774 | 0.96546251 | 0.97748234 | 0.916356722 |
| N-20-3 | 0.923125496 | 0.978950985 | 0.987079165 | 0.951811977 | 0.930940421 | 0.948760085 | 0.950823125 | 0.958713755 | 0.970500391 | 0.893155773 |
| N-20-7 | 0.936384338 | 0.982904545 | 0.988400511 | 0.961386333 | 0.942722262 | 0.958810878 | 0.961087532 | 0.967676962 | 0.976376501 | 0.908930341 |
| N-4-1 | 0.997855715 | 0.978185325 | 0.96615507 | 0.987006035 | 0.991418172 | 0.986536903 | 0.966585312 | 0.960616293 | 0.960467488 | 0.987025833 |
| N-4-3 | 0.853585003 | 0.907125303 | 0.921186123 | 0.893612646 | 0.867558557 | 0.887437479 | 0.929568021 | 0.933260452 | 0.937517851 | 0.81839318 |
| N-4-7 | 0.87090588 | 0.892719855 | 0.898272439 | 0.903172708 | 0.883580372 | 0.896140824 | 0.943704655 | 0.942661989 | 0.943970694 | 0.847276444 |
| N-N-1 | 0.597618821 | 0.693804615 | 0.725873038 | 0.651631112 | 0.610211436 | 0.640589687 | 0.720625923 | 0.726772715 | 0.738026211 | 0.544634641 |
| N-N-3 | 0.421834007 | 0.497416256 | 0.526523182 | 0.48286985 | 0.440623616 | 0.469072896 | 0.578922829 | 0.578841426 | 0.584037462 | 0.375839697 |
| N-N-7 | 0.39466287 | 0.449085066 | 0.47086012 | 0.454610315 | 0.413824735 | 0.438102359 | 0.550982718 | 0.550475303 | 0.560732521 | 0.365102083 |

TABLE 6-2

Correlation between each two samples at the genus level

| Sample | Correlation coefficient between each two samples | | | | | | | | | |
|---|---|---|---|---|---|---|---|---|---|---|
| | 4-N-3 | 4-N-7 | 6-20-1 | 6-20-3 | 6-20-7 | 6-4-1 | 6-4-3 | 6-4-7 | 6-N-1 | 6-N-3 |
| Control 1 | 0.986621323 | 0.994602 | 0.982108933 | 0.994620547 | 0.984778733 | 0.986166752 | 0.981509838 | 0.983428846 | 0.989343405 | 0.991904784 |
| Control 2 | 0.955758443 | 0.958766667 | 0.988820898 | 0.974177969 | 0.979797204 | 0.985458943 | 0.995220679 | 0.991488101 | 0.988962969 | 0.986384315 |
| Control 3 | 0.942098573 | 0.941874169 | 0.97975421 | 0.959587974 | 0.96929847 | 0.977081333 | 0.989109592 | 0.982621235 | 0.97969869 | 0.976123548 |
| 4-20-1 | 0.992430538 | 0.987714125 | 0.99418942 | 0.988146425 | 0.996723061 | 0.998164136 | 0.991377248 | 0.992741279 | 0.997578703 | 0.99695967 |
| 4-20-3 | 0.995202219 | 0.995146584 | 0.990178235 | 0.99367934 | 0.994380374 | 0.994239545 | 0.984984539 | 0.98903879 | 0.993798223 | 0.995825385 |
| 4-20-7 | 0.992276052 | 0.988119174 | 0.994958081 | 0.989160589 | 0.997541231 | 0.997750012 | 0.990291353 | 0.99291246 | 0.995618362 | 0.996921856 |
| 4-4-1 | 0.987840923 | 0.968906313 | 0.976377178 | 0.961539737 | 0.987083496 | 0.987808746 | 0.97227143 | 0.972208828 | 0.983371684 | 0.979859951 |
| 4-4-3 | 0.983469785 | 0.962037356 | 0.979218386 | 0.958485737 | 0.988699058 | 0.989407768 | 0.975218328 | 0.975694051 | 0.983083228 | 0.979605988 |
| 4-4-7 | 0.975240002 | 0.956365656 | 0.980547002 | 0.957015059 | 0.98640938 | 0.988742011 | 0.981452327 | 0.978158377 | 0.985552795 | 0.980479999 |
| 4-N-1 | 0.988729385 | 0.994183799 | 0.974744375 | 0.990066047 | 0.984075393 | 0.978876099 | 0.969141245 | 0.976267256 | 0.982433559 | 0.985596156 |

TABLE 6-2-continued

Correlation between each two samples at the genus level

| Sample | Correlation coefficient between each two samples | | | | | | | | | |
|---|---|---|---|---|---|---|---|---|---|---|
| | 4-N-3 | 4-N-7 | 6-20-1 | 6-20-3 | 6-20-7 | 6-4-1 | 6-4-3 | 6-4-7 | 6-N-1 | 6-N-3 |
| 4-N-3 | 1 | 0.992523622 | 0.977741611 | 0.982716038 | 0.989565229 | 0.98786859 | 0.971463977 | 0.975410585 | 0.986525522 | 0.987465003 |
| 4-N-7 | 0.992523622 | 1 | 0.978855199 | 0.994343763 | 0.983615327 | 0.98202144 | 0.973419875 | 0.978173685 | 0.985688237 | 0.989423703 |
| 6-20-1 | 0.977741611 | 0.978855199 | 1 | 0.988471917 | 0.994356803 | 0.995565181 | 0.997253083 | 0.998640699 | 0.995344182 | 0.99681254 |
| 6-20-3 | 0.982716038 | 0.994343763 | 0.988471917 | 1 | 0.98657215 | 0.986704842 | 0.98551879 | 0.989828659 | 0.989505832 | 0.99399354 |
| 6-20-7 | 0.989565229 | 0.983615327 | 0.994356803 | 0.98657215 | 1 | 0.997224701 | 0.989689602 | 0.992865881 | 0.994681985 | 0.995827339 |
| 6-4-1 | 0.98786859 | 0.98202144 | 0.995565181 | 0.986704842 | 0.997224701 | 1 | 0.994184347 | 0.995022505 | 0.997070802 | 0.996660577 |
| 6-4-3 | 0.971463977 | 0.973419875 | 0.997253083 | 0.98551879 | 0.989689602 | 0.994184347 | 1 | 0.998365625 | 0.995913765 | 0.995328686 |
| 6-4-7 | 0.975410585 | 0.978173685 | 0.998640699 | 0.989828659 | 0.992865881 | 0.995022505 | 0.998365625 | 1 | 0.995977922 | 0.996642986 |
| 6-N-1 | 0.986525522 | 0.985688237 | 0.995344182 | 0.989505832 | 0.994681985 | 0.997070802 | 0.995913765 | 0.995977922 | 1 | 0.998230241 |
| 6-N-3 | 0.987465003 | 0.989423703 | 0.99681254 | 0.99399354 | 0.995827339 | 0.996660577 | 0.995328686 | 0.996642986 | 0.998230241 | 1 |
| 6-N-7 | 0.970236253 | 0.9613547 | 0.992566736 | 0.970957719 | 0.990295249 | 0.99283726 | 0.993784342 | 0.992755859 | 0.991607754 | 0.988710356 |
| N-20-1 | 0.93605478 | 0.926069198 | 0.972538241 | 0.942119207 | 0.963753415 | 0.972682556 | 0.980949757 | 0.973512332 | 0.972237968 | 0.966245126 |
| N-20-3 | 0.917463965 | 0.903643565 | 0.963313353 | 0.922538974 | 0.951216196 | 0.96185225 | 0.971210066 | 0.962521184 | 0.958062819 | 0.95208329 |
| N-20-7 | 0.932533591 | 0.919227426 | 0.970032061 | 0.933585738 | 0.961903248 | 0.969675607 | 0.975445178 | 0.968360577 | 0.966232699 | 0.961225743 |
| N-4-1 | 0.983274321 | 0.992754447 | 0.984853077 | 0.995711828 | 0.984947061 | 0.985749273 | 0.984401018 | 0.986415845 | 0.989961474 | 0.992911501 |
| N-4-3 | 0.871845098 | 0.831169198 | 0.887031785 | 0.836663127 | 0.893578329 | 0.905390606 | 0.894625657 | 0.883938106 | 0.892060801 | 0.879488312 |
| N-4-7 | 0.899434368 | 0.854463303 | 0.881149965 | 0.846253273 | 0.903517671 | 0.910912601 | 0.885574273 | 0.877591515 | 0.896594101 | 0.884016135 |
| N-N-1 | 0.622146816 | 0.558621842 | 0.643193867 | 0.566998788 | 0.655168728 | 0.672100815 | 0.660786904 | 0.642061236 | 0.653282868 | 0.631088876 |
| N-N-3 | 0.468517583 | 0.386842293 | 0.453241284 | 0.378373915 | 0.484129663 | 0.499345149 | 0.467798691 | 0.448866931 | 0.473383745 | 0.446363765 |
| N-N-7 | 0.449986822 | 0.362402463 | 0.409726005 | 0.342802079 | 0.453128074 | 0.466575687 | 0.426929856 | 0.40696979 | 0.442635908 | 0.412119402 |

TABLE 6-3

Correlation between each two samples at the genus level

| Sample | Correlation coefficient between each two samples | | | | | | | | | |
|---|---|---|---|---|---|---|---|---|---|---|
| | 6-N-7 | N-20-1 | N-20-3 | N-20-7 | N-4-1 | N-4-3 | N-4-7 | N-N-1 | N-N-3 | N-N-7 |
| Control 1 | 0.96766511 | 0.94321115 | 0.923125496 | 0.936384338 | 0.997855715 | 0.853585003 | 0.87090588 | 0.597618821 | 0.421834007 | 0.39466287 |
| Control 2 | 0.988362408 | 0.988251806 | 0.978950985 | 0.982904545 | 0.978185325 | 0.907125303 | 0.892719855 | 0.693804615 | 0.497416256 | 0.449085066 |
| Control 3 | 0.984622922 | 0.993286206 | 0.987079165 | 0.988400511 | 0.96615507 | 0.921186123 | 0.898272439 | 0.725873038 | 0.526523182 | 0.47086012 |
| 4-20-1 | 0.990025729 | 0.964325407 | 0.951811977 | 0.961386333 | 0.987006035 | 0.893612646 | 0.903172708 | 0.651631112 | 0.48286985 | 0.454610315 |
| 4-20-3 | 0.978897088 | 0.94747523 | 0.930940421 | 0.942722262 | 0.991418172 | 0.867558557 | 0.883580372 | 0.610211436 | 0.440623616 | 0.413824735 |
| 4-20-7 | 0.988472073 | 0.960724729 | 0.948760085 | 0.958810878 | 0.986536903 | 0.887437479 | 0.896140824 | 0.640589687 | 0.469072896 | 0.438102359 |
| 4-4-1 | 0.981503234 | 0.960645774 | 0.950823125 | 0.961087532 | 0.966585312 | 0.929568021 | 0.943704655 | 0.720625923 | 0.578922829 | 0.550982718 |
| 4-4-3 | 0.987294538 | 0.96546251 | 0.958713755 | 0.967676962 | 0.960616293 | 0.933260452 | 0.942661989 | 0.726772715 | 0.578841426 | 0.550475303 |
| 4-4-7 | 0.99231302 | 0.97748234 | 0.970500391 | 0.976376501 | 0.960467488 | 0.937517851 | 0.943970694 | 0.738026211 | 0.584037462 | 0.560732521 |
| 4-N-1 | 0.960561377 | 0.916356722 | 0.893155773 | 0.908930341 | 0.987025833 | 0.81839318 | 0.847276444 | 0.544634641 | 0.375839697 | 0.365102083 |
| 4-N-3 | 0.970236253 | 0.93605478 | 0.917463965 | 0.932533591 | 0.983274321 | 0.871845098 | 0.899434368 | 0.622146816 | 0.468517583 | 0.449986822 |
| 4-N-7 | 0.9613547 | 0.926069198 | 0.903643565 | 0.919227426 | 0.992754447 | 0.831169198 | 0.854463303 | 0.558621842 | 0.386842293 | 0.362402463 |
| 6-20-1 | 0.992566736 | 0.972538241 | 0.963313353 | 0.970032061 | 0.984853077 | 0.887031785 | 0.881149965 | 0.643193867 | 0.453241284 | 0.409726005 |
| 6-20-3 | 0.970957719 | 0.942119207 | 0.922538974 | 0.933585738 | 0.995711828 | 0.836663127 | 0.846253273 | 0.566998788 | 0.378373915 | 0.342802079 |
| 6-20-7 | 0.990295249 | 0.963753415 | 0.951216196 | 0.961903248 | 0.984947061 | 0.893578329 | 0.903517671 | 0.655168728 | 0.484129663 | 0.453128074 |
| 6-4-1 | 0.99283726 | 0.972682556 | 0.96185225 | 0.969675607 | 0.985749273 | 0.905390606 | 0.910912601 | 0.672100815 | 0.499345149 | 0.466575687 |
| 6-4-3 | 0.993784342 | 0.980949757 | 0.971210066 | 0.975445178 | 0.984401018 | 0.894625657 | 0.885574273 | 0.660786904 | 0.467798691 | 0.426929856 |
| 6-4-7 | 0.992755859 | 0.973512332 | 0.962521184 | 0.968360577 | 0.986415845 | 0.883938106 | 0.877591515 | 0.642061236 | 0.448866931 | 0.40696979 |
| 6-N-1 | 0.991607754 | 0.972237968 | 0.958062819 | 0.966232699 | 0.989961474 | 0.892060801 | 0.896594101 | 0.653282868 | 0.473383745 | 0.442635908 |
| 6-N-3 | 0.988710356 | 0.966245126 | 0.95208329 | 0.961225743 | 0.992911501 | 0.879488312 | 0.884016135 | 0.631088876 | 0.446363765 | 0.412119402 |
| 6-N-7 | 1 | 0.982248623 | 0.977123774 | 0.981507589 | 0.970546125 | 0.918635935 | 0.911179955 | 0.704064568 | 0.524662441 | 0.487382147 |
| N-20-1 | 0.982248623 | 1 | 0.994708795 | 0.993010639 | 0.94965498 | 0.949366585 | 0.92363161 | 0.775404381 | 0.586360806 | 0.528135896 |

TABLE 6-3-continued

Correlation between each two samples at the genus level

| Sample | Correlation coefficient between each two samples | | | | | | | | | |
|---|---|---|---|---|---|---|---|---|---|---|
| | 6-N-7 | N-20-1 | N-20-3 | N-20-7 | N-4-1 | N-4-3 | N-4-7 | N-N-1 | N-N-3 | N-N-7 |
| N-20-3 | 0.977123774 | 0.994708795 | 1 | 0.99690741 | 0.930051302 | 0.957272957 | 0.92213443 | 0.795049441 | 0.608968699 | 0.54388823 |
| N-20-7 | 0.981507589 | 0.993010639 | 0.99690741 | 1 | 0.942111693 | 0.956414204 | 0.929314064 | 0.786282947 | 0.603976362 | 0.540296684 |
| N-4-1 | 0.970546125 | 0.94965498 | 0.930051302 | 0.942111693 | 1 | 0.858483134 | 0.867461542 | 0.606798381 | 0.422998607 | 0.383732336 |
| N-4-3 | 0.918635935 | 0.949366585 | 0.957272957 | 0.956414204 | 0.858483134 | 1 | 0.978865647 | 0.919493982 | 0.799540131 | 0.73699318 |
| N-4-7 | 0.911179955 | 0.92363161 | 0.92213443 | 0.929314064 | 0.867461542 | 0.978865647 | 1 | 0.880819713 | 0.795261589 | 0.773048331 |
| N-N-1 | 0.704064568 | 0.775404381 | 0.795049441 | 0.786282947 | 0.606798381 | 0.919493982 | 0.880819713 | 1 | 0.947335848 | 0.871469802 |
| N-N-3 | 0.524662441 | 0.586360806 | 0.608968699 | 0.603976362 | 0.422998607 | 0.799540131 | 0.795261589 | 0.947335848 | 1 | 0.964012364 |
| N-N-7 | 0.487382147 | 0.528135896 | 0.54388823 | 0.540296684 | 0.383732336 | 0.73699318 | 0.773048331 | 0.871469802 | 0.964012364 | 1 |

Example 3 Storage of Blood Samples

A fresh blood (whole blood) sample was collected in a centrifuge tube containing anticoagulant $K_2$-EDTA, and mixed with the stabilizer with Formulation 1.1 or Formulation 1.3 (Table 1) at a specific ratio, respectively. For example, when the ratio was 2:1, 100 μL blood and 50 μL stabilizer were added to a micro-centrifuge tube, and mixed under vortexing. For example, when the ratio was 4:1, 100 μL blood and 25 μL stabilizer were mixed under vortexing. For example, when the ratio was 8:1, 100 μL blood and 12.5 μL stabilizer were mixed under vortexing. Multiple mixed samples were prepared for each time point of detection, and stored at room temperature. 100 μL blood sample stored at room temperature was used as unprotected control sample (NP), and 100 μL blood sample stored at −80° C. was used as freezing control sample. 10 Days later, DNA was extracted by using QIAamp™ Purification Mini Kit (Qiagen, Valencia, Calif.), and detailed steps were performed according to manufacturer's instructions on blood samples. And all the experiments were performed in duplicate. Finally, the genomic DNA obtained by extraction was eluted with 100 μL eluent. After elution, 10 μL eluate was loaded into a sample well of ethidium bromide-containing 0.8% agarose gel. After electrophoresis at 120V for 40 min, photographs were taken by ultraviolet ray (UVI) imaging system. The electrophoretogram is shown in FIG. 5.

The results show that the DNA obtained from the blood sample mixed with the stabilizer at different ratios and stored at room temperature, showed a more clearly resolved band in the electrophoretogram, and the electrophoresis band was blurred and slightly smeared for the DNA obtained from the sample stored without stabilizer at room temperature.

Figure 6:
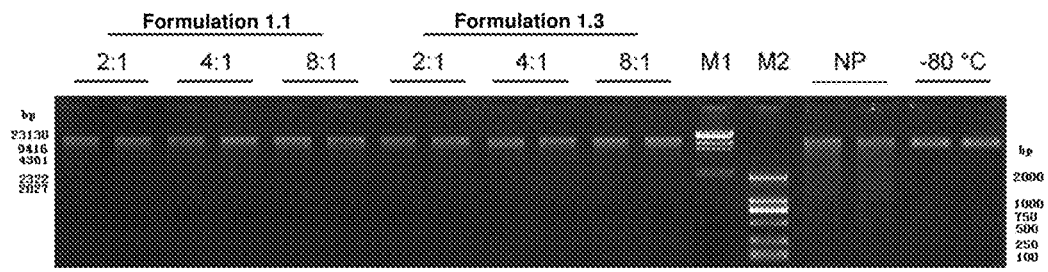
FIG. 6 shows the agarose gel electrophoretogram of the DNA extracted from the human whole blood samples stored under different conditions. The human whole blood sample was first mixed with the stabilizer with Formulation 1.1 or Formulation 1.3 at three different ratios, and then stored at room temperature; or directly stored at room temperature without stabilizer (NP); or stored at −80° C. without stabilizer. 20 days later, DNA was extracted from the sample, and was subjected to electrophoresis on 0.8% agarose gel.

Example 4 Stability of DNA in a Blood Sample Stored at Room Temperature for 20 Days A fresh blood (whole blood) sample was collected in a centrifuge tube containing anticoagulant $K_2$-EDTA, and mixed with the stabilizer with Formulation 1.1 or Formulation 1.3 (Table 1) at a specific ratio, respectively. After storage at room temperature for 20 days, DNA extraction was carried out. In addition, the sample stored without stabilizer at room temperature (NP) and the sample stored without stabilizer at −80° C. were used as control samples. The DNA extracted from all the samples was eluted with 100 μL eluent. After elution, 10 μL eluate was loaded into a sample well of ethidium bromide-containing 0.8% agarose gel. After electrophoresis at 120V for 40 min, photographs were taken by ultraviolet ray (UVI) imaging system. The electrophoretogram is shown in FIG. 6. The results show that the DNA obtained from the blood samples which were mixed with stabilizer with Formulation 1.1 or Formulation 1.3 at specific ratio respectively, and stored at room temperature for 20 days, still showed more clearly resolved bands in the electrophoretogram, while the electrophoresis bands were severely smeared for the DNA obtained from the samples stored without stabilizer, indicating severe degradation of DNA.

Figure 7:
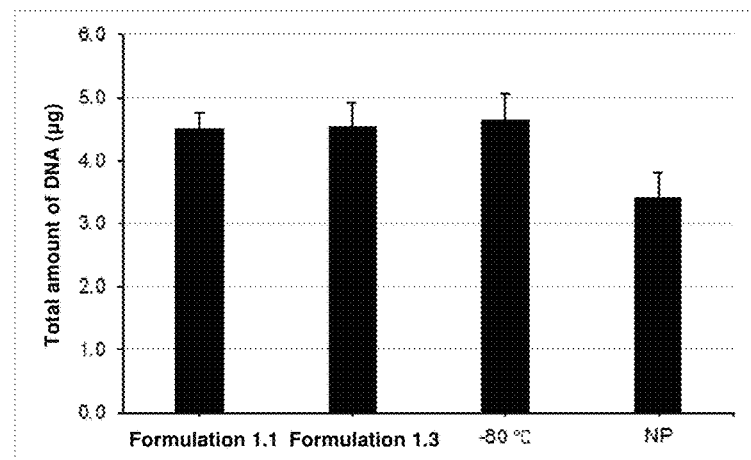
FIG. 7 shows the total amount of DNA extracted from the human whole blood samples stored under different conditions. The human whole blood sample was first mixed with the stabilizer with Formulation 1.1 or Formulation 1.3 at specific ratios, and then stored at room temperature; or directly stored at room temperature without stabilizer (NP); or stored at −80° C. without stabilizer. 20 days later, DNA was extracted from the sample, and the DNA concentration was determined by spectrophotometer.

DNA concentrations were determined from ultraviolet spectra at 260 nm by Biotek Synergy 2 Reader. The results of stored samples with stabilizer at a ratio of 4:1 were compared with that of control samples, and shown in FIG. 7 and Table 7. The results show that the total amount of DNA obtained from the samples stored with stabilizer at room temperature was comparable to the total amount of DNA obtain from the sample stored at −80° C., with no significant difference, while the total amount of DNA obtained from the sample stored without stabilizer at room temperature was significantly lower.

TABLE 7

Results of total amount of DNA

| Group | Formulation 1.1 | Formulation 1.3 | −80° C. | NP |
|---|---|---|---|---|
| Total amount of DNA (μg) | 4.52 ± 0.25 | 4.54 ± 0.37 | 4.65 ± 0.42 | 3.41 ± 0.38 |

Example 5 Stability of DNA in a Non-Cryostored Blood Sample

A fresh blood (whole blood) sample was collected in a centrifuge tube containing anticoagulant $K_2$-EDTA, and mixed with the stabilizer with Formulation 1.1 or Formulation 1.3 (Table 1) at different ratios, respectively. In addition, the sample stored without stabilizer at room temperature (NP) and the sample stored without stabilizer at −80° C. were used as control samples. A simulative transportation process was then performed, and the steps were as followed:
a) stored at room temperature for 2 days;
b) stored at 45° C. for 2 days;

c) stored at room temperature for 3 days;
d) stored at −20° C. for 2 days;
e) stored at room temperature for 3 days; and
f) stored at 45° C. for 2 days.

Figure 8:
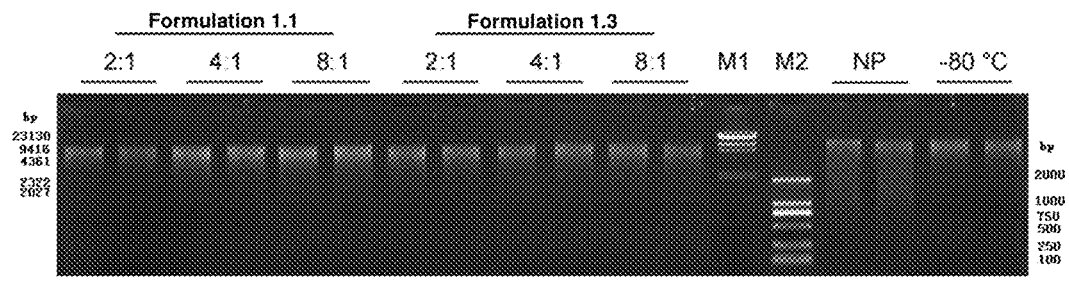
FIG. 8 shows the agarose gel electrophoretogram of the DNA extracted from the human whole blood samples stored under different conditions. The human whole blood sample was first mixed with the stabilizer with Formulation 1.1 or Formulation 1.3 at specific ratios, and then stored at room temperature for 10 days after a simulative transportation process; or stored at room temperature for 10 days after a simulative transportation process without stabilizer (NP); or stored at −80° C. without stabilizer. After the storage, DNA was extracted from the sample, and was subjected to electrophoresis on 0.8% agarose gel.
Figure 9:
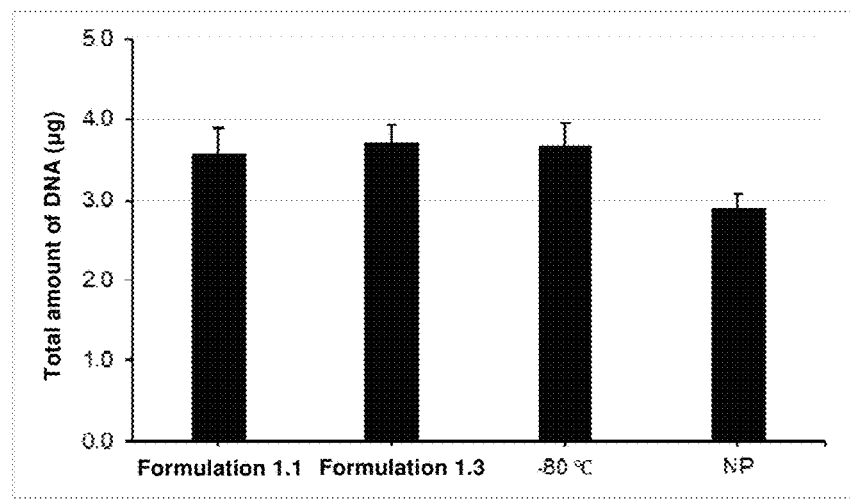
FIG. 9 shows the total amount of the DNA extracted from the human whole blood samples stored under different conditions. The human whole blood sample was first mixed with the stabilizer with Formulation 1.1 or Formulation 1.3 at specific ratios, and then stored at room temperature for 10 days after a simulative transportation process; or stored at room temperature for 10 days after a simulative transportation process without stabilizer (NP); or stored at −80° C. without stabilizer. After the storage, DNA was extracted from the sample, and the DNA concentration was determined by spectrophotometer.

After being treated with the above steps, the blood sample was further stored at room temperature for 10 days, followed by DNA extraction. The DNA from all the samples were eluted with 100 μL eluent. After elution, 10 μL eluate was loaded into a sample well of ethidium bromide-containing 0.8% agarose gel. After electrophoresis at 120V for 50 min, photographs were taken by ultraviolet ray (UVI) imaging system. The electrophoretogram is shown in FIG. 8. DNA concentrations were determined from ultraviolet spectra at 260 nm by Biotek Synergy 2 Reader. The results of stored samples with stabilizer at a ratio of 4:1 were compared with that of the control samples, and shown in FIG. 9 and Table 8.

The results show that the DNA obtained from the blood sample which was mixed with the stabilizer with Formulation 1.1 or Formulation 1.3 at different ratios respectively, and underwent a simulative transportation process, showed a more clearly resolved band in the electrophoretogram, and its total amount was comparable to the total amount of DNA obtained in the control sample stored at −80° C.; while the electrophoresis band was severely smeared for the DNA obtained from the sample stored at room temperature without stabilizer, and the total amount of DNA was also relatively lower, indicating severe degradation of DNA.

TABLE 8

Result of total amount of DNA

| Group | Formulation 1.1 | Formulation 1.3 | −80° C. | NP |
|---|---|---|---|---|
| Total amount of DNA (μg) | 3.57 ± 0.32 | 3.72 ± 0.22 | 3.68 ± 0.29 | 2.90 ± 0.19 |

Figure 10:
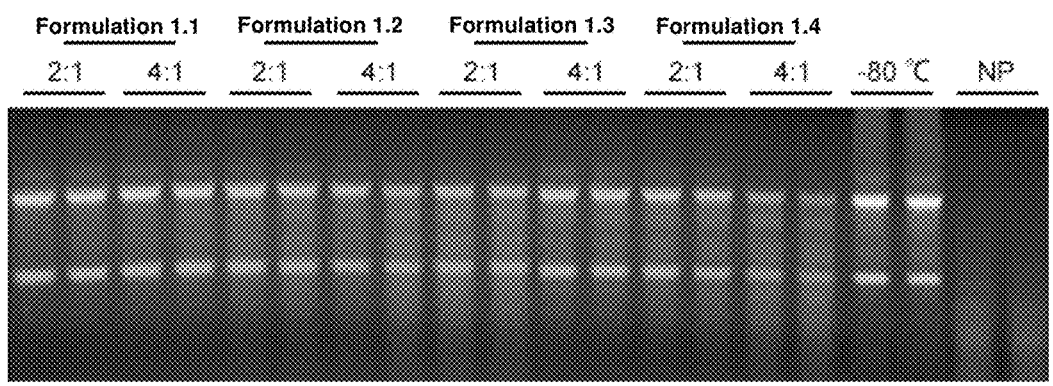
FIG. 10 shows the agarose gel electrophoretogram of the total RNA extracted from the human whole blood samples stored under different conditions. The human whole blood sample was first mixed with one of the stabilizers with Formulations 1.1-1.4 respectively at specific ratios, and then stored at room temperature; or directly stored at room temperature without stabilizer (NP); or stored at −80° C. without stabilizer. 15 days later, total RNA was extracted from the sample by using Ambion RiboPure™ Blood Kit, and was subjected to electrophoresis on 1% agarose gel.

Example 6 Stability of RNA in a Blood Sample Stored at Room Temperature for 15 Days A blood (whole blood) sample collected from a volunteer was placed in a vacuum blood collection tube containing anticoagulant $K_2$-EDTA, and mixed with one of the stabilizers with Formulations 1.1-1.4 (Table 1) respectively, at a ratio of 2:1 or 4:1. After mixing under vortexing, the sample was stored at room temperature. 300 μL blood sample stored at room temperature was used as unprotected control sample (NP), and 300 μL blood sample stored at −80° C. was used as freezing control sample. After storage at room temperature for 15 days, the samples were centrifuged at a centrifugal force of 14000 g for 5 min, and the supernatant was removed. The precipitate was dissolved in lysis buffer (800 μL) and sodium acetate solution (50 RP from Ambion RiboPure™ Blood Kit (Ambion, Austin, Tex.) by sufficient mixing, and then, in accordance with the instructions of the kit, RNA was extracted from the blood sample. RNA extraction was also carried in the sample stored without stabilizer at −80° C. after the sample was thawed, and in the sample stored without stabilizer at room temperature. The extracted RNA was loaded into sample well of an ethidium bromide-containing 1% agarose gel. After electrophoresis at 150V for 35 min, photographs were taken by ultraviolet ray (UVI) imaging system. The electrophoretogram is shown in FIG. 10.

The results show that the RNA obtained from the sample stored without stabilizer at room temperature was completely degraded, and it showed severely smeared in the lanes, and no RNA bands were observed. In contrast, the RNA obtained from the sample stored with stabilizer at room temperature, showed distinct bands (including the two main bands of 18S and 28S rRNA) in the electrophoretogram, with a relatively high integrity.

Example 8 Stability of Genomic DNA and RNA in 293T Cells

Figure 11:
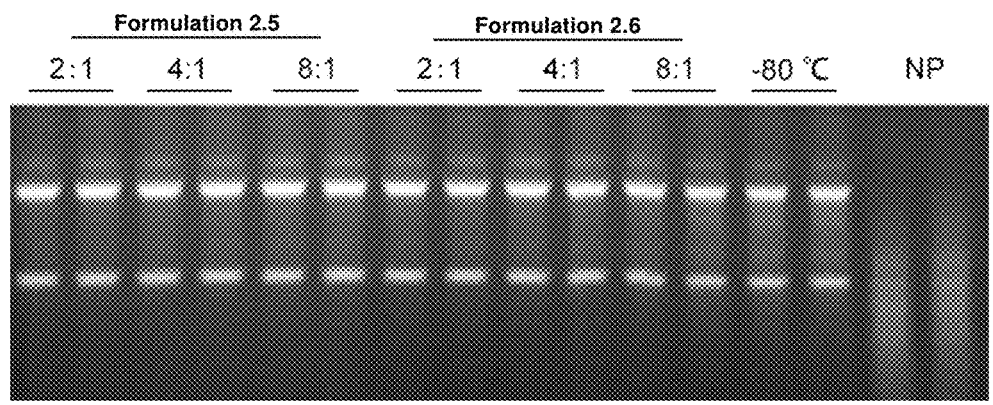
FIG. 11 shows the agarose gel electrophoretogram of the total RNA extracted from the human embryonic kidney (HEK) 293T cell samples stored under different conditions. The human embryonic kidney 293T cell sample was first mixed with the stabilizer with Formulation 2.5 or Formulation 2.6 at specific ratios, and then stored at room temperature; or directly stored at room temperature without stabilizer (NP); or stored at −80° C. without stabilizer. 15 days later, total RNA was extracted from the sample, and was subjected to electrophoresis on 1.2% agarose gel.
Figure 12:
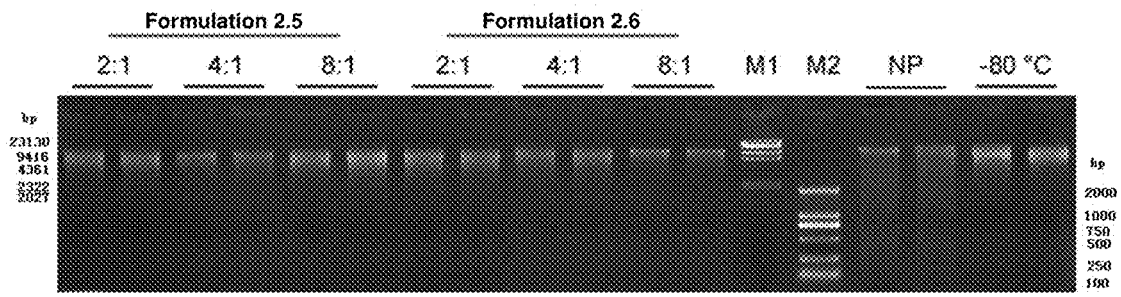
FIG. 12 shows the agarose gel electrophoretogram of the DNA extracted from the human embryonic kidney 293T cell samples stored under different conditions. The human embryonic kidney 293T cell sample was first mixed with the stabilizer with Formulation 2.5 or Formulation 2.6 at specific ratios, and then stored at room temperature; or directly stored at room temperature without stabilizer (NP); or stored at −80° C. without stabilizer. 15 days later, the DNA was extracted from the sample, and was subjected to electrophoresis on 1.2% agarose gel.

The human embryonic kidney (HEK) 293T cells (ATCC, Manassas, Va., USA) were cultured by standard cell culture method, and the cells thus obtained were washed. The cells were mixed with stabilizer with Formulation 15 or Formulation 2.6 (Table 2) at a ratio of 2:1, 4:1 and 8:1, respectively, and stored at room temperature. In addition, two samples containing an equal amount of cells without stabilizer were used as control, wherein one was stored at room temperature (NP), and the other was stored at −80° C. After the storage of all the samples for 15 days, genomic DNA and total RNA were extracted by using RNAqueous™ Kit (Ambion Company, Austin, Tex.), and detailed steps were performed according to manufacturer's instructions. The nucleic acid samples obtained were detected by 1.2% agarose gel electrophoresis. The RNA electrophoretogram (FIG. 11) shows that in the sample stored without stabilizer at room temperature, its RNA was completely degraded, and no independent RNA band was observed; in contrast, in the electrophoretogram of the samples stored with stabilizer with Formulation 2.5 or Formulation 2.6 at room temperature, the RNA had relatively distinct bands (including two main bands of 18S and 28S rRNA), and their integrity was comparable to that in the sample stored without stabilizer at −80° C., or even better. The DNA electrophoretogram (FIG. 12) shows that in the electrophoretogram of the samples stored with stabilizer with Formulation 2.5 or Formulation 2.6 at room temperature, the DNA had more clearly resolved and intensive bands, which were as good as the bands for the DNA in the sample stored at −80° C.; while in the sample stored without stabilizer at room temperature, the DNA was severely degraded, and the bands were severely smeared.

Example 9 Stability of RNA and Protein in a Sample of Mouse Brain Tissue Stored at Room Temperature According to the existing process for collection of laboratory animal tissue, fresh samples of mouse brain tissue (about 25 mg for each sample) were obtained, stored individually in centrifuge tubes, and stored by four methods respectively: one referred to the storage without any stabilizers, one referred to the storage with the addition of 100 μL stabilizer with Formulation 2.5, and one referred to the storage with the addition of 100 μL stabilizer with Formulation 2.6 (Table 2), wherein the samples treated by the three methods were stored at room temperature; and the last one referred to the storage without any stabilizers at −80° C., as control. Ml the treatments were performed in duplicates, and the samples were stored under the corresponding conditions for 15 days or 24 days. After the storage, total RNA was extracted from each of said samples by using RNAqueous™ Kit (Ambion Company, Austin, Tex.), and detailed steps were performed according to manufacturer's instructions. RNA integrity was evaluated by using Agilent RNA 6000

Nano Kit and Agilent 2100 Bioanalyzer (Agilent Technologies Inc., Santa Clara, Calif.), and the results were expressed as RIN (RNA integrity).

Figure 13:
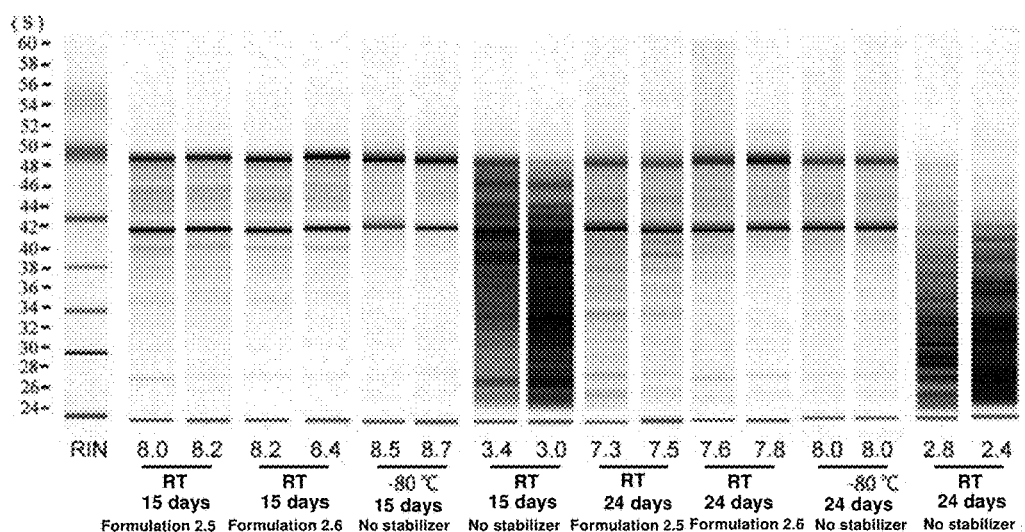
FIG. 13 shows the integrity (RIN) of the total RNA extracted from the mouse brain tissue samples stored under different conditions. The mouse brain tissue sample (~25 mg) was stored at room temperature with the addition of the stabilizer with Formulation 2.4 (100 μL); or directly stored at room temperature without stabilizer (NP); or stored at −80° C. without stabilizer. 15 or 24 days later, total RNA was extracted from the sample, and was evaluated for RNA integrity by using Agilent RNA 6000 Nano Kit and Agilent 2100 Bioanalyzer (Agilent Technologies Inc., Santa Clara, Calif.).

15 days later, the average value of RIN was 8.1 and 8.3 for the RNA in the samples stored with stabilizer with Formulation 2.5 and Formulation 2.6 at room temperature (FIG. 13), respectively, which were slightly lower than the average value of RIN (8.6) for the RNA in the sample stored at −80° C., while the average value of RIN was only 3.2 for the RNA in the sample stored without stabilizer at room temperature. 24 days later, the average value of RIN was 7.4 and 7.7 for the RNA in the samples stored with stabilizer with Formulation 2.5 and Formulation 2.6 at room temperature, respectively, which were close to the average value of RIN (8M) for the RNA in the sample stored at −80° C., while the value of RIN was only 2.6 for the RNA in the sample stored without stabilizer at room temperature.

Figure 14:
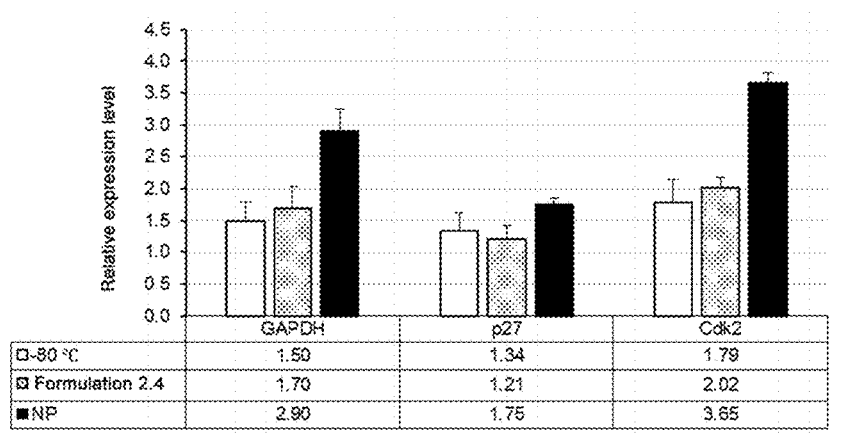
FIG. 14 shows the transcription levels of GAPDH, P23 and Cdk2 gene in the mouse brain tissue samples stored under different conditions. The mouse brain tissue sample (~25 mg) was stored at room temperature with the addition of the stabilizer with Formulation 2.4 (100 μL); or directly stored at room temperature without stabilizer (NP); or stored at −80° C. without stabilizer. 15 days later, total RNA was extracted from the sample, and the transcription levels of GAPDH, P23 and Cdk2 gene were determined by RT-qPCR method.

The samples of mouse brain tissue (about 25 mg for each sample) prepared by the method as described above, were stored with stabilizer with Formulation 2.4 (Table 2) at room temperature, or stored without stabilizer at room temperature (NP), or stored without stabilizer at −80° C. 15 days later, the total RNA was extracted from each of the samples. The cDNA fragments of murine GAPDH, P23 and Cdk2 were used to design specific primers, and Real-Time Quantitative PCR (RT-qPCR) analysis was performed. 250 pg, 2.5 ng or 25 ng was used in reverse transcription, and was amplified by standard quantitative PCR method, and comparative analysis was performed to the RNA samples. The results (FIG. 14) show that after storage with stabilizer with Formulation 2.4 at room temperature for 15 days, the transcription levels of the three genes were comparable to those in the control stored at −80° C.; while in the sample stored without stabilizer at room temperature, the transcription levels of the three genes were greatly enhanced.

The samples of mouse brain tissue (about 25 mg for each sample) prepared by the method as described above, were transferred into PAXgene™ Tissue FIX Containers (50 ml) and fixed, followed by removal of PAXgene Tissue FIX and addition of PAXgene™ Tissue STABILIZER (Qiagen, Valencia, Calif.) to the same container, and then stored at room temperature. Or the samples were directly transferred to collection tubes, and stored with stabilizer with Formulation 2.4 (Table 2) at room temperature; or stored without stabilizer at room temperature (NP); or stored without stabilizer at −80° C. 7 days later, the proteins were extracted from each of said samples by using SurePrep™ Kit (Fisher Scientific, Pittsburgh, Pa.), and detailed steps were performed according to manufacturer's instructions. The protein concentration was determined by Pierce BCA Analytical Kit (Thermo Fisher Scientific, Rockford, Ill.). An equal amount of protein extract was subjected to electrophoresis on a 4-20% gradient tris-glycine polyacrylamide gel (Invitrogen, Carlsbad, Calif.). After the electrophoresis, the protein was electrotransferred onto nitrocellulose membrane, and stained with Ponceau S solution. Western Blot analysis was carried out by using antibodies for murine Dynein and β-actin.

Figure 15:
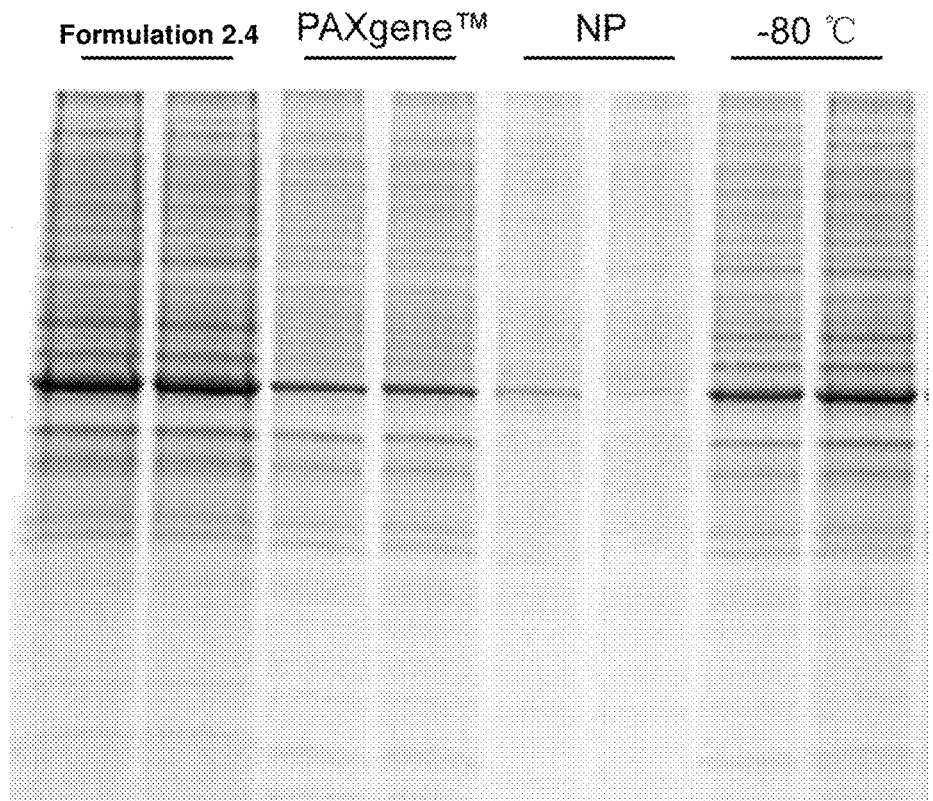
FIG. 15 shows the polyacrylamide gel electrophoretogram of the total protein extracted from the mouse brain tissue samples stored under different conditions. Firstly, the mouse brain tissue sample (~25 mg) was prepared. The sample was transferred into PAXgene™ Tissue FIX Container (50 ml) and fixed, followed by removal of PAXgene Tissue FIX and addition of PAXgene™ Tissue STABILIZER (Qiagen, Valencia, Calif.) to the same container, and then stored at room temperature. Or, the sample was directly transferred to a collection tube, and stored at room temperature with the addition of the stabilizer with Formulation 2.4 (Table 2); or stored at room temperature without stabilizer (NP); or stored at −80° C. without stabilizer. 7 days later, the total protein was extracted from the sample by using SurePrep™ Kit, and was subjected to electrophoresis on 4-20% gradient polyacrylamide gel.
Figure 16:
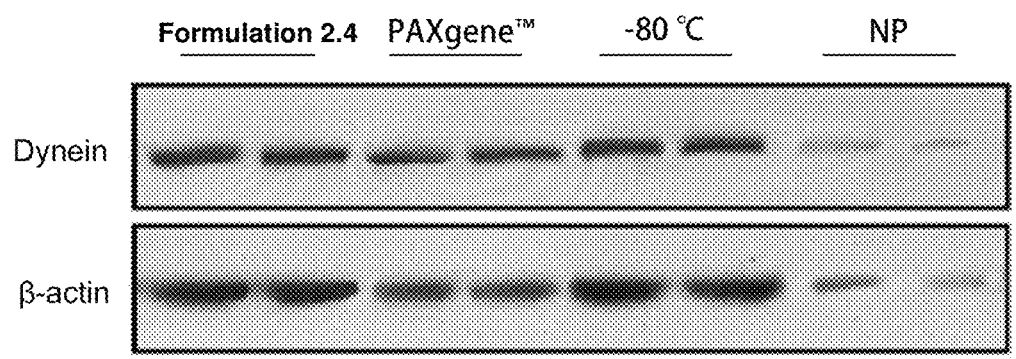
FIG. 16 shows the Western Blot results of the total protein extracted from the mouse brain tissue samples stored under different conditions. Firstly, the mouse brain tissue sample (~25 mg) was prepared. The sample was transferred into PAXgene™ Tissue FIX Container (50 ml) and fixed, followed by removal of PAXgene Tissue FIX and addition of PAXgene™ Tissue STABILIZER (Qiagen, Valencia, Calif.) to the same container, and then stored at room temperature. Or, the sample was directly transferred to a collection tube, and stored at room temperature with the addition of the stabilizer with Formulation 2.4 (Table 2); or stored at room temperature without stabilizer (NP); or stored at −80° C. without stabilizer. 7 days later, the total protein was extracted from the sample, and was subjected to electrophoresis on 4-20% gradient polyacrylamide gel. After the electrophoresis, the protein was electrotransferred onto nitrocellulose membrane, and Western Blot analysis was carried out by using antibodies for murine Dynein and β-actin.

By staining with Ponceau S, in the electrophoretogram, the bands for the protein extract in the sample stored with stabilizer with Formulation 2.4 were dearer and more distinct than the bands in the sample stored with the stabilizer PAXgene™ Tissue STABILIZER Concentrate (FIG. 15); while in the electrophoretogram, the bands for the protein in the sample stored without stabilizer at room temperature, were weak and smeared. Western blot analysis (FIG. 16) shows: the content of Dynein in the protein extract in the sample stored with stabilizer with Formulation 2.4 at room temperature was substantively consistent with the content of Dynein in the protein extract in the sample stored without stabilizer at −80° C., and the intensity of their bands was comparable; while in the protein extract in the sample stored with the stabilizer PAXgene™ Tissue STABILIZER Concentrate at room temperature, the content of Dynein was lower, and the intensity of the bands was lower; in the protein extract in the sample stored without stabilizer at room temperature, the content of Dynein was much lower, and the bands were not obvious. In the protein extracts from the samples stored under three conditions, the bands for actin could be clearly detected in Western Blot. Also, the stabilizer with Formulation 2.4 had a better effect in storage of the protein in the tissue sample than the stabilizer PAXgene™ Tissue STABILIZER Concentrate, while the bands for the protein extract in the sample stored without stabilizer at room temperature were weaker, and the effect in storage was the worst.

Figure 17:
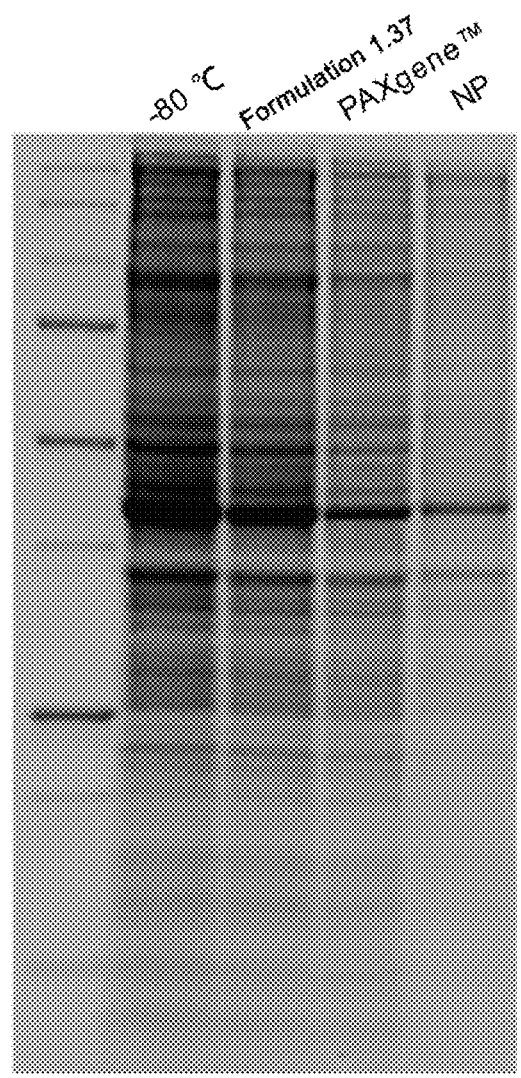
FIG. 17 shows the polyacrylamide gel electrophoretogram of the total protein extracted from the tumor tissue samples of breast cancer stored under different conditions. Firstly, the tumor tissue sample of breast cancer (~25 mg) was prepared. The sample was transferred into PAXgene™ Tissue FIX Container (50 ml) and fixed, followed by removal of PAXgene Tissue FIX and addition of PAXgene™ Tissue STABILIZER (Qiagen, Valencia, Calif.) to the same container, and then stored at room temperature. Or the sample was directly transferred to a collection tube, and stored at room temperature with the addition of the stabilizer with Formulation 1.37 (Table 1); or stored at room temperature without stabilizer (NP); or stored at −80° C. without stabilizer. 7 days later, the total protein was extracted from the sample, and was subjected to electrophoresis on polyacrylamide gel.

Example 10 Stability of Protein in a Tumor Sample of Human Breast Cancer at Room Temperature The samples of human breast cancer (about 25 mg for each sample) prepared by the method as described above, were transferred into PAXgene™ Tissue FIX Containers (50 mil and fixed, followed by removal of PAXgene Tissue FIX, and addition of PAXgene™ Tissue STABILIZER (Qiagen, Valencia, Calif.) to the same container, and then were stored at room temperature. Or the samples were directly transferred to the collection tubes, and stored with stabilizer with Formulation 1.37 (Table 1) at room temperature; or stored without stabilizer at room temperature (NP); or stored without stabilizer at −80° C. After the storage for 7 days, the protein was extracted by the method as described above, and the protein extract was subjected to separation by electrophoresis. After electrotransfer onto nitrocellulose membrane, amido black was used for staining. The results are shown in FIG. 17. The results show that the protein extract in the sample stored with stabilizer with Formulation 1.37 at room temperature had multiple distinct bands in the electrophoretogram. By comparison, the bands for the sample stored with stabilizer with Formulation 1.37 were clearer and more distinct than the bands for the sample stored with the stabilizer PAXgene™ Tissue STABILIZER Concentrate; while in the electrophoretogram for the proteins in the sample stored without stabilizer at room temperature, the bands had weak intensity and were relatively smeared.

Figure 18:
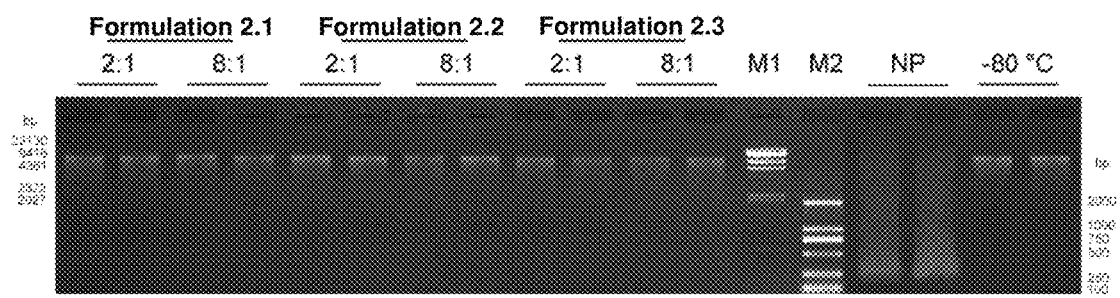
FIG. 18 shows the agarose gel electrophoretogram of the DNA extracted from the human whole blood samples stored under different conditions. The human whole blood sample was first mixed with one of the stabilizers with Formulations 2.1-2.3 respectively at two different ratios, and then stored at room temperature; or directly stored at room temperature without stabilizer (NP); or stored at −80° C. without stabilizer. 60 days later, DNA was extracted from the sample, and was subjected to electrophoresis on 0.8% agarose gel.

Example 11 Stability of RNA and DNA in a Human Blood Sample Stored at Room Temperature for a Long Time A blood (whole blood) sample collected from a volunteer was added to a vacuum blood collection tube containing anticoagulant $K_2$-EDTA, mixed with one of stabilizers with Formulations 2.1-2.3 (Table 2) respectively at a ratio of 2:1 or 8:1, and stored at room temperature; or stored without stabilizer at room temperature (NP), or stored without stabilizer at −80° C. 60 days later, the genomic DNA was extracted from the sample by using QIAamp™ Mini DNA Kit, and was subjected to agarose gel electrophoresis after purification. The results are shown in FIG. 18. It can be seen from the electrophoretogram that the DNA bands for the samples stored with stabilizers with Formulations 2.1-2.3 respectively at room temperature were much brighter and more clearly resolved than the DNA bands for the sample stored without stabilizer at room temperature.

Figure 19:
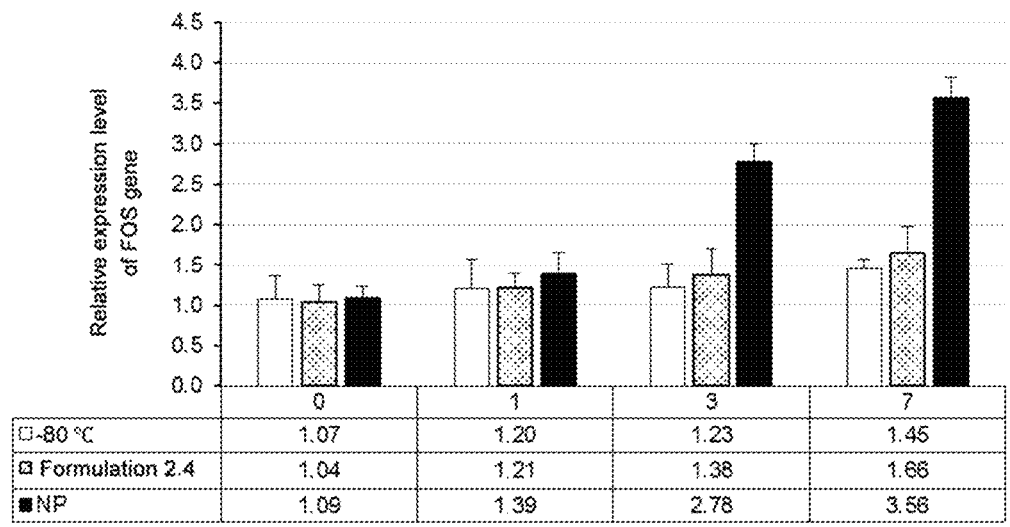
FIG. 19 shows the changes in the transcription level of FOS gene in the human whole blood samples stored under different conditions for different periods. The human whole blood sample was stored at room temperature with the addition of the stabilizer with Formulation 2.4; or directly stored at room temperature without stabilizer (NP); or stored at −80° C. without stabilizer. At the time of sample collection (i.e., 0 day), and after storage for 1, 3 and 7 days, total RNA was extracted from the sample, and the transcription level of FOS gene was determined by RT-qPCR method.
Figure 20:
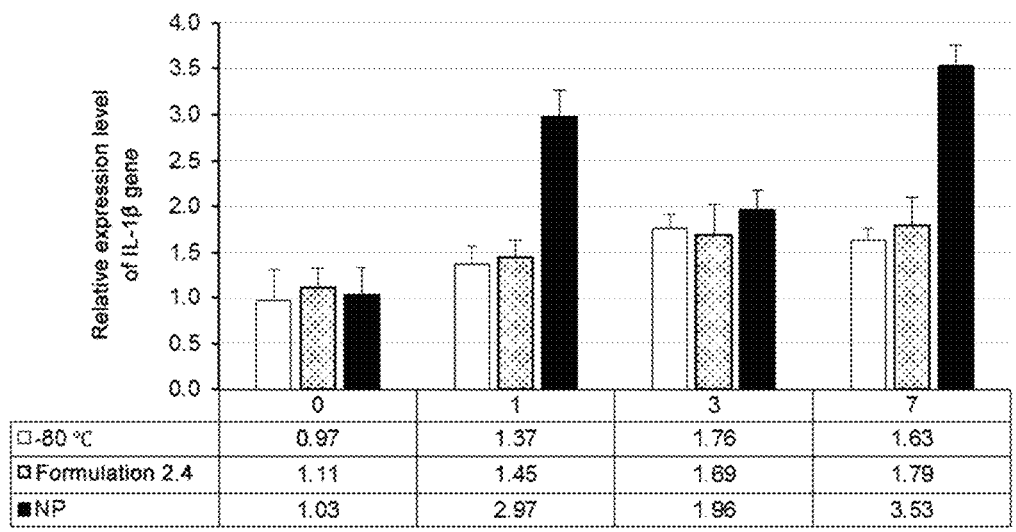
FIG. 20 shows the changes in the transcription level of IL-1β gene in the human whole blood samples stored under different conditions for different periods. The human whole blood sample was stored at room temperature with the addition of the stabilizer with Formulation 2.4; or directly stored at room temperature without stabilizer (NP); or stored at −80° C. without stabilizer. At the time of sample collection (i.e., 0 day), and after storage for 1, 3 and 7 days, total RNA was extracted from the sample, and the transcription level of IL-1β gene was determined by RT-qPCR method.

A human blood (whole blood) sample collected from a volunteer was added to a vacuum blood collection tube containing anticoagulant $K_2$-EDTA, and stored with stabilizer with Formulation 2.4 at room temperature, or stored without stabilizer at room temperature (NP), or stored without stabilizer at −80° C. At Day 0, 1, 3, and 7, the actin gene was used as internal reference, and the transcription levels of fructo-oligosaccharide (FOS) gene and IL-1 β gene were determined by RT-qPCR method. The results (FIG. 19, FIG. 20) show that the transcription levels of FOS gene and IL-1β gene in the sample stored with stabilizer with Formulation 2.4 at room temperature were comparable to those in the control sample stored at −80° C. at each of the detection time points; in contrast, in the sample stored without stabilizer at room temperature, the transcription level of FOS gene was gradually increased, while the transcription level of IL-1β gene was fluctuated widely.

Example 12 Stability of RNA in a Non-Cryostored Blood Sample

A blood (whole blood) sample collected from a volunteer was added to a PAXgene™ Blood RNA Tube, and stored at room temperature (RT) for 3 days or 7 days; or the sample was collected to a vacuum blood collection tube containing anticoagulant $K_2$-EDTA, and stored with stabilizer with Formulation 2.4 at room temperature (RT) for 3 days or 7 days, or stored without stabilizer at room temperature (RT) for 3 days, or stored without stabilizer at −80° C. for 7 days. Changes in the expression levels of 36 genes relative to the expression levels at the time of sample collection were determined by ΔΔCq method (Table 9), wherein the housekeeping genes PRL13A and GAPDH were used as internal reference, and all the experiments were performed in triplicate. The genes at time "0" had the same expression level, and the expression levels at specific time points of detection were showed in the corresponding linear curves (FIG. 21A-F). Straight boundaries in the scatter plot parallel to the diagonal line represent the 2-fold borderlines, and if a single dot represented for a gene is significantly higher than the upper boundary, it is regarded as up-regulation of the gene expression level; in contrast, if a single dot represented for a gene is significantly lower than the bottom boundary, it is regarded as down-regulation of the gene expression level.

TABLE 9

Changes in expression level of 36 genes before and after storage under different conditions as analyzed by RT-qPCR method

| Gene name | Expression level before storage | Storage method 1 RT 3 days No stabilizer | Storage method 2 −80° C. 7 days No stabilizer | Storage method 3 RT 3 days Formulation 2.4 | Storage method 4 RT 7 days Formulation 2.4 | Storage method 5 RT 3 days PAXgene™ | Storage method 6 RT 7 days PAXgene™ |
|---|---|---|---|---|---|---|---|
| BMP2 | −3.91 | −2.91 | −4.00 | −3.99 | −3.71 | −2.73 | −1.92 |
| IL1A | −3.87 | −2.37 | −3.69 | −3.97 | −4.00 | −3.97 | −3.92 |
| CSF2 | −3.84 | −1.74 | −3.60 | −4.04 | −3.76 | −3.92 | −3.99 |
| IL2 | −3.83 | −4.23 | −3.62 | −3.89 | −3.99 | −3.67 | −3.84 |
| IL17C | −3.81 | −3.96 | −3.97 | −3.97 | −3.91 | −3.91 | −3.69 |
| NODAL | −3.77 | −3.97 | −3.78 | −3.81 | −3.10 | −4.31 | −4.18 |
| TGFB3 | −3.69 | −3.89 | −3.71 | −3.59 | −3.65 | −3.69 | −3.45 |
| GDF10 | −3.60 | −3.40 | −3.62 | −3.61 | −3.47 | −3.45 | −3.46 |
| GDF9 | −3.59 | −3.69 | −4.03 | −3.74 | −3.67 | −3.65 | −2.45 |
| IL12A | −3.37 | −3.87 | −3.50 | −4.13 | −3.26 | −3.36 | −3.02 |
| IL6 | −3.37 | −3.47 | −3.42 | −3.31 | −3.29 | −3.19 | −3.18 |
| IL7 | −3.30 | −3.90 | −3.13 | −3.13 | −3.52 | −4.15 | −4.33 |
| IL10 | −3.26 | −3.06 | −3.27 | −3.16 | −3.38 | −1.02 | −1.42 |
| IFNK | −3.26 | −3.36 | −3.37 | −2.54 | −3.21 | −3.27 | −3.29 |
| GDF8 | −3.12 | −2.52 | −3.34 | −3.36 | −3.06 | −2.96 | −2.92 |
| PDGFA | −2.99 | −0.99 | −2.85 | −2.99 | −2.93 | −3.53 | −3.97 |
| GDF11 | −2.82 | −2.52 | −2.85 | −2.61 | −2.76 | −2.60 | −2.68 |
| BMP8B | −2.78 | −2.80 | −3.79 | −2.58 | −2.97 | −3.79 | −3.82 |
| INH13A | −2.61 | −3.61 | −2.51 | −2.74 | −2.64 | −2.63 | −2.54 |
| FASLG | −2.43 | −2.23 | −2.27 | −2.38 | −2.63 | −2.49 | −2.25 |
| BMF6 | −2.39 | −2.39 | −2.46 | −2.36 | −2.27 | −2.54 | −2.49 |
| INFG | −2.37 | −2.17 | −2.25 | −2.23 | −2.31 | −1.28 | −0.62 |
| LTA | −2.33 | −4.10 | −1.23 | −2.56 | −2.46 | −2.32 | −2.20 |
| CSF1 | −1.97 | −1.77 | −1.89 | −1.93 | −0.95 | −3.10 | −3.47 |
| TNF | −1.97 | −2.67 | −2.17 | −2.03 | −2.25 | −1.72 | −2.16 |
| IL8 | −1.97 | −0.57 | −1.84 | −2.02 | −2.02 | −1.78 | −2.01 |
| TNFSF13 | −1.44 | −2.77 | −1.54 | −1.61 | −1.33 | −1.27 | −0.26 |
| TGFA | −1.38 | −2.48 | −1.59 | −1.37 | −1.34 | −3.01 | −1.54 |
| TNFSF13B | −1.28 | −1.23 | −1.48 | −0.10 | −1.04 | −0.54 | −0.48 |
| TNFSF12 | −1.18 | −1.23 | −1.28 | −1.17 | −2.75 | −1.32 | −1.10 |
| TNFSF14 | −1.15 | −1.08 | −1.00 | −0.97 | −1.26 | −3.36 | −4.09 |
| IL24 | −1.06 | −1.46 | −0.92 | −1.17 | −2.20 | −1.02 | −1.19 |
| TNFSF10 | −0.04 | −0.44 | −0.08 | −0.15 | 0.00 | −0.12 | −0.02 |
| IL16 | 0.17 | 0.21 | 0.33 | 0.24 | 0.18 | 0.06 | 0.30 |
| LTB | 0.23 | 0.43 | 0.01 | 0.23 | 0.00 | 0.00 | 0.05 |
| ACTB | 0.72 | 0.52 | 0.94 | 0.74 | 0.53 | 0.64 | 0.62 |

Table 10 summarizes the results of expression stability of multiple genes in blood samples after storage at room temperature as analyzed by RT-qPCR method. The blood (whole blood) samples collected from volunteers were added to PAXgene™ Blood RNA Tubes, and stored at room temperature for 3 days or 7 days; or the samples were collected to vacuum blood collection tubes containing anticoagulant $K_2$-EDTA, and stored with stabilizer with Formulation 2.4 at room temperature for 3 days or 7 days, or stored without stabilizer at room temperature for 3 days, or stored without stabilizer at −80° C. for 7 days. Changes in the expression levels of 36 genes relative to the expression levels at the time of sample collection were determined by ΔΔCq method, wherein the house-keeping genes PRL13A and GAPDH were used as internal reference, and all the experiments were performed in triplicate. The results show that in the sample stored without stabilizer at room temperature for 3 days, the number of up-regulated genes reached 7, and the number of down-regulated genes reached 10, and the sum of them accounted for 47% of all the tested genes; while in the sample stored at −80° C., the number of the up-regulated genes and the down-regulated genes was 1 and 2, respectively, and the sum of them only accounted for 8% of the total number. In contrast, after the sample was stored with stabilizer with Formulation 2.4 at room temperature for 3 days, the number of the up-regulated genes and the down-regulated genes was 2 and 1, respectively, and the sum of them accounted for 8% of the total number; after storage for 7 days, the number of the down-regulated genes increased by 1, and the sum of them accounted for 11% of the total number, which was similar to the result of the storage at −80° C. In addition, it was found by comparison that the stabilizer with Formulation 2.4 had a better effect in storage than the PAXgene™ Blood RNA Tube.

TABLE 10

RT-qPCR results

| Group | Treatment | Number of up-regulated genes | Number of down-regulated genes | Percentage (%) |
| --- | --- | --- | --- | --- |
| Storage method 1 | RT 3 days No stabilizer | 7 | 10 | 47 |
| Storage method 2 | −80° C. 7 days No stabilizer | 1 | 2 | 8 |
| Storage method 3 | RT 3 days Formulation 2.4 | 2 | 1 | 8 |
| Storage method 4 | RT 7 days Formulation 2.4 | 2 | 2 | 11 |
| Storage method 5 | RT 3 days PAXgene ™ | 4 | 7 | 31 |
| Storage method 6 | RT 7 days PAXgene ™ | 6 | 6 | 33 |

Figure 22:
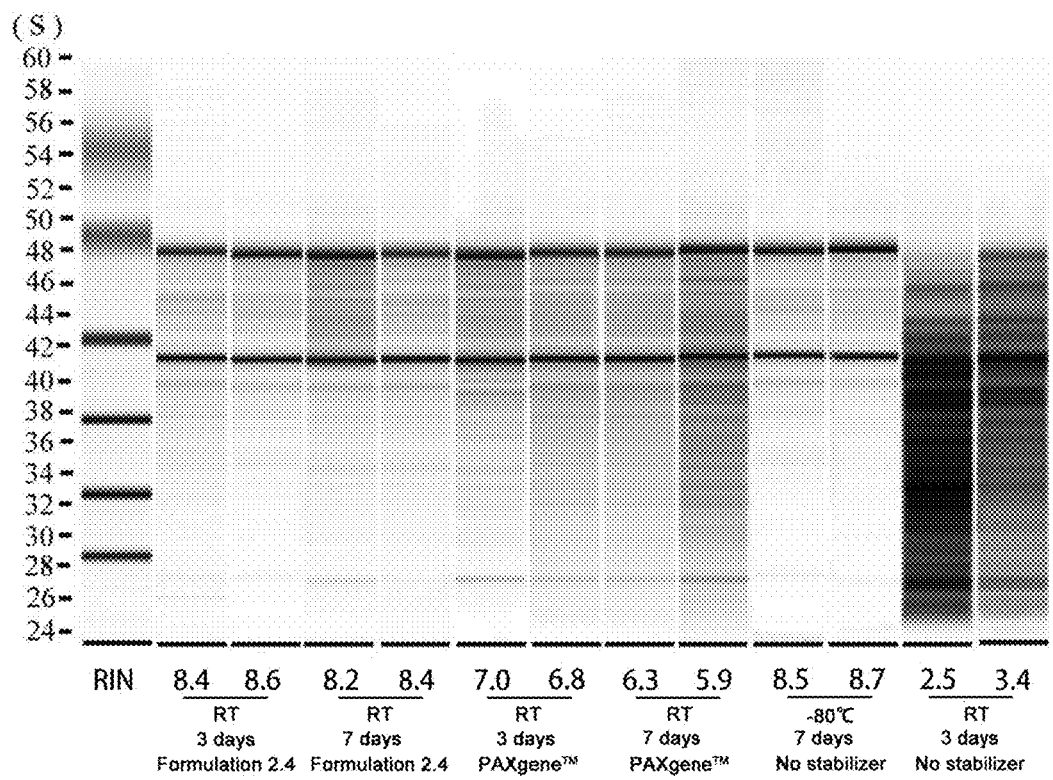
FIG. 22 shows the integrity (RIN) of the total RNA extracted from the human whole blood samples stored under different conditions. The human whole blood sample was stored at room temperature with the addition of the stabilizer with Formulation 2.4 for 3 days or 7 days; or stored by utilizing PAXgene™ Blood RNA Tube at room temperature for 3 days or 7 days; or directly stored at room temperature without stabilizer for 3 days; or stored at −80° C. without stabilizer for 7 days. After the storage, total RNA was extracted from the sample, and was evaluated for RNA integrity.

In another experiment, blood (whole blood) samples collected from volunteers were added to PAXgene™ Blood RNA Tubes, and stored at room temperature for 3 days or 7 days; or the samples were added to vacuum blood collection tubes containing anticoagulant $K_2$-EDTA, stored with stabilizer with Formulation 2.4 at room temperature for 3 days or 7 days, or stored without stabilizer at room temperature for 3 days, or stored without stabilizer at −80° C. for 7 days. Total RNA was extracted from the blood samples by using RNAqueous™ Kit (Ambion, Austin, Tex.), and the RNA integrity (RIN) was analyzed by using Agilent 2100 Bioanalyzer and RNA 6000 Nano Kit. The results are shown in FIG. 22. The results show that for the RNA in the sample stored with stabilizer with Formulation 2.4 at room temperature for 3 days, the average value of RIN was 8.5, which was much higher than the RIN value (195) for the RNA obtained from the sample stored without stabilizer at room temperature for 3 days. For the RNA in the sample stored with stabilizer with Formulation 2.4 at room temperature for 7 clays, the average value of RIN was 8.3, which was slightly lower than the average value of RIN (8.6) for the RNA from the sample stored at −80° C. In addition, it is found that the RIN value for the RNA obtained from the sample stored by utilizing PAXgene™ Blood RNA Tube at room temperature for 3 days or 7 days was lower than the RIN value for the RNA obtained from the sample stored with stabilizer with Formulation 2.4, indicating that the stabilizer with Formulation 2.4 had a better effect in storage.

Figure 23:
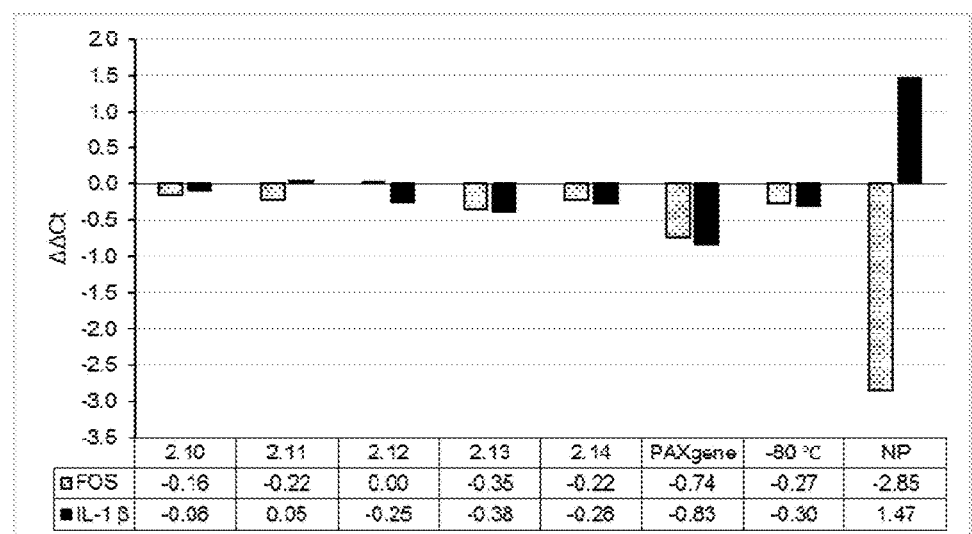
FIG. 23 shows the RT-qPCR analytic results of FOS and IL-1β genes in the human whole blood samples stored under different conditions. The human whole blood sample was stored at room temperature with the addition of one of the stabilizers with Formulations 2.10-2.14 respectively; or stored by utilizing PAXgene™ Blood RNA Tube at room temperature; or directly stored at room temperature without stabilizer (NP); or stored at −80° C. without stabilizer. 7 days later, changes in transcription levels of FOS and IL-1β genes relative to the levels at the time "0" (i.e., at the time of sample collection) were determined by RT-qPCR method.

In another study, blood (whole blood) samples collected from volunteers were added to PAXgene™ Blood RNA Tubes, and stored at room temperature; or the samples were collected to vacuum blood collection tubes containing anticoagulant K2-EDTA, or stored with one of stabilizers with Formulations 2.10-2.14 (Table 2) respectively at room temperature, or stored without stabilizer at room temperature (NP), or stored without stabilizer at −80° C. Total RNA was extracted from each of the samples when the samples were collected (at time "0") and after storage under specified conditions for 7 days. By using the method as described above, changes in the transcription level of FOS and IL-1β genes in the blood after storage relative to the transcription level at the time "0" were analyzed by RT-qPCR technology, wherein human β-actin gene was used as internal inference. The results are shown in FIG. 23. The results show that the transcription levels of FOS gene and IL-10 gene in the sample stored with stabilizers with Formulations 2.10-2.11 respectively at room temperature were comparable to that in the control sample stored at −80° C., with little difference; while the transcription levels of the two genes in the sample stored by utilizing PAXgene™ Blood RNA Tube at room temperature were greatly reduced relative to the those in the control sample stored at −80° C.; in contrast, the transcription levels of the two genes in the sample stored without stabilizer at room temperature were greatly changed, wherein the transcription level of FOS gene was significantly reduced, while the transcription level of IL-1β gene was greatly increased.

Figure 24:
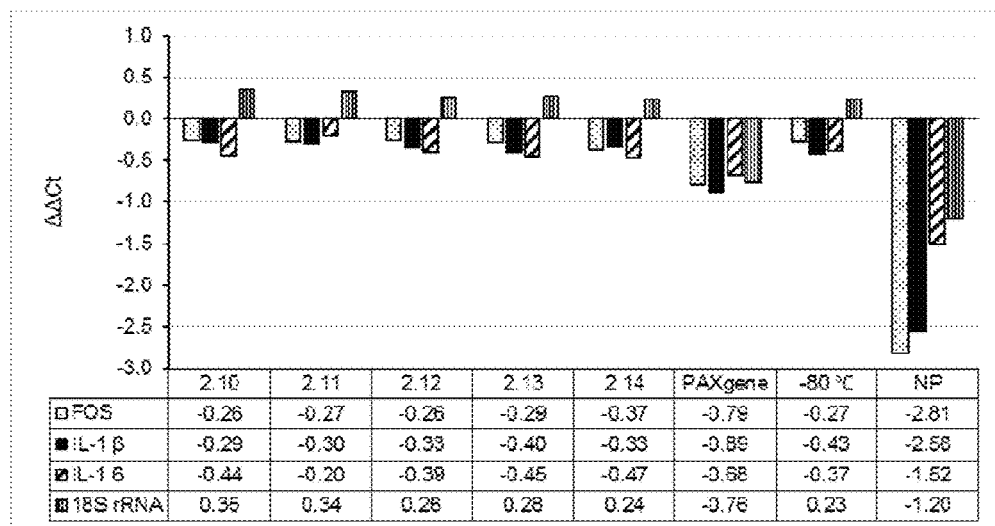
FIG. 24 shows the RT-qPCR analytic results of FOS, IL-1 β, IL-16 and 18S rRNA genes in the human whole blood samples stored under different conditions. The human whole blood sample was stored at room temperature with the addition of one of the stabilizers with Formulations 2.10-2.14 respectively; or stored by utilizing PAXgene™ Blood RNA Tube at room temperature; or directly stored at room temperature without stabilizer (NP); or stored at −80° C. without stabilizer. 14 days later, changes in transcription levels of FOS, IL-1 β, IL-16 and 18S rRNA genes relative to the levels at the time "0" (i.e., at the time of sample collection) were determined by RT-qPCR method.

In addition, the inventors also made a similar analysis, except that the storage period was 14 days instead of 7 days, and the kinds of genes to be analyzed also increased, which further included IL-16 and 18S rRNA gene. Blood (whole blood) samples collected from volunteers were added to PAXgene™ Blood RNA Tube, and stored at room temperature; or the samples were collected to vacuum blood collection tubes containing anticoagulant $K_2$-EDTA, and stored with one of stabilizers with Formulations 2.10-2.14 (Table 2) respectively at room temperature, or stored without stabilizer at room temperature (NP), or stored without stabilizer at −80° C. Total RNA was extracted from each of the samples when the samples were collected (at time "0") and after storage under specified conditions for 14 days. By using the method as described above, changes in the transcription levels of the genes encoding FOS, IL-1β, IL-16 and 18S rRNA in the blood after the storage relative to the transcription levels at the time "0" were analyzed by RT-qPCR technology, wherein human β-actin gene was used as internal inference. The results are shown in FIG. 24. The results show that the transcription levels of the four genes in the samples stored with stabilizers with Formulations 2.10-2.11 respectively at room temperature were comparable to that in the control sample stored at −80° C., with little difference; the stabilizers with Formulations 2.10-2.11 had a better effect in storage than PAXgene™ Blood RNA Tube; while the transcription levels of the four genes in the samples stored without stabilizer at room temperature were greatly changed, and were greatly reduced.

Example 13 Stability of DNA in a Blood Sample Stored Under Non-Freezing Condition for More than 6 Months Blood (whole blood) samples collected from volunteers were added to vacuum blood collection tubes containing anticoagulant K2-EDTA, and stored with one of stabilizers with Formulations 2.9-2.20 (Table 2) at room temperature, or stored without stabilizer at room temperature (NP), or stored without stabilizer at −80° C.

Figure 25:
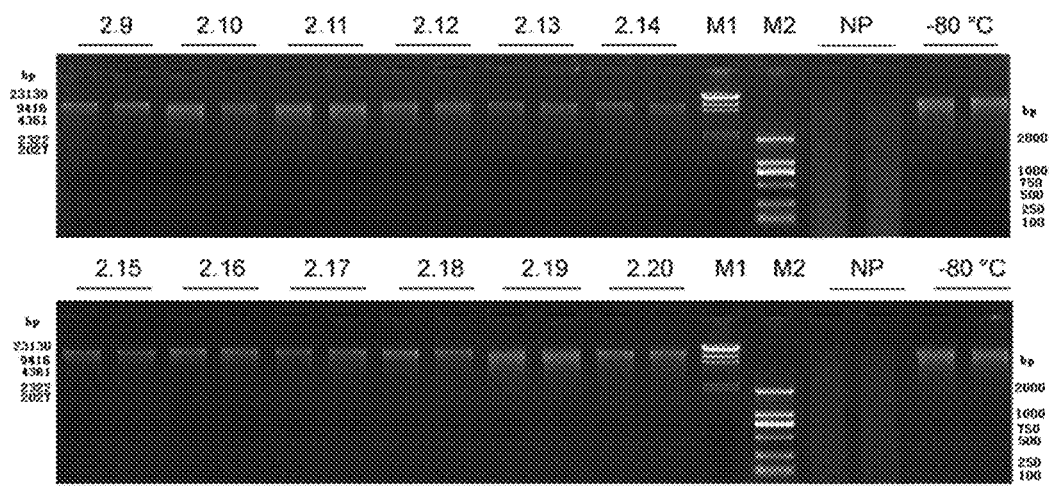
FIG. 25 shows the agarose gel electrophoretogram of the DNA extracted from the human whole blood samples stored under different conditions. The human whole blood was stored at room temperature with the addition of one of the stabilizers with Formulations 2.9-2.20 respectively; or directly stored at room temperature without stabilizer (NP); or stored at −80° C. without stabilizer. 186 days later, DNA was extracted from the sample, and was subjected to electrophoresis on 0.8% agarose gel.

The samples stored at room temperature were placed on laboratory bench. 186 days later, in accordance with the instructions, genomic DNA was extracted by using QiaAmp™ mini Kit (Qiagen, Valencia, Calif.). The extracted DNA was subjected to electrophoresis on ethidium bromide-containing 0.8% agarose gel. The results (FIG. 25) show that the bands of the DNA in the sample stored with stabilizer were more distinct and brighter than the bands of the DNA in the sample stored without stabilizer at −80° C., while the bands of the DNA in the sample stored without stabilizer at room temperature were severely smeared and with tails backwards towards small fragments, indicating severe degradation.

Example 14 Stability of RNA and DNA in a Non-Cryostored Urine Sample

Figure 26:
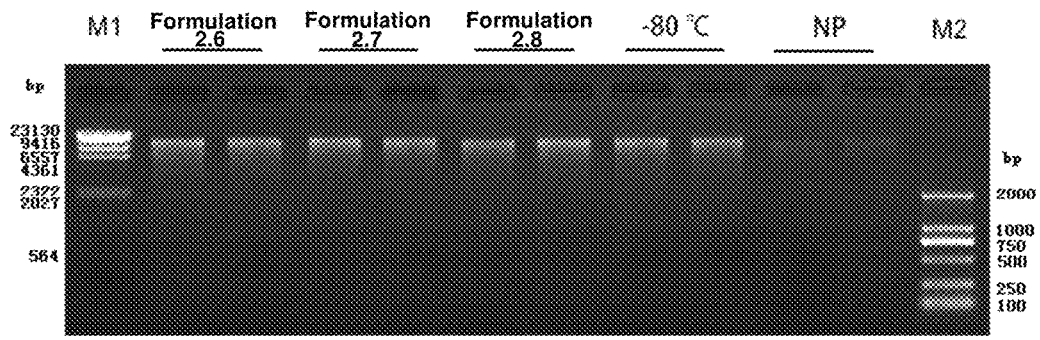
FIG. 26 shows the agarose gel electrophoretogram of the DNA extracted from the human urine samples stored under different conditions. The human urine sample was stored at room temperature with the addition of one of the stabilizers with Formulations 2.6-2.8 respectively; or directly stored at room temperature without stabilizer (NP); or stored at −80° C. without stabilizer. 30 days later, DNA was extracted from the sample, and was subjected to electrophoresis on 1.2% agarose gel.
Figure 27:
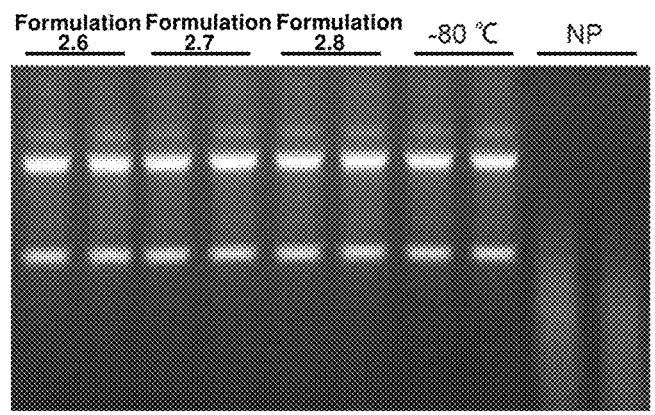
FIG. 27 shows the agarose gel electrophoretogram of the total RNA extracted from the human urine samples stored under different conditions. The human urine sample was stored at room temperature with the addition of one of the stabilizers with Formulation 2.6-2.8 respectively; or directly stored at room temperature without stabilizer (NP); or stored at −80° C. without stabilizer. 30 days later, the total RNA was extracted from the sample, and was subjected to electrophoresis on 1.2% agarose gel.

Urine samples collected from volunteers, were stored on ice for further use. 200 μL urine sample was sufficiently mixed with an equal amount of one of stabilizers with Formulations 2.6-2.8 (Table 2). Two control samples without stabilizer were prepared, wherein one control sample stored at −80° C. was used as freezing control, and the other control sample (NP) together with the samples stored with stabilizer were placed at room temperature in dark. All the treatments were performed in duplicate. After the storage for 30 days, genomic DNA and total RNA were extracted from said samples by using said DNA and RNA extraction kits, respectively, and detailed steps were performed according to manufacturer's instructions. The nucleic acid samples obtained were subjected to 1.2% agarose gel electrophoresis. DNA electrophoretogram (FIG. 26) shows that DNA from the sample stored with stabilizer at room temperature had bright bands in the electrophoretogram, which were comparable to the bands of DNA from the control sample stored at −80° C. However, in the sample stored without stabilizer at room temperature, DNA was severely degraded, and the bands were blurred and had very low intensity. RNA electrophoretogram (FIG. 27) shows that in the sample stored without stabilizer at room temperature, its RNA was completely degraded, and no independent RNA bands were observed. In contrast, in the sample stored with stabilizer at room temperature, relatively distinct bands for the RNA can be detected in the electrophoretogram, and the ratio of the intensity of 28S band and 18S band was close to 2:1, indicating that the RNA obtained had high quality.

Example 15 Stability of RNA and DNA in a Non-Cryostored Saliva Sample

Figure 28:
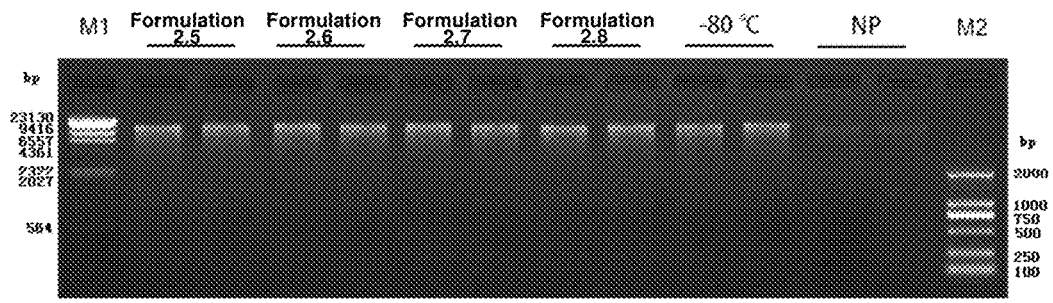
FIG. 28 shows the agarose gel electrophoretogram of the DNA extracted from the human saliva samples stored under different conditions. The human saliva sample was stored at room temperature with the addition of one of the stabilizers with Formulations 2.5-2.8 respectively; or directly stored at room temperature without stabilizer (NP); or stored at −80° C. without stabilizer. 30 days later, DNA was extracted from the sample, and was subjected to electrophoresis on 1.2% agarose gel.

Saliva samples collected from volunteers, were stored on ice for further use. The saliva samples were mixed sufficiently. 200 μL saliva sample was mixed with an equal amount of one of stabilizers with Formulations 2.5-2.8 (Table 2) in a polypropylene bottle with screw cap. Two control samples without stabilizer were prepared, wherein one control sample stored at −80° C. was used as freezing control, and the other control sample (NP) together with the samples stored with stabilizer was placed at room temperature in dark. All the treatments were performed in duplicate. After the storage for 30 days, DNA was extracted from 300 μl each of the samples by using QIAamp Purification mini Kit (Qiagen, Valencia, Calif.), and detailed steps were performed according to manufacturer's instructions. Finally, the extracted genomic DNA was eluted with 100 μL AE eluent, and 10 μL eluate was loaded into the sample well of ethidium bromide-containing 1.2% agarose gel. After gel electrophoresis at 120 V for 40 min, photographs were taken by ultraviolet ray (UVI) imaging system. The electrophoretograms is shown in FIG. 28.

The results show that as compared to the bands of DNA from the sample stored without stabilizer at −80° C., the bands of DNA from the sample stored with stabilizer were also distinct and bright, while the bands of DNA from the sample stored without stabilizer at room temperature were blurred and had low intensity.

Saliva samples were collected from volunteers, and the saliva samples were mixed sufficiently. 200 μL sample was mixed with an equal amount of one of the stabilizers with Formulations 2.5-2.8 respectively in a polypropylene bottle with screw cap. Two control samples without stabilizer were prepared, wherein one control sample stored at −80° C. was used as freezing control, and the other control sample (NP) together with the samples stored with stabilizer were placed at room temperature in dark. All the treatments were performed in duplicate, and the samples were stored under the corresponding conditions for 30 days. After the storage, total RNA was extracted from each of the samples by using RNAqueous™ Kit (Ambion Company, Austin, Tex.), and detailed steps were performed according to manufacturer's instructions. RNA integrity was evaluated by using Agilent RNA 6000 Nano Kit and Agilent 2100 Bioanalyzer (Agilent Technologies Inc., Santa Clara, Calif.), and the results were expressed as RIN (RNA integrity).

Figure 29:
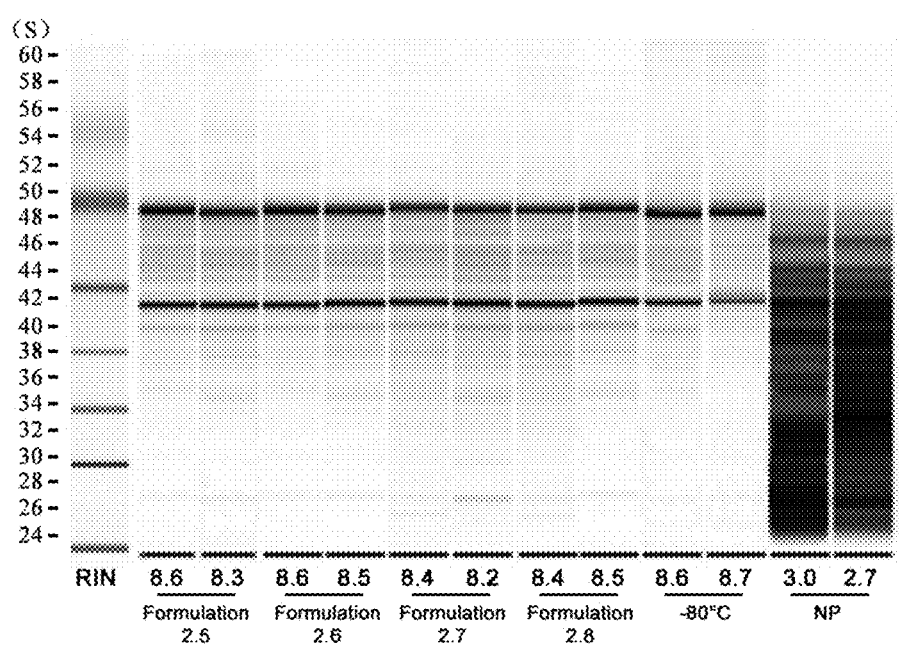
FIG. 29 shows the integrity (RIN) of the total RNA extracted from the human saliva samples stored under different conditions. The saliva sample was stored at room temperature with the addition of one of the stabilizers with Formulations 2.5-2.8 respectively; or directly stored at room temperature without stabilizer (NP); or stored at −80° C. without stabilizer. 30 days later, total RNA was extracted from the sample, and was evaluated for RNA integrity.

The results (FIG. 29) show that after the storage for 30 days, for the RNA from the samples stored with stabilizers with Formulations 2.5-2.8 at room temperature, the average values of RIN were 8.45, 8.55, 8.3 and 8.45, respectively (FIG. 13), which were substantively consistent with the average value of RIN (8.65) for the RNA from the sample stored at −80° C., while the average value of RIN was only 2.85 for the RNA from the sample stored without stabilizer at room temperature.

Although the embodiments of the invention have been described in detail, a person skilled in the art would understand that, a variety of modifications and replacements can be performed to the details according to all the teachings disclosed therein, and such changes all fall into the protection scope of the invention. The scope of the invention is defined by the appended claims and any equivalents thereof.

What is claimed is:

1. A method for storage of a polypeptide in a biological sample under non-freezing conditions, comprising:
   1) mixing the biological sample with a composition; and
   2) storage of the mixture obtained in step 1) under non-freezing conditions for at least 1 day, 3 days, 7 days, 10 days, 20 days, 30 days, 40 days, 50 days, 60 days, 70 days, 90 days or 180 days; and
   wherein the composition comprises:
   1) at least one compound of Formula I:

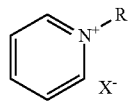  I wherein R is selected from the group consisting of: alkyl, alkenyl, cycloalkyl,
   cycloalkenyl, arylformylalkyl, and

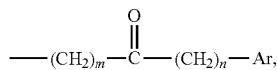

each of which is optionally substituted with a substituent selected from the group consisting of alkyl, hydroxyl, amino, nitro, and halogen;
   m and n are each independently 0, 1, 2 or 3; and
   X− represents an anion; and
   2) one, two or three of the following three agents:
   (1) at least one precipitant;
   (2) at least one lower alcohol; and
   (3) at least one chaotrope.

2. The method according to claim 1, wherein the biological sample comprises one or more selected from: DNA, RNA, whole blood, buffy coat of whole blood, urine, feces, serum, serosal fluid, plasma, lymph, cerebrospinal fluid, saliva, mucosal secretion, vaginal discharge, ascites, pleural fluid, pericardial fluid, peritoneal fluid, abdominal fluid, cell culture medium, tissue culture medium, buccal cells, bacterium, viruses, yeast cells, plasmid DNA, mRNA, tRNA, rRNA, siRNA, miRNA, hnRNA, cDNA, protein, polypeptide, lipid, glycolipid, glycoprotein, oligosaccharide, polysaccharide, vaccine, cell, tissue, cell lysate, homogenate or extract, tissue lysate, biopsy specimen, blood sample, tissue explant, organ culture and biology liquid.

3. The method according to claim 1, wherein the composition is characterized by any one or more of the following items:
   (1) the precipitant is selected from lithium chloride, lithium hydroxide, sulfosalicylic acid, and 5-((4-(dimethylamino)phenyl)methylene)-2-thioxo-4-thiazolidinone;
   (2) the lower alcohol is selected from methanol, ethanol, propanol, isopropanol, n-butanol and isobutanol; and
   (3) the chaotrope is selected from guanidine hydrochloride, guanidine thiocyanate, potassium thiocyanate, sodium thiocyanate and urea.

4. The method according to claim 1, wherein the composition further comprising one or more agents selected from:
   (a) a reducing agent;
   (b) a polymerase inhibitor;
   (c) a pH buffer;
   (d) a chelating agent; and
   (e) water.

5. The method according to claim 4, wherein the composition is characterized by any one or more of the following items:
   (1) the chelating agent is selected from diethylenetriaminepentaacetic acid (DTPA), ethylenediaminetetraacetic acid (EDTA), ethylene glycol-bis-(2-aminoethylether)-N,N,N',N'-tetraacetic acid (EGTA), 1,2-cyclohexanediaminetetraaceticacid (CDTA), 1,2-bis(2-aminophenoxy)-ethane-N,N,N',N'-tetraacetic acid (BAPTA), 1,4,7,10-tetraazacyclododecane-1,4,7,10-tetraacetic acid (DOTA), N-(2-hydroxyethyl)ethylenediamine-N,N',N'-triacetic acid (HEDTA), and nitrilotriacetic acid (NTA);
   (2) the reducing agent is selected from 2-mercaptoethanol, thiosulfate, tris(2-carboxyethyl)phosphine hydrochloride (TCEP), dithiothreitol, and dithioerythritol;
   (3) the pH buffer is selected from citric acid, tartaric acid, malic acid, sulfosalicylic acid, 5-sulfobenzene-1,3-dicarboxylic acid, oxalic acid, boric acid, N-(2-hydroxyethyl)piperazine, 3-(cyclohexylamino)-1-propanesulfonic acid (CAPS), 3-(cyclohexylamino)-2-hydroxyl-1-propanesulfonic acid (CAPSO), 4-(2-hydroxyethyl)-1-piperazinepropanesulfonic acid (HEPPS), N-2-hydroxyethylpiperazine-N-2-ethanesulfonic acid (HEPES), 2-morpholinoethanesulfonic acid (MES), 3-morpholinopropanesulfonic acid (MOPS), 3-(N-morpholino)-2-hydroxylpropanesulfonic acid (MOPSO), piperazine-1,4-(bisethanesulfonic acid) (PIPES), N-[tris(hydroxymethyl)methyl]-3-aminopropanesulfonic acid (TAPS), N-[Tris(hydroxymethyl)methyl]-3-amino-2-hydroxypropanesulfonic acid (TAPSO), N-[tris(hydroxymethyl)methyl]-2-aminoethanesulfonic acid (TES), diglycine, N-[tris(hydroxymethyl)methyl]glycine, tri(hydroxymethyl)aminomethane (tris) and 2-[bis(2-hydroxyethyl)amino]-2-(hydroxymethyl)-1,3-propanediol; and
   (4) the polymerase inhibitor is selected from one or more of rifamycin-S, rifamycin-SV, antimycin, and erythromycin.

6. The method according to claim 1, wherein the composition comprises one of the following formulations:
   (i) the compound of Formula I, a precipitant, a lower alcohol, a polymerase inhibitor, and a pH buffer;
   (ii) the compound of Formula I, a chaotrope, a lower alcohol, a polymerase inhibitor, and a pH buffer;
   (iii) the compound of Formula I, a precipitant, a lower alcohol, a reducing agent, and a pH buffer; and
   (iv) the compound of Formula I, a chaotrope, a lower alcohol, a reducing agent, and a pH buffer.

7. The method according to claim 6, wherein:
   the compound of Formula I is comprised in an amount of 1-10% (w/v or v/v);
   the chaotrope is comprised in an amount of 2.5-5M;
   the pH buffer is comprised in an amount of 50-400 mM;
   the lower alcohol is comprised in an amount of 20-50% (v/v);
   the reducing agent is comprised in an amount of 5-50 mM;
   the precipitant is comprised in an amount of 2.5-5M; and
   the polymerase inhibitor is comprised in an amount of 0.1-0.5 mM.

8. The method according to claim 1, wherein R is selected from the group consisting of: C1-10alkyl, C2-10alkenyl, C3-10cycloalkyl, C3-10cycloalkenyl, arylformylC1-10alkyl, and

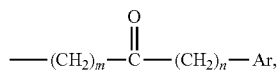

each of which is optionally substituted with a substituent selected from the group consisting of C1-10alkyl, hydroxyl, amino, nitro, and halogen;

m and n are each independently 0, 1, 2 or 3.

9. The method according to claim 1, wherein the anion is selected from the group consisting of bromine ion, chlorine ion, iodine ion, C1-10alkylsulfonate, hexafluorophosphate, methylsulfate, ethylsulfate, tetrafluoroborate, trifluoromethanesulfonate and bis(trifluoromethylsulfonyl)imide.

10. The method according to claim 1, wherein the compound of Formula I is selected from the group consisting of:

N-octylpyridinium bromide, N-butylpyridinium bromide, and N-phenacylpyridinium bromide.

11. The method according to claim 1, wherein the composition further comprises a surfactant or a detergent.

12. The method according to claim 11, wherein the surfactant or the detergent is selected from TritonX-100, Nonidet P40 and non-ionic detergent Brij.

* * * * *